(12) United States Patent
Hutchinson et al.

(10) Patent No.: US 9,364,554 B2
(45) Date of Patent: Jun. 14, 2016

(54) EXTRACELLULAR TARGETED DRUG CONJUGATES

(71) Applicants: Centrose, LLC, Madison, WI (US); Jill Hutchinson-Bollettieri, Saint Louis Park, MN (US)

(72) Inventors: Charles R. Hutchinson, St. Louis Park, MN (US); James R. Prudent, Madison, WI (US); Jon S. Thorson, Madison, WI (US)

(73) Assignee: Centrose LLC, Madison, WI (US)

( * ) Notice: Subject to any disclaimer, the term of this patent is extended or adjusted under 35 U.S.C. 154(b) by 118 days.

(21) Appl. No.: 13/897,911

(22) Filed: May 20, 2013

(65) Prior Publication Data

US 2013/0336994 A1    Dec. 19, 2013

Related U.S. Application Data

(63) Continuation of application No. 12/878,775, filed on Sep. 9, 2010, now Pat. No. 8,470,980.

(60) Provisional application No. 61/240,775, filed on Sep. 9, 2009, provisional application No. 61/289,811, filed on Dec. 23, 2009, provisional application No. 61/345,820, filed on May 18, 2010.

(51) Int. Cl.
| | | |
|---|---|---|
| *A61K 47/48* | (2006.01) | |
| *C07K 16/12* | (2006.01) | |
| *A61K 31/704* | (2006.01) | |
| *A61K 31/7052* | (2006.01) | |

(52) U.S. Cl.
CPC ......... *A61K 47/48369* (2013.01); *A61K 31/704* (2013.01); *A61K 31/7052* (2013.01); *A61K 47/48146* (2013.01); *A61K 47/48384* (2013.01); *A61K 47/48538* (2013.01)

(58) Field of Classification Search
CPC .................. A61K 47/48146; A61K 47/48538; A61K 31/7052; A61K 47/48384; A61K 31/704; A61K 47/48369; C07K 16/22; C07J 19/005; C07J 17/005
See application file for complete search history.

(56) References Cited

U.S. PATENT DOCUMENTS

| | | | |
|---|---|---|---|
| 3,987,031 A | 10/1976 | Losel et al. | |
| 4,555,504 A | 11/1985 | Jones | |
| 5,196,193 A | 3/1993 | Carroll | |
| 5,280,113 A | 1/1994 | Rademacher et al. | |
| 5,668,272 A | 9/1997 | Prasad et al. | |
| 5,833,988 A | 11/1998 | Friden | |
| 6,716,821 B2 | 4/2004 | Zhao et al. | |
| 8,088,387 B2 | 1/2012 | Steeves et al. | |
| 2004/0001838 A1 | 1/2004 | Zhao et al. | |
| 2005/0169933 A1 | 8/2005 | Steeves et al. | |
| 2006/0041109 A1 | 2/2006 | Thorson et al. | |
| 2006/0233794 A1 | 10/2006 | Law et al. | |
| 2007/0172422 A1 | 7/2007 | Glazier | |
| 2008/0003230 A1 | 1/2008 | Adair | |
| 2009/0202536 A1 | 8/2009 | Ebens, Jr. et al. | |

FOREIGN PATENT DOCUMENTS

| | | |
|---|---|---|
| WO | WO-2007024290 A2 | 3/2007 |
| WO | WO-2008121797 A1 | 10/2008 |
| WO | WO-2010017480 A1 | 2/2010 |

OTHER PUBLICATIONS

Jubala et al., Vet Pathol 42: 468-476, 2005.*
Golay et al., Archives of Biochemistry and Biophysics 526: 146-153, 2012.*
Hay et al., Nature Biotechnology 32(1): 40-51, Jan. 2014.*
Dermer et al., Bio/Technology 12: 320, 1994.*
International Preliminary Search Report on Patentability for International Application No. PCT/US2009/053159, Feb. 8, 2011.
International Search Report for International Application No. PCT/US2009/053159, Sep. 19, 2009.
International Search Report for International Application No. PCT/US2010/048284, dated Dec. 20, 2010.
Kahn, M.S.Y. et al., "A comprehensive review on the chemistry and pharmacology of *corchorus* species—A source of cardiac glycosides, triterpenoids, ionides, flavinoids, coumarins, steriods and some other compounds," Journal of Scientific & Industrial Research, Apr. 2006, vol. 65, pp. 283-298.
Stancovski et al., Proceedings of the National Academy of Science USA 88: 8891-8695, 1991.
Wang et al., Am J Physiol. Cell Physiol. 281(4):C1336-43, Oct. 2001.
Yu et al., Investigative Ophthalmology & Visual Science 49(2): 522-527, Feb. 2008.

\* cited by examiner

*Primary Examiner* — Phuong Huynh
(74) *Attorney, Agent, or Firm* — Perkins Coie LLP

(57) ABSTRACT

The present invention relates to, inter alia, extracellular drug conjugates (EDC) in which an antibody or other targeting agent (e.g. a targeting moiety) is linked to a drug through a linker (e.g. a non-cleavable linker). These conjugates are useful in the treatment of disease and/or as a tool in the evaluation of biological systems.

3 Claims, 6 Drawing Sheets

SEQUENCE LISTING

```
<160> NUMBER OF SEQ ID NOS: 1

<210> SEQ ID NO 1
<211> LENGTH: 178
<212> TYPE: PRT
<213> ORGANISM: Homo sapiens
<400> SEQUENCE: 1

Met Ser Pro Ser Gly Arg Leu Cys Leu Leu Thr Ile Val Gly Leu Ile
1               5                   10                  15

Leu Pro Thr Arg Gly Gln Thr Leu Lys Asp Thr Thr Ser Ser Ser Ser
                20                  25                  30

Ala Asp Ser Thr Ile Met Asp Ile Gln Val Pro Thr Arg Ala Pro Asp
            35                  40                  45

Ala Val Tyr Thr Glu Leu Gln Pro Thr Ser Pro Thr Pro Thr Trp Pro
        50                  55                  60

Ala Asp Glu Thr Pro Gln Pro Gln Thr Gln Thr Gln Gln Leu Glu Gly
65                  70                  75                  80

Thr Asp Gly Pro Leu Val Thr Asp Pro Glu Thr His Lys Ser Thr Lys
                85                  90                  95

Ala Ala His Pro Thr Asp Asp Thr Thr Thr Leu Ser Glu Arg Pro Ser
            100                 105                 110

Pro Ser Thr Asp Val Gln Thr Asp Pro Gln Thr Leu Lys Pro Ser Gly
        115                 120                 125

Phe His Glu Asp Asp Pro Phe Phe Tyr Asp Glu His Thr Leu Arg Lys
    130                 135                 140

Arg Gly Leu Leu Val Ala Ala Val Leu Phe Ile Thr Gly Ile Ile Ile
145                 150                 155                 160

Leu Thr Ser Gly Lys Cys Arg Gln Leu Ser Arg Leu Cys Arg Asn His
                165                 170                 175

Cys Arg
```

EXTRACELLULAR TARGETED DRUG CONJUGATES

CROSS-REFERENCE TO RELATED APPLICATION(S)

This application is a continuation of U.S. patent application Ser. No. 12/878,775, filed Sep. 9, 2010, entitled EXTRACELLULAR TARGETED DRUG CONJUGATES, which claims priority to U.S. Application No. 61/345,820, filed May 18, 2010, U.S. Application No. 61/289,811, filed Dec. 23, 2009, and U.S. Application No. 61/240,775 filed Sep. 9, 2009, the entireties of each of which are hereby incorporated by reference herein.

TECHNICAL FIELD

The present invention provides drug conjugates in which an antibody or other targeting agent (e.g. a targeting moiety) is linked to a drug through a linker (e.g. a non-cleavable linker). In one embodiment, the drug acts on an extracellular target. These conjugates are useful in the treatment of disease and/or as a tool in the evaluation of biological systems. The invention relates to the fields of biology, chemistry, medicinal chemistry, medicine, molecular biology, and pharmacology.

BACKGROUND

All fundamental biological processes, including development, immunity, and tumorigenesis, are related to the selective and differential expression of genes in different tissues and cell types. For example, the formation of many malignant tumors has been shown to be associated with the production and/or expression of certain specific cell surface signaling molecules. One of the goals of modern molecular medicine is to find ways to target drugs selectively to reduce or eliminate the drug's off target toxic effects. Delivering drugs to a specific target that is unique to or expressed at higher levels in diseased cells types using targeting moieties such as antibodies, peptides or aptamers has been tried. Attaching these targeting moieties directly to the drug through linkers or to nanoparticles has also been tried.

One such drug targeting system is termed, "antibody drug conjugates" or ADC for short has been studied intensively since 1985 (see, for example, U.S. Patent Publication No. 2009/0220529, incorporated herein by reference). Members of this class of targeted therapeutics are composed of an antibody specific to an antigen, a drug or drugs that act intracellularly, and a linker that connects the antibody to the drug(s). To make ADCs, a wide array of antibodies, linkers, and drugs have been combined and tested in a continuing effort to identify antibodies that specifically target certain cell types and release active drug only upon binding and internalization. Unfortunately, a number of technical difficulties have been encountered with the ADC approach, including the difficulty of finding a means to link the antibody and drug where the linker is stable in the circulatory structure but "unstable" once the ADC has bound to its target or has been internalized into the target cell. Drug release in the circulatory structure before the antibody binds its target or is internalized can lead to undesired toxicity or off target effects. Failure to release the drug after the antibody-target binding or internalization can lead to reduced efficacy. In addition, the linkage must be such that the drug is in an active form when released. Together, these requirements impose considerable design constraints. So it is not surprising that, in all examples to date, ADCs require some sort of separation of the drug from the antibody.

In addition, there have been no cases to date where the target for the drug is in close enough proximity to the antibody's target where both the linked drug and antibody act simultaneously. In all cases, acceptable cytotoxicity of an ADC was realized only if some sort of membrane penetration by the drug occurred. In these cases the drug was either released from the conjugate at the target site outside of the cell (see, e.g., U.S. Pat. No. 5,475,092) or after the complete conjugate was internalized.

Another difficulty encountered with the approach relates to how much active drug can be delivered to a target inside the cell by the ADC. Generally, there are only a small number of copies of each different disease-specific antigen binding site at the cell surface, and the number of drug molecules that can be linked to a single antibody without interfering with antigen (target) binding is relatively low (between 5 to 10 per antibody). These two factors in combination have made the ADC approach practical only when very potent (typically very toxic) drugs are used.

Another difficulty encountered with the approach relates to multidrug resistance mechanisms of internalized drugs. For example, cancer cells have the ability to become resistant to multiple different drugs, and share many of the same mechanisms, which include increased efflux of drug (as by P-glycoprotein, multidrug resistance-associated protein, lung resistance-related protein, and breast cancer resistance protein and reproductive cancer resistance protein; enzymatic deactivation (i.e., glutathione conjugation); and decreased permeability (drugs cannot enter the cell). Because efflux is a significant contributor for multidrug resistance in cancer cells, current research is aimed at blocking specific efflux mechanisms.

Yet another drawback with the ADC approach is that the targets have been limited to targets that internalize upon ADC binding. In some cases, even though the target for the ADC exists on the cell surface, internalization does not occur. This makes the ADC approach cell type specific and target specific. Complicating this even further are the cases where the target is expressed and internalization occurs, but the internalization is within compartments where drug antibody dissociation does not occur, leaving the drug ineffective.

Given all these constraints, it is not surprising that Mylotarg [the only ADC approved by the FDA for human therapeutic use (see Hamann, Bioconjug Chem, 13: 40-46, 2002)] was recently removed from the market due to limited efficacy, and no other ADC has been approved to date. Therefore, there continues to be a need for improved ADCs that circumvent these requirements and/or overcome the difficulties and drawbacks of existing methods. The present invention meets that need.

SUMMARY

In various embodiments, the present invention relates to a new technology to deliver therapeutic agents selectively (e.g. to antigens) and provides a new class of antibody drug conjugate (ADC) as well as other drug conjugates using targeting agents, which may be termed Extracellular-targeted Drug Conjugates (EDCs). In various embodiments, the present invention provides these EDCs, which are a new type of drug conjugate, as well as other compositions and drug delivery systems. In various embodiments, 1) the EDC of the invention remains intact or non-dissociated to be most effective, 2) the EDC of the invention works extracellularly, and 3) the agent and the targeting moiety bind to two or more targets or the same target. Thus, in one embodiment, to obtain maximal therapeutic effect, the linker of the EDC remains intact, internalization does not occur, and the targeting moiety and the agent work in concert together to achieve the desired therapeutic effect.

In a first aspect, the invention provides an EDC in which the therapeutic agent is covalently linked to a targeting moiety (e.g. an antibody) through a stable (and, in some embodiments, non-cleavable) linker that remains intact and uncleaved for the EDC to exert its maximal therapeutic effect. In one embodiment, the targeting moiety of the EDC targets an extracellular target, and the target of the agent of the EDC is extracellular. In another embodiment, the target targeted by the targeting moiety of the ADC is also the target of the therapeutic agent. In another embodiment, the target for the targeting moiety resides within a complex that includes the target for the agent. In other 'embodiments, the targets of the therapeutic agent and targeting moiety are different and not associated in a macromolecular complex but are located on the cell surface in close proximity to one another. Thus, in various embodiments, the targeting moiety's target is distinct from the target of the therapeutic agent, but the two targets exist within close proximity such that the targeting moiety and agent act in concert or even synergistically with one another. Thus, the EDC of the invention is generally only therapeutically effective when both the targeting moiety's and agent's targets are in close proximity to one another. In one embodiment, the linker in an EDC of the invention is a non-cleavable polyethylene glycol linker. In one embodiment of an EDC of the invention, a single agent is attached to a single targeting moiety through a stable or non-cleavable linker, and the targeting moiety and drug bind to their targets and/or act simultaneously or substantially simultaneously. In one embodiment, the activity of the EDC can be regulated by the length of the non-cleavable linker.

In a second aspect, the invention provides a composition that comprises, or alternatively consists or consists essentially of, as an active ingredient, an EDC of the invention. In one embodiment, the composition is a pharmaceutical formulation suitable for parenteral, including but not limited to intravenous, administration. In one embodiment, the invention provides pharmaceutical formulations that comprise, or alternatively consist or consist essentially of, an EDC of the invention in combination with a pharmaceutically acceptable vehicle, vector, diluent, and/or excipient. In other embodiments, the invention provides compositions that contain, in addition to an EDC of the invention, at least one other active pharmaceutical ingredient.

The pharmaceutical formulations of the invention can be used in vivo for preventive, ameliorative, and/or curative purposes for diseases or disorders. Non-limiting examples of diseases or disorders for which the pharmaceutical formulations according to the invention may be used include cancers, metastases, cellular apoptosis disorders, degenerative diseases, tissue ischemia, infectious diseases of a viral, bacterial or fungal nature, inflammation disorders, diabetes and pathological neo-angiogenesis. Thus, in accordance with the methods of the invention, a subject can be treated with a pharmaceutically effective amount of a compound or composition according to the invention. In one embodiment of the invention, the subject is a human subject.

Thus, in a third aspect, the invention provides methods for treating a disease or other medical condition by administering to a patient in need of treatment a therapeutically effective dose of an EDC or other compound or pharmaceutical composition of the invention. The methods, compounds, and compositions of the invention are generally useful for the treatments of medical conditions where therapeutic agents specific to extracellular targets are administered. In various embodiments, the invention provides methods for treating or preventing a disorder selected from the group consisting of cellular proliferative and/or differentiative disorders, disorders associated with bone metabolism, immune disorders, hematopoietic disorders, cardiovascular disorders, liver disorders, kidney disorders, muscular disorders, neurological disorders, hematological disorders, viral infections, pain, and metabolic disorders. In one embodiment, the invention provides methods for the treatment of cancer.

In a fourth aspect, the invention provides novel cardiac glycosides (e.g. CEN09-106 or CEN10-110) that are anti-cancer agents, and the invention also provides EDCs comprising these cardiac glycosides, pharmaceutical compositions comprising these cardiac glycosides or EDCs comprising them, and methods for their manufacture and use.

In a fifth aspect, the invention provides methods for the manufacture of the compounds, EDCs, and compositions of the invention, including the use of the EDC compounds and compositions for the formulation and preparation of biological, pharmaceutical, cosmetic, and agricultural products. In one embodiment, the invention pertains to uses of the compounds of the invention for the manufacture of a medicament for treating a disease.

In a sixth aspect, the invention provides methods of treating a disease with an EDC of the invention in combination with one or more other therapeutics such that the combination acts to enhance or magnify one or more therapeutic effects, as compared to the use of either therapeutic alone.

DETAILED DESCRIPTION

Figure 1:
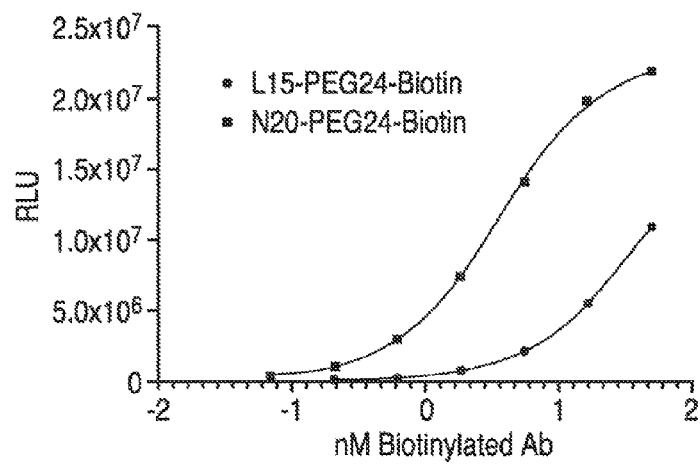
FIG. 1 shows antibody-linker-biotin binding to peptide of sequence 24-39 of SEQ ID NO 1 after the addition of the antibody-linker-biotin conjugates at the indicated concentrations. See Example 3.

The present invention provides a new type of drug conjugate, the EDC, useful in a variety of applications, particularly the treatment of human disease and other medical conditions. To facilitate an understanding of the invention, this detailed description is divided into sections. Section I provides definitions of terms used in this disclosure. Section II describes targeting moieties useful in the EDCs of the invention. Section III describes linkers useful in the EDCs of the invention. Section IV describes therapeutic agents useful in the invention. Section V describes particular embodiments of the EDCs of the invention. Section VI describes peptides and antibodies provided by the invention, Section VII describes pharmaceutical formulations of the inventions and methods for administering them to treat disease and other medical conditions. The detailed description of the invention is followed by a set of examples that illustrate useful methods and EDCs of the invention.

U.S. Provisional Application Nos. 61/240,775, 61/289, 811, and 61/345,820, and all other patents, patent applications, and references from the scientific literature cited herein, are hereby incorporated by reference herein in their entireties.

I. DEFINITIONS

The term "aldehyde tag" or "ald-tag" is a peptide or peptidomimetic that contains an amino acid sequence derived from a sulfatase motif that is capable of being converted, or which has been converted, by action of a formylglycine generating enzyme (FGE) to contain a 2-formylglycine residue (referred to herein as "FGly"). The FGly residue generated by an FGE is often referred to in the literature as a "formylglycine", although this is technically incorrect. Thus, "aldehyde tag", as used herein, can refer to an amino acid sequence comprising an "unconverted" sulfatase motif (i.e., a sulfatase motif in which the cysteine or serine residues has not been converted to FGly by an FGE, but is capable of being converted) or to an amino acid sequence comprising a "converted" sulfatase motif (i.e., a sulfatase motif in which the cysteine or serine residues have been converted to FGly by action of an FGE).

The term "amino acid" refers to naturally occurring and non-natural amino acids, as well as amino acid analogs and amino acid mimetics. Naturally occurring amino acids are those encoded by the genetic code, as well as those amino acids that are not encoded by the genetic code and those that are modified form of encoded amino acids, e.g., beta-alanine, D-serine, hydroxyproline, .gamma.-carboxygluta mate, and 0-phosphoserine. Amino acid analogs are compounds that have the same basic chemical structure as a naturally occurring amino acid, i.e., a carbon that is bound to a hydrogen, a carboxyl group, an amino group, or various R groups making non-naturally occurring amino acids (e.g., homoserine, norleucine, methionine sulfoxide, methionine methyl sulfonium). Such analogs have modified R groups (e.g., norleucine) or modified backbones, but retain the same basic chemical structure as a naturally occurring amino acid, e.g. beta amino acids, amino acids in D conformation. Amino acid mimetics refers to chemical compounds that have a structure that is different from the general chemical structure of an amino acid, but that functions in a manner similar to a naturally occurring amino acid.

The term "antibody" refers to a protein or mixture of proteins that comprise one or more peptidic chains encoded by immunoglobulin genes or fragments thereof that specifically bind and recognize an epitope of an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. The antibodies comprise IgG (including $IgG_1$, $IgG_2$, $IgG_3$, and $IgG_4$), IgA (including $IgA_1$ and $IgA_2$), IgD, IgE, or IgM, and IgY. As used herein, the term "antibody" is meant to include whole antibodies, including single-chain antibodies, and antigen-binding fragments thereof. Antibodies can also be antigen binding antibody fragments and include, but are not limited to, Fab, Fab' and $F(ab')_2$, Fd, single-chain Fvs (scFv), single-chain antibodies, disulfide-linked Fvs (sdFv), diabodies, triabodies, tetrabodies, minibodies, and fragments comprising either a $V_L$ or $V_H$ domain, and Nanobodies (see PCT publication number WO 94/04678 and Nature Medicine, V9 (1) pp 129-134, 2003). An antibody can be from any animal origin including birds and mammals. Typically, antibodies in commercial or research use are human, murine, rabbit, goat, guinea pig, camelidae (e.g., camel, llamas) horse, or chicken antibodies. "Antibodies", as used herein, includes monoclonal, immunoadsorbed polyclonal, chimeric, and humanized antibodies, as well as intact antibodies and isolated antibodies. Antibodies can be monospecific, bispecific, trispecific or greater multispecificity.

The term "antibody drug conjugate" or "ADC" refers to an antibody linked to a therapeutic agent (sometimes referred to herein as agent, drug, or active pharmaceutical ingredient) or agents.

The term "extracellular-targeted drug conjugate" or "EDC" refers to a drug conjugate of the invention in which an antibody or other targeting moiety that targets an extracellular target is linked via a stable or non-cleavable linker to a drug that binds to an extracellular target.

The term "antigen" refers to the substance or target that an antibody or targeting moiety binds. An antigen is characterized by its ability to be "bound" by the antibody or targeting moiety. Antigen can also mean the substance used to elicit the production of targeting moieties, such as the production of antigen specific antibodies through immunizing with the antigen.

The term "antigen binding site" or "epitope" refers to the portion of the antigen to which a targeting moiety, such as an antibody, binds.

The term "aptamer" refers to a DNA, RNA, or oligonucleotide mimetic that is a targeting moiety and can be the functional equivalent of an antibody and specifically binds and recognizes an epitope of an antigen.

The term "binding affinity" refers to the strength of interaction between an antibody (or other targeting moiety or drug or other agent) and its antigen (or target) as a function of its association and dissociation constants. Higher affinities typically mean that the targeting moiety has a fast on rate (association) and a slow off rate (dissociation). Binding affinities can change under various physiological conditions and changes that occur to the antigen or antibody/targeting moiety under those conditions. Binding affinities of the targeting moiety can also change when therapeutic agents and/or linkers are attached. Binding affinities can also change when slight changes occur to the antigen, such as changes in the amino acid or glycosylation of the antigen.

The term "cancer" refers to any of a number of diseases characterized by uncontrolled, abnormal proliferation of cells, the ability of affected cells to spread locally or through the bloodstream and lymphatic system to other parts of the body (i.e., metastasize), as well as any of a number of characteristic structural and/or molecular features. A "cancerous cell" or "cancer cell" is understood as a cell having specific structural properties, which can lack differentiation and be capable of invasion and metastasis. Examples of cancers are, breast, lung, brain, bone, liver, kidney, colon, and prostate cancer (see DeVita, V. et al. (eds.), 2005, Cancer Principles and Practice of Oncology, 6th. Ed., Lippincott Williams & Wilkins, Philadelphia, Pa., incorporated herein by reference in its entirety for all purposes).

The term "chimeric antibodies" refers to antibodies in which the Fc constant region of a monoclonal antibody from one species (typically a mouse) is replaced, using recombinant DNA techniques, with an Fc region from an antibody of another species (typically a human). For example, a cDNA encoding a murine monoclonal antibody is digested with a restriction enzyme selected specifically to remove the sequence encoding the Fc constant region, and the equivalent portion of a cDNA encoding a human Fc constant region is substituted. A CDR-grafted antibody is an antibody in which at least one CDR of a so-called "acceptor" antibody is replaced by a CDR "graft" from a so-called "donor" antibody possessing desirable antigen specificity. Generally the donor and acceptor antibodies are monoclonal antibodies from different species; typically the acceptor antibody is a human antibody (to minimize its antigenicity in a human), in which case the resulting CDR-grafted antibody is termed a "humanized" antibody. The graft may be of a single CDR (or even a portion of a single CDR) within a single $V_H$ or $V_L$ of the acceptor antibody, or can be of multiple CDRs (or portions thereof) within one or both of the VH and VL. Methods for generating CDR—grafted and humanized antibodies are taught by Queen et al. U.S. Pat. No. 5,585,089, U.S. Pat. No. 5,693,761 and U.S. Pat. No. 5,693,762; and Winter U.S. Pat. No. 5,225,539, which are incorporated herein by reference.

The term "close proximity" refers to two targets X and Y that are in physical proximity such that when a targeting moiety (to X) and therapeutic agent (to Y) are conjugated through a linker, the conjugate induces a desired biological or medical response. In one embodiment, the biological or medical response achieved is greater than that observed by either the targeting moiety or therapeutic agent alone. In another embodiment, the biological or medical response achieved is greater than that observed by the additive effects of the targeting moiety and therapeutic agent. In another embodiment, where X and Y are on the same molecule, the targets are in "close proximity" to each other. In one embodiment, when X and Y are located on different molecules, but the molecules are present in the same multi-molecular complex, the targets are in "close proximity" as defined herein. In another embodiment, when X and Y are on the same cell within 200 or fewer Angstroms from one another, the targets are in "close proximity" to one another. When X and Y are on different cells (that are not within 200 Angstroms or less apart from one another), they are not in "close proximity".

The term "circulatory structure" refers to body fluids, interstitial fluid, lymph and blood of a mammal, including tissues of the circulatory system.

The terms "FXYDS", "dysadherin", "ATPase subunit gamma 5", or "gamma 5" are used interchangeably herein and refer to the gamma subunit 5 of the Na,K-ATPase ion pump complex.

The term "epitope" refers to groupings of molecules such as amino acid residues or sugar side chains at the surface of antigens that usually have specific three dimensional structural characteristics, as well as specific charge characteristics, and that are capable of specific binding by a monoclonal antibody.

The term "extracellular" refers to proteins, antigens, or epitopes located on the external portion of a cell membrane or are in the fluids of the circulatory structure (for example, a ngiotensin converting enzyme is an extracellular protein).

The term "intact antibody" comprises at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as $LCVR^X$ or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: $FR_1$, $CDR_1$, $FR_2$, $CDR_2$, $FR_3$, $CDR_3$, $FR_4$. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. Examples of binding fragments include (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature 341: 544-546, 1989), which consists of a $V_H$ domain; and (vi) an isolated complementarily determining region (CDR).

The term "hetereobifunctional linker" refers to a linker with different reactive groups at either end, enabling sequential conjugation between two different functional groups in proteins and other molecules.

The term "extracellular target" refers to a target, such as a protein, antigen, and/or epitope located on the cell membrane. For example and without limitation, the following are extracellular targets: cell surface receptors, cell surface ion channels, CD (cluster of differentiation or designation) abbreviated proteins. More specifically, and again without limitation, the following are extracellular targets: transmembrane protein gp41, angiotensin converting enzyme, Apo2L/TRAIL, podoplanin, Eag1, MCT1, integrin, and gangliosides. Generally, the targets for the targeting moiety and therapeutic agents of the EDCs of the invention are both extracellular targets on the outer surface of the cell membrane. However, in some embodiments the therapeutic may bind to a target embedded in (for example an ion-channel blocker) the cell membrane. Targets that are not generally considered extracellular targets include, for example, chromosomal DNA, mRNA, tRNA, mTOR kinase, DNA and RNA polymerases, transcription factors, tubulin, and actin.

The term "linker" refers to a chemical moiety or bond that covalently attaches two or more molecules, such as a targeting moiety and a drug.

The term "linker spacer group" refers to atoms in the linker that provide space between the two molecules joined by the linker.

The term "monoclonal antibody" refers to a preparation of antibody molecules of single molecular composition. A monoclonal antibody composition displays a single binding specificity and affinity for a particular epitope. The term "human monoclonal antibody" refers to antibodies displaying a single binding specificity which have variable and constant regions (if present) derived from human germline immunoglobulin sequences. Human monoclonal antibodies can be produced by a hybridoma which includes a B cell obtained from a transgenic non-human animal, e.g., a transgenic mouse, having a genome comprising a human heavy chain transgene and a light chain transgene fused to an immortalized cell, although the term "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

The term "modified antibodies" refers to antibodies, such as monoclonal antibodies, chimeric antibodies, and humanized antibodies, which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Multiple molecules of a therapeutic agent or multiple different agents can be coupled to one antibody molecule. For example, different moieties can be coupled to an antibody molecule via the same linker, or multiple linkers that provide multiple sites for attachment (e.g., dendrimers) can be used.

The terms "non-cleaved" and "uncleaved" refer to an EDC composition at any point in time in which the majority (for example, >50%, >60%, >70% or >80%) of EDC components present are intact, i.e., the linker used to attach the agent to the targeting moieties has not been cleaved.

The term "non-cleavable linker" refers to a stable linker that has the property of being more stable in vivo than either the therapeutic or the targeting moiety under the same physiological conditions. Examples of non-cleavable linkers include linkers that contain polyethylene glycol chains or polyethylene chains that are not acid or base sensitive (such as hydrazone containing linkers), are not sensitive to reducing or oxidizing agents (such as those containing disulfide linkages), and are not sensitive to enzymes that may be found in cells or circulatory system. Specific examples of non-cleavable linkers include SMCC linker (US Patent Application 20090202536). For illustrative purposes, examples of cleavable linkers include linkers that contain non-hindered glutathione sensitive disulfides, esters, peptide sequences sensitive to the peptidases such as cathepsin or plasmin, pH sensitive hydrazones [see *Bioconjugate Chem.*, 2010, 21 (1), pp 5-13]. Specific examples of cleavable linkers include non-hindered disulfide linker SPP (US Patent Application 20090202536). In various embodiments, a non-cleavable linker has one or more of the following properties that can be readily characterized experimentally: 1) the non-cleavable linker remains relatively intact keeping the therapeutic agent attached to the targeting moiety for extended periods of time (e.g., between at least about 2 to 8 hours, or at least 1 to 5 days, or at least 5 to about 30 days) under physiological conditions; 2) the non-cleavable linker is stable to enzymes, e.g. in the circulatory structure; 3) the non-cleavable linker allows the EDC to maintain activity even after it has acted on a target on a cell; 4) the non-cleavable linker does not negatively interfere with the binding activity or specificity of the targeting moiety; and/or 5) the non-cleavable linker does not negatively interfere with the activity of the therapeutic agent. Attachment of a stable or non-cleavable linker may have an effect on a therapeutic agent; for example, the cytotoxicity of a cytoxic agent may be decreased (but, in the EDCs of the invention, is not eliminated) by linker attachment. Any decrease in activity caused by linker attachment, however, is more than offset by an increased therapeutic efficacy of the EDC comprising the linker and agent. Thus, the agent attached to the targeting moiety via the non-cleavable or stable linker displays benefits over the agent alone. Such benefits may include solubility, lower toxicity, improved pharmacokinetics, and/or increased therapeutic efficacy.

The terms "non-internalizing targeting moiety" or "non-internalizing antibody" refer to a targeting moiety or antibody, respectively, that has the property of reacting (binding) under physiological conditions (at 37° C. and pH 7) in vivo or in vitro, to antigens outside of a cell, within the circulatory structure, or on a cell surface, and that, when bound to its target antigen, does not enter the cell and become degraded in the lysosome (see Cancer Res 2009; 69(6) 2358-64). In one embodiment, the targeting moiety or antibody, when bound to its target antigen, does not enter the cell and become internalized in an endosome. The target of a "non-internalizing targeting moiety" or "non-internalizing antibody" is referred to herein as a "non-internalizing target," which is a target that does not get internalized into the lysosome as a result of binding to a targeting moiety or antibody. Non-internalizing targets may, however, become internalized into the cell in other biological processes. Examples of non-internalizing targets include, but are not limited to CD20, CD21, and CD72. For illustrative purposes, "internalizing targets" include, for example and without limitation, CD79, and CD22.

The term "non-internalizing therapeutic agent" refers to a therapeutic agent (drug) that has the property of reacting in physiological conditions (at 37° C. and pH 7) in vivo or in vitro, with its target (typically, via binding to its receptor) without being internalized into cells.

The term "polyclonal antibody" refers to a preparation of more than one (two or more) different antibodies to an antigen. Such a preparation includes antibodies binding to a range of different antigen binding sites.

The terms "pharmaceutically effective amount" and "effective amount" in the context of an amount of drug delivered refer to an amount of a drug that can induce a desired biological or medical response in a tissue, system, animal, or human.

The terms "peptide", "polypeptide", peptidomimetic and "protein" are used, somewhat interchangeably, to refer to a polymer of amino acid residues. The terms apply to amino acid polymers in which one or more amino acid residues is an artificial chemical mimetic of a corresponding naturally occurring amino acid, as well as to naturally occurring amino acid polymers. These terms also encompass the term "antibody". "Peptide" is often used to refer to polymers of fewer amino acid residues than "polypeptides" or "proteins". A protein can contain two or more polypeptides, which may be the same or different from one another.

The term "receptor" refers to an extracellular target protein molecule, embedded in either the plasma membrane or the cytoplasm of a cell, to which one or more specific kinds of signaling molecules may bind. Each cell typically has many receptors, of many different kinds.

The term "substantially simultaneously" refers to two or more events that occur at the same time or within a relatively narrow time frame. In various embodiments, substantially simultaneously refers to two or more events that occur within about 60, about 40, about 30, about 20, about 10, about 5, about 2 or about 1 second of each other. For example, EDCs of the invention have properties such that targeting moiety binding and agent (drug) action happen substantially simultaneously.

The term "stable in the circulatory structure" refers to the property of a compound, such as an EDC, to resist degradation and means that, for example, less than about 50%, or less than about 20%, or typically less than about 2%, of the compound is degraded or cleaved in the circulating blood at about 37° C. for at least about 2 hours.

The term "stable linker" refers to a linker that remains stable and intact until the conjugate has been delivered or transported to the target site—a stable linker remains covalently attached to the two molecules it links—in physiological conditions (at 37° C. and pH 7) in vivo or in vitro for a period of time sufficient to allow the EDC to reach the target(s) and bind to the target(s). Thus, a stable linker is generally stable within the circulatory structure (generally means below 5% degradation after at least a 2 hour period and, in some embodiments, at least 4, 8, 16, or 24 hour periods). A stable linker maybe be cleaved by enzymes or physiological conditions (such as differing pH's) inside a cell, tissue, or organ. Examples of "stable" linkers include non-cleavable linkers, but stable linkers can be cleavable, so long as they generally aren't cleaved in vivo prior to the EDC reaching and binding to its target(s). For example, stable linkers can contain hindered glutathione sensitive disulfides, peptide sequences sensitive to the peptidases such as cathepsin, or pH sensitive hydrazones [see *Bioconjugate Chem.*, 2010, 21 (1), pp 5-13 and Clin. Cancer Res. 2005 11(2 Pt 1):843-52]. Thus a stable linker can be a cleavable linker but only if the linker is not cleaved prior to the EDC that contains such linker reaching its target(s). For example, a cathepsin cleavable linker is a stable linker, because cathepsin is only found in the lysosome which is intracellular. Examples of unstable linkers are linkers that contain ester or acyl hydrazone linkages.

The term "synergistically" refers to an effect of two or more agents when used in combination that is greater than the sum of the effects of both agents when used alone. For example, in the EDCs of the invention, the combined therapeutic effects of the interaction of the targeting moiety and the agent (drug) when linked through a linker are greater than the combined individual effects of the targeting moiety and agent when used alone. "Effects" can refer either to binding, therapeutic effect, and/or specificity.

The term "target" refers to the protein, glycoprotein, antigen, carbohydrate or nucleic acid to which a targeting moiety binds and also refers to the protein, glycoprotein, antigen, carbohydrate or nucleic acid to which a therapeutic agent binds. The agent and targeting moiety may bind to different targets in a "target complex", where "target complex" refers to two or more molecules, such as the different subunits of a multi-subunit protein or two different proteins in a multi-protein complex, that are in close physical proximity with one another in vivo.

The term "target cells" refers to the cells that are involved in a pathology and so are preferred targets for therapeutic activity. Target cells can be, for example and without limitation, one or more of the cells of the following groups: primary or secondary tumor cells (the metastases), stromal cells of primary or secondary tumors, neoangiogenic endothelial cells of tumors or tumor metastases, macrophages, monocytes, polymorphonuclear leukocytes and lymphocytes, and polynuclear agents infiltrating the tumors and the tumor metastases.

The interchangeable terms "targeting moiety" and "targeting agent" refer to an antibody, aptamer, peptide, or other substance that binds specifically to a target. A targeting moiety may be an antibody targeting moiety (e.g. antibodies or fragments thereof) or a non-antibody targeting moiety (e.g. aptamers, peptides, or other substances that bind specifically to a target).

The term "target tissue" refers to target cells (e.g., tumor cells) and cells in the environment of the target cells.

The terms "therapeutic agent" and "drug" and "agent" are used herein to refer to a compound that, when present in a therapeutically effective amount, upon binding to a site of action, produces a therapeutic effect, and whose site of action is located or whose effect will be exerted on the surface or inside target cells. By way of example, a therapeutic agent may be a chemical agent, such as an antibiotic or anti-cancer agent, a polypeptide, a protein, or a nucleic acid.

The term "therapeutic effect" refers to the reduction, elimination, and/or prevention of a disease, symptoms of the disease, or side effects of a disease in a subject.

The term "to increase the half-life time" means to increase the mean residence time of a compound, typically a therapeutic agent, in the blood or to reduce the blood or plasmatic clearance compared to a reference compound.

The terms "treating" and "treatment" are used interchangeably to refer to the administration of a therapeutic agent or composition to a patient who has a disease or disorder (e.g., cancer or metastatic cancer), a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease. "Treating" or "treatment" of cancer or metastatic cancer refers to the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters, including the results of an examination by a physician. Accordingly, the term "treating" includes the administration of a therapeutic agent to prevent or delay, to alleviate, or to arrest or inhibit development of the symptoms or conditions associated with a disease, including but not limited to neoplastic disease.

The term "tumor specific antigen" refers to proteins or other molecules that are unique to a tumor or is at least more abundant on tumor cells, relative to normal cells.

II. ANTIBODIES AND OTHER TARGETING MOIETIES

The present invention provides EDCs comprising a targeting moiety linked to a therapeutic agent via a stable or noncleavable linker (i.e., a linker that has to be intact or non-cleaved for the EDC to exert its maximal therapeutic effect) and methods employing these EDCs to deliver therapeutic agents more selectively to target cells or a target tissue. Thus, in all embodiments, the EDC contains a targeting moiety that binds to an extracellular target, and while attached to a therapeutic agent via a stable or non-cleavable linker, exerts a therapeutic effect. In some embodiments, the targeting moiety and therapeutic agent bind to or act on different extracellular targets. In other embodiments, the targeting moiety and the therapeutic agent bind to or act on the same target and are attached to each other via a stable or non-cleavable linker.

The targeting moiety of the EDCs of the invention directs the EDC to the target cell or target tissue that contains the target of the targeting moiety and the target of the therapeutic agent. Thus in some embodiments, the therapeutic agent produces the desired therapeutic effect but can also enhance the targeting properties of the EDC. In some embodiments, the targeting moiety and the agent work synergistically at directing the EDC to the target or targets. In some embodiments, the targeting moiety also has a therapeutic effect. In all embodiments, the stable or non-cleavable linker maintains the attachment of the targeting moiety to the therapeutic agent under physiological conditions for a sufficient period of time for the EDC to bind and exert a therapeutic effect. The three portions of the EDC of the invention thus comprise, consist essentially of or consist of: (1) a targeting moiety that binds to an extracellular target; (2) a stable or non-cleavable linker or a linker that remains intact or uncleaved for the EDC to exert a therapeutic effect; and (3) a therapeutic agent that binds to an extracellular target. Each of these key components is discussed in this and the immediate following sections of this detailed description.

In many embodiments of the EDCs of the invention, the targeting moiety is a human sequence antibody that does not induce internalization and thus is typically not internalized into the lysosome once bound to its target. Substantial efforts have been made to exploit antibodies to carry highly toxic payloads to infected or cancerous cells to bring and release drugs inside of cells, the "antibody-drug conjugate" or "ADC" approach.

A first difficulty associated with this approach, is that the ADC had to enter the cell to exert a therapeutic effect. Approaches to allow the ADC to enter the cell intact include targeting receptors that internalize the ADC or using peptide-mediated membrane penetration to deliver antibodies to their intracellular target proteins (see US Pat. App. 20080063633). Many such receptors that have been found to become internalized upon antibody binding in one cell type may not be internalized in another, limiting the generality of the approach [see Cancer Res 2009; 69(6):2358-64]. In addition, as discussed below, internalization is typically intended to release the agent from the antibody. This release then allows free agent to traffic out of the cell and to interact with normal cells that neighbor the diseased cells, resulting in undesired toxicity. The EDCs of the invention do not require internalization and in most cases are typically not internalized, which alleviates many of the problems associated with ADC approaches that require internalization.

A second difficulty associated with prior ADC approaches is that the drug of the ADC had to be released from the antibody before or after entering the cell to activate the drug or allow it entry into the cell. Approaches to allow selective release have included incorporating specific peptide sequences that are cleaved by cell specific peptidases (see US Pat. App. 20090220529) or contain environmentally sensitive linkages such that release or activation occurs near the cell membrane, within the cell membrane, or inside the cell cytosol or endosomal compartments. Certain cell types have been found to internalize the ADC into compartments which may not release the drug in active form, thus limiting the scope of the particular ADC [Cancer Res 2009; 69(6):2358-64]. The EDCs of the invention do not require internalization and in most cases are not internalized, which alleviates many of the problems associated with ADC approaches that require internalization dependent drug-antibody separation.

A third difficulty associated with prior ADC approaches is that the drug of the ADC had to be generally stable and not activated until entering or coming into close proximity with the cell. This requirement was important to ensure that release of the therapeutic agent from the antibody did not occur prior to the interaction of the antibodies with their targets, which could lead to increased toxicity. Keeping the drug conjugated to the antibody was also important to maintain the efficacy of the ADC when not bound to its target cell and to keep unconjugated antibody from masking the target site from the active ADCs. The majority of publications on the ADC approach discuss methods to solve these problems. The EDCs of the invention do not require the agent release from the EDC to be effective, which alleviates many of the problems associated with ADC approaches that require drug-antibody separation.

In contrast to prior approaches, the present invention provides highly specific EDCs that do not require cellular internalization and do not impose technically difficult constraints on the linker. The EDCs of the invention therefore do not require that the targeting moiety facilitate internalization; thus, the EDCs of the invention can utilize targeting moieties other than antibodies, including but not limited to aptamers. The EDCs of the invention also require that the agent and the antibody remain intact for maximal specificity and activity. Because the antibodies or targeting moieties of the invention target extracellular antigens and internalization is not required for efficacy, lysosomal enzymatic degradation is neither required nor beneficial. Because the linkers used in the EDCs of the invention are stable or even non-cleavable, premature release of the drug from the EDC is minimized and linker design is more flexible and is less complicated.

The EDCs of the invention are more selective and/or less toxic than the drug they contain. In the EDCs of the invention, the targeting moiety and/or linker can effectively prevent or dramatically reduce the therapeutic effect of the drug until the targeting moiety binds to its target. Thus the EDCs of the invention are primarily active only when the targeting moiety is bound to its target and in close proximity to the therapeutic agent's target and when the EDC is intact. Taken together, these characteristics allow for more specific and less toxic EDCs. The EDCs of the invention are more selective because both agent and antibody target sites need to be not only present, but also present in close proximity to one another. The EDCs of the invention are less toxic because the agent is linked through a stable linker and only fully active when attached to the targeting moiety. Thus, the EDCs of the invention are largely inactive when the targeting moiety is not bound to its target. The EDCs of the invention are also largely inactive when the targeting moiety is bound to its target but the targeting moiety's target is not in close proximity to the agent's target. In this case, the linker is not long enough to allow the drug to reach its target while attached to the targeting moiety.

The targeting moieties of the invention target extracellular antigens (targets). There are numerous extracellular antigens known to be accessible to antibodies. Many of these are disease cell selective, can be activated by therapeutic agents, and/or are in close proximity to targets of therapeutic agents.

Some of these extracellular antigens are found on cell surfaces. Over 60% of all approved drugs act on extracellular targets and/or targets on the cell surface. Illustrative examples of such targets, which may be exploited by the invention either as targets for targeting moieties or as targets for therapeutic agents include: (1) G-protein associated cell surface receptors (i.e., PAR, EP receptors, CXCR receptors, smoothened, LH receptor, TSH receptor, LPA receptors, secretin family of receptors, and rhodopsin family of receptors); (2) ion channels, most of which have multiple sub-families (i.e., the sodium channels, calcium channels, potassium channels, voltage-gated anion channels, and TRP family of ion channels); (3) nutrient transporters, most of which have multiple sub-families (i.e., glucose transporters, monocarboxylate transporters, and amino acid transporters); (4) receptor tyrosine kinases; (5) glutamate receptors; (6) nicotinic acetylcholine receptors; (7) toll like-receptors; (8) killer receptors; (9) CD molecules; (10) enzyme-linked receptors (i.e. receptor tyrosine kinases, tyrosine-kinase-associated receptors, receptor like tyrosine phosphatases, receptor serine/threonine kinases, receptor guanylyl cyclases and histidine-kinase-associated receptors) and (11) integrins.

Antibodies in the EDCs of the invention typically retain the antigen binding capability of their native, unconjugated counterparts. Thus, antibodies useful in the EDCs of the invention are capable of binding, preferably specifically, to antigens. Such antigens include, for example, tumor-associated antigens, cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody in an EDC of the invention is capable of binding may be a member of a subset of one of the above-mentioned categories, wherein the other subset(s) of said category comprise other molecules/antigens that have a distinct characteristic (with respect to the antigen of interest).

In one embodiment, the antibody in the EDC specifically binds to a dysadherin encoded by the FXYD5 gene and/or to the extracellular domain of dysadherin. In another embodiment, the antibody in the EDC binds to the extracellular domain of dysadherin and inhibits growth of tumor cells which overexpress dysadherin. In another embodiment, the antibody of the EDC may be a monoclonal antibody, e.g. a murine monoclonal antibody, a chimeric antibody, a human antibody or a humanized antibody. In another embodiment, the humanized antibody may be, for example, a humanized form of M53. In another embodiment, the antibody may be an antibody fragment, e.g. a Fab fragment. In another embodiment, the antibody of the EDC binds specifically to FXYD5. In another embodiment, the antibody of the EDC binds to or selectively binds to an epitope within the polypeptide represented by SEQ ID NO: 1. In another embodiment, the antibody of the EDC binds to a polypeptide represented by SEQ ID NO: 1. In another embodiment, the antibody of the EDC binds to FXYD5 or to an epitope within SEQ ID NO: 1 of FXYD5 and inhibits binding of FXYD5 to its receptor. In another embodiment, the antibody of the EDC binds to the antigen recognized by the M53 antibody. In another embodiment, the antibody of the EDC binds to the epitope on FXYD5 recognized by the M53 antibody. In another embodiment, the antibody of the EDC binds to the antigen recognized by the M53 antibody and competes for binding with the M53 antibody. In another embodiment, the antibody of the EDC binds selectively to cancer cells (e.g. lung cancer cells), but not to normal cells (e.g. normal lung cells).

Antibodies of the EDCs of the invention useful in the treatment of cancer include, but are not limited to, antibodies against cell surface receptors and tumor-associated antigens. Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Various methods have been employed to produce monoclonal antibodies (MAbs), and these methods are applicable to the production of antibodies for use in the EDCs of the invention and so are briefly reviewed below. Hybridoma technology, which refers to a cloned cell line that produces a single type of antibody, uses the cells of various species, including mice (murine), hamsters, rats, and humans. Other methods to prepare MAbs, including chimeric and humanized antibodies, employ genetic engineering, i.e. recombinant DNA techniques.

Polyclonal antibodies may be raised in animals by multiple subcutaneous (sc) or intraperitoneal (ip) injections of the relevant antigen and an adjuvant. Monoclonal antibodies are obtained from a population of substantially homogeneous antibodies, i.e., the individual antibodies comprising the population are identical except for possible naturally occurring mutations that may be present in minor amounts.

Human myeloma and mouse-human heteromyeloma cell lines also have been described for the production of human monoclonal antibodies (Kozbor, (1984) J. Immunol., 133: 3001, and Brodeur et al., Monoclonal Antibody Production Techniques and Applications, pp. 51-63 (Marcel Dekker, Inc., New York, 1987)). Culture medium in which hybridoma cells are growing is assayed for production of monoclonal antibodies directed against the antigen. Binding specificity of monoclonal antibodies produced by hybridoma cells may be determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al (1980) Anal. Biochem. 107:220.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells (US 2005/0048572; US 2004/0229310). Review articles on recombinant expression in bacteria of DNA encoding the antibody include Skerra et al (1993) Curr. Opinion in Immunol. 5:256-262 and Pluckthun (1992) Immunol. Revs. 130:151-188.

In a further embodiment, monoclonal antibodies or antibody fragments can be isolated from antibody phage libraries generated using the techniques described in McCafferty et al (1990) Nature 348:552-554; Clackson et al (1991) Nature 352:624-628; and Marks et al (1991) J. Mol. Biol., 222:581-597 describe the isolation of murine and human antibodies, respectively, using phage libraries. Subsequent publications describe the production of high affinity (nM range) human antibodies by chain shuffling (Marks et al (1992) Bio/Technology 10:779-783), as well as combinatorial infection and in vivo recombination as a strategy for constructing very large phage libraries (Waterhouse et al (1993) Nuc. Acids. Res. 21:2265-2266). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567); and Morrison et al (1984) Proc. Natl. Acad. Sci. USA 81:6851), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

A description follows as to exemplary techniques for the production of the antibodies (Ab), which can be used as the extracellular targeting moiety in the EDCs of the present invention. The production of antibodies will be illustrated with reference to anti-FXYD5 antibodies, but it will be apparent by those skilled in the art in view of the present disclosure that antibodies to other targets can be produced and modified in a similar manner.

The FXYD5 antigen to be used for production of antibodies may be, e.g., a soluble form of the extracellular domain of FXYD5 or a portion thereof, containing the desired epitope. Alternatively, cells expressing FXYD5 at their cell surface, e.g. NIH-3T3 cells transformed to overexpress FXYD5; or a carcinoma cell line such as A549 cells can be used to generate antibodies. Other forms of FXYD5 useful for generating antibodies will be apparent to those skilled in the art.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production (Jakobovits et al (1993) Proc. Natl. Acad. Sci. USA, 90:2551; Jakobovits et al (1993) Nature 362:255-258; Bruggermann et al (1993) Year in Immuno. 7:33; and U.S. Pat. No. 5,591,669; U.S. Pat. No. 5,589,369; U.S. Pat. No. 5,545,807).

Alternatively, phage display technology (McCafferty et al (1990) Nature 348:552-553) can be used to produce human antibodies and antibody fragments in vitro, from immunoglobulin variable (V) domain gene repertoires from unimmunized donors (Johnson, Kevin S. and Chiswell, David J. (1993) Current Opinion in Structural Biology 3:564-571). A repertoire of V genes from unimmunized human donors can be constructed and antibodies to a diverse array of antigens (including self-antigens) can be isolated essentially (Marks et al (1991) J. Mol. Biol. 222:581-597; Griffith et at (1993) EMBO J. 12:725-734; U.S. Pat. No. 5,565,332; U.S. Pat. No. 5,573,905). Human antibodies may also be generated by in vitro activated B cells (U.S. Pat. No. 5,567,610; U.S. Pat. No. 5,229,275). Human anti-ErbB2 antibodies are described (U.S. Pat. No. 5,772,997 and WO 97/00271.

Various techniques have been developed for the production of antibody fragments. Traditionally, these fragments were derived via proteolytic digestion of intact antibodies (see Morimoto et al (1992) Journal of Biochemical and Biophysical Methods 24:107-117; and Brennan et al (1985) Science 229:81). Antibody fragments can also be produced directly by recombinant host cells and the antibody phage libraries discussed above. Fab'-SH fragments can be directly recovered from E. coli and chemically coupled to form F(ab')$_2$ fragments (Carter et al (1992) Bio/Technology 10:163-167). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

Bispecific antibodies with binding specificities for at least two different epitopes (Millstein et al (1983), Nature 305: 537-539) may bind to two different epitopes of the FXYD5 protein or other antigens in close proximity. Purification methods for bispecific antibodies have been disclosed (WO 93/08829; Traunecker et al (1991) EMBO J. 10:3655-3659; WO 94/04690; Suresh et at (1986) Methods in Enzymology 121:210; U.S. Pat. No. 5,731,168). Bispecific antibodies can be produced using leucine zippers (Kostelny et al (1992) J. Immunol. 148(5):15471553), and single-chain Fv (sFv) dimers (Gruber et al (1994) J. Immunol. 152:5368). Techniques for generating bispecific antibodies from antibody fragments have also been described, such as using chemical linkage wherein intact antibodies are proteolytically cleaved to generate F(ab')$_2$ fragments (Brennan et at (1985) Science 229:81). Fab'-SH fragments can be recovered from E. coli and chemically coupled to form bispecific antibodies (Shalaby et al (1992) J. Exp. Med. 175:217-225. The "diabody" technology provides an alternative method for making bispecific antibody fragments (Hollinger et al (1993) Proc. Natl. Acad. Sci. USA 90:6444-6448).

Antibodies with more than two valencies can be employed in various embodiments of the EDCs of the invention. Multivalent, "Octopus" antibodies with three or more antigen binding sites and two or more variable domains can be readily produced by recombinant expression of nucleic acid encoding the polypeptide chains of the antibody (US 2002/0004586; WO 01/77342). For example, trispecific antibodies can be prepared (Tutt et al (1991) J. Immunol. 147:60).

Amino acid sequence modification(s) of antibodies are contemplated by the invention. For example, mutants and various isoforms of antibodies which bind to tumor-associated antigens are contemplated to improve the binding affinity and/or other biological properties of the antibody. Amino acid sequence variants of an antibody are prepared by introducing appropriate nucleotide changes into the nucleic acid encoding the antibody, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter posttranslational processes of the antibody, such as changing the number or position of glycosylation sites.

A useful method for identification of certain residues or regions of the antibody that are preferred locations for mutagenesis is "alanine scanning mutagenesis" (Cunningham and Wells (1989) Science 244:1081-1085) where an amino acid residue, or group of target residues, are identified (e.g., charged residues such as arg, asp, his, lys, and glu) and replaced by a neutral or negatively charged amino acid, such as alanine or polyalanine, to optimize the interaction of the amino acids with antigen. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-FXYD5 antibody with an N-terminal methionyl residue or the antibody fused to a cytotoxic polypeptide. Other insertional variants of the anti-FXYD5 antibody molecule include the fusion to the N- or C-terminus of the anti-FXYD5 antibody to an enzyme (e.g. for ADEPT: Tietze et al (2003) Current Pharm. Design 9:2155-2175) or a polypeptide which increases the serum half-life of the antibody, such as an albumin-binding peptide.

Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827). A series of albumin binding peptides were identified by phage display screening (Dennis et al (2002) "Albumin Binding As A General Strategy For Improving The Pharmacokinetics Of Proteins" J Biol. Chem. 277:35035-35043; WO 01/45746). Compounds useful in the EDCs of the invention include ABP sequences taught by: (i) Dennis et al (2002) J Biol. Chem. 277:35035-35043 at Tables III and IV, page 35038; and (ii) US 20040001827 at [0076] SEQ ID NOS: 9-22; and (iii) WO 01/45746 at pages 12-13, SEQ ID NOS: z1-z14, all of which are incorporated herein by reference.

The amino acid sequence is usually altered by altering the underlying nucleic acid sequence. Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (US 2003/0190311, U.S. Pat. No. 6,821,505; U.S. Pat. No. 6,165,745; U.S. Pat. No. 5,624,821; U.S. Pat. No. 5,648,260; U.S. Pat. No. 6,165,745; U.S. Pat. No. 5,834,597).

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), or the extent of glycosylation.

Antibodies may be glycosylated at conserved positions (N-linked or 0-linked) in their constant regions (Hse et al (1997) J. Biol. Chem. 272:9062-9070; Jefferis and Lund, (1997) Chem. Immunol. 65:111-128; Wright and Morrison, (1997) TibTECH 15:26-32). The oligosaccharide side chains of the immunoglobulins affect the protein's function (Boyd et al (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner (1996) Current Opin. Biotech. 7:409-416). Oligosaccharides may also serve to target a given glycoprotein to certain molecules based upon specific recognition structures (Maihotra et al (1995) Nature Med. 1:237-243; Umana et al (1999) Nature Biotech. 17:176-180). Removal of the oligosaccharides may optimize antigen binding and other properties of the antibody (Boyd et al (1996) Mol. Immunol. 32:1311-1318).

Factors which affect glycosylation during recombinant production of antibodies include growth mode, media formulation, culture density, oxygenation, pH, purification schemes and the like (U.S. Pat. No. 5,047,335; U.S. Pat. No. 5,510,261; U.S. Pat. No. 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-δ-galactosidase), elimination using harsh alkaline environment to release mainly 0-linked structures, and chemical methods using anhydrous hydrazine to release both N- and 0-linked oligosaccharides.

Some of these targets of antibodies or other targeting moieties of the EDCs of the invention have multiple subunits, isoforms and/or glycosylation patterns which determine their location in or on cells. Their presentation can depend on cell type, location on the cell, location of the cell, and/or physiological and pathological conditions. For example, the type of beta subunit (1 vs. 2) found in the Na/K-ATPase complex and its glycosylation pattern differ from cell type to cell type (see Proteomics 2008; 8(16):3236-56, and Am J Physiol 1997; 272(1 Pt 1):L85-94, incorporated herein by reference). In addition, many extracellular targets are slightly different or over expressed in diseased tissues or in the circulatory structure surrounding diseased tissue. For example, aberrant glycosylation is a hallmark of cancer and includes alterations in the carbohydrate content of glycoproteins, glycolipids, and glycosaminoglycans (see Anticancer Agents Med Chem 2008; 8(1):2-21, incorporated herein by reference). Specifically, there is an abundance of evidence that beta-1,6-GlcNAc-branching of N-glycans contributes directly to cancer progression (see Biochim Biophys Acta 1999; 1473(1): 21-34, incorporated herein by reference). The glycosylation patterns of the Na/K-ATPase membrane bound ion pump are believed to have evolved to serve cell specific regulatory requirements and are aberrantly glycosylated in a number of cancer cells. Gamma subunit isoform 5 of the Na/K-ATPase membrane bound ion pump complex is a glycosylated membrane protein (also called dysadherin or FXYD5) that has been shown to promote experimental cancer metastasis and is an independent prognostic indicator of metastasis and survival for many different types of human cancer [see Nam et. al. Cancer Lett. 255(2) 161-9 (2007)]. Accordingly, each of these targets present antigens that can be targeted by the targeting moiety of the EDCs of the invention.

A somatic mutation in the chaperone Cosmc can lead to the creation of new glycopeptide epitopes to which cancer specific antibodies for use in the EDCs of the invention can be raised (see Schietinger, A. et. al. Science 314(5797) 304-8 (2006), incorporated herein by reference). Antibodies have been generated that recognize these differences in glycosylation. Two papers describe how to produce specific antibodies to aberrantly glycosylated cell surface glycans (see Cancer Immunol Immunother 2006; 55(11):1337-47, and Cancer Res 2009; 69(5):2018-25). However, generating high affinity antibodies to sugars alone can be difficult. To overcome the problem of immune tolerance to tumor-associated carbohydrate antigens, non-naturally occurring antigenic sugars can be fed to cells, creating new glycosylation motifs to which high affinity antibodies can be generated (see Bioorg. Med. Chem. 15 (2007) 7561-7567). Antibodies generated to these non-naturally occurring sugars in conjunction with the proteins they decorate lead to very specific disease targeting antibodies and are useful in various embodiments of the EDCs of the invention.

Antibodies have also been generated to targets that are over-expressed in diseased tissue, and such antibodies are useful in the EDCs of the invention. For cancer, these antigens are typically named tumor-associated antigens and represent a group of normal non-mutant molecules. Illustrative examples include the EGFR receptor (Clin Cancer Res 2001; 7: 2958-70, incorporated herein by reference), the gamma 5 subunit of the Na/K-ATPase (Cancer Lett. 2007 Oct. 8; 255 (2): 161-169, incorporated herein by reference), and MUCIN (Cancer Immunol Immunother 2006; 55(11):1337-47, incorporated herein by reference). Therefore, in one embodiment, the antibody in the EDC of the invention is an antibody that binds to an extracellular target and has been approved for human administration by the FDA, including but not limited to Erbitux.

Antibodies have also been generated to targets that are over-expressed on cancer cells that metastasize, and such antibodies are useful in the EDCs of the invention. Metastatic cells have the ability to migrate to other tissues or organs thus spreading the cancer. Such an example of antibodies that target metastasizing cancer cell types is the antibody NCC-M53 (M53), which recognizes the extracellular target called dysadherin or FXYD5 [Cancer Lett. 2007 Oct. 8; 255(2): 161-169]. Studies suggest a role for dysadherin specifically in the metastatic process, and this extracellular target tends to be expressed where the cell-cell contact is loose, or in dissociated cells. Over-expression of dysadherin has been found to be significantly associated with metastasis and/or poor prognosis. It is thought that some primary tumors can regress completely, but leave their metastases behind. Currently, if a cancer is found to have spread to other tissues and organs, the patient's likelihood of survival significantly decreases. The treatment options currently available are rarely able to cure metastatic cancers. Thus, in one embodiment the EDCs of the invention comprise the antibody NCC-M53 or any other antibody that binds specifically to dysadherin.

Antibodies have also been generated to gangliosides, located in lipid rafts and on certain diseased cell types, and such antibodies are useful in the EDCs of the invention. Specifically antibodies raised to gangliosides have shown the ability to kill cancer cells [see Oncology Research, Vol. 12, pp. 173-179, 2000; J Biol. Chem. Vol. 280, No. 33, Issue of August 19, pp. 29828-29836, 2005; and Cancer Letters 281 (2009) 171-182]. Because certain gangliosides are abundantly expressed on the surface of tumor cells and are found in certain cell surface compartments, like lipid rafts, drugs can be attached to ganglioside specific antibodies to make EDCs of the invention.

In addition to the antigen target changes or over-expressed targets that occur in diseased tissues, there exist tumor specific antigens, and antibodies to these antigens can be used in the EDCs of the invention. These molecules are usually found on the cell membrane, and can be targets for antitumor agents. Many such antigens are mutants of a corresponding protein found on normal cells/tissue. Many of these types of antigens are unique to the individual or small subsets of tumors and thus require personalized therapy. The EDCs of the invention include EDCs made with personalized antibodies to these types of antigens.

The EDCs of the invention include EDCs in which, unlike the embodiments discussed immediately above, the targeting moiety does not target mutant proteins, over-expressed targets, tumor-associated antigens, or tumor specific antigens but targets that are present on normal cells of specific types. Here, the increased specificity of the targeting moiety alone suffices to create advantages. For example, there are drugs that act on many or all GLUT-transporters, yet are non-specific with regards to cell type or GLUT-transporter type. Because of this, GLUT-transporter specific drugs that target one cell type over another have been difficult to create. The present invention provides EDCs in which the targeting moiety recognizes a specific GLUT transporter(s) that exists only on the targeted cell type while the drug attached acts more universally (i.e., the same agent then could be attached to different antibodies making different EDCs with different therapeutic effects). This allows the same agent (drug) to be linked to various antibodies each with varying specificity to provide EDCs of the invention.

Beyond the targeting aspect, the targeting moiety portion of the EDC of the invention can bring other advantages. For example, the targeting moiety can facilitate transport across the blood brain barrier (for example, antibodies that target transferring receptor can facilitate this transport); the targeting moiety can increase the in vivo half-life of a therapeutic agent (three IgG subclasses have half-lives of about 20 days in humans); and/or the targeting moiety can increase the solubility of the agent in aqueous solutions such as the circulatory structure or pharmaceutical diluents.

In various embodiments of the EDC of the invention, the targeting moiety on the EDC of the invention can act to: (i) keep the agents of the invention near or on the target for a prolonged period of time (depending on its binding affinity), (ii) prevent or retard degradation by lysosomal enzymes, because a non-internalizing targeting moiety is not internalized into the cells by a receptor/antigen type of endocytosis and so does not reach the lysosomal system, and (iii) prevent uptake intracellularly by fluid phase endocytosis in a manner dependent linearly on its extracellular concentration. A non-internalizing characteristic of a targeting moiety can be determined experimentally by one skilled in the art. By way of example, non-internalizing antibodies are those that interact with antigens and epitopes present at the surface of target tissue extracellular constituents such as those of the extracellular matrix and do not enter the lysosome where they can become degraded.

The antibodies in the EDCs of the invention can include various monoclonal antibodies, polyclonal antibodies, modified antibodies, chimeric antibodies or improved antibodies within the scope of the definitions provided above. For example, modern alternative strategies now allow for the production of fully humanized antibodies to reduce the immunogenicity of the antibody. In addition, smaller antibody fragments can be engineered, including antigen binding Fabs, Fvs, scFv, and minibodies, and the antibody can also be enhanced to increase the antibody's affinity, stability, and expression level (see Nat Med. 2003 Jan.; 9(1):129-34).

In an alternative embodiment of the invention, the targeting moiety of the EDC of the invention is not an antibody but is instead a peptide or protein or peptidomimetic that is the functional equivalent, in terms of targeting, of an antibody. For example and without limitation, the antibody can be replaced by any of a number of small and robust non-immunoglobulin "scaffolds" that can be equipped with prescribed binding functions using the methods of combinatorial protein design. Such scaffolds are described in various reviews (see, e.g. "Engineered protein scaffolds as next-generation antibody therapeutics" in Curr Opin Chem Biol. 2009 Jun.; 13(3): 245-55 and "Engineered affinity proteins for tumour-targeting applications" in Biotechnol Appl Biochem. 2009 May; 53(Pt 1):1-29).

In another alternative embodiment of the invention, the targeting moiety of the EDC of the invention is not an antibody but is instead a DNA, RNA, or oligonucleotide mimetic that is the functional equivalent, in terms of targeting, of an antibody. For example, SELEX methods can be used to identify DNA or RNA or modifications thereof with prescribed binding functions. Aptamers are polymers of RNA or DNA oligonucleotides or modifications thereof that are isolated by the systematic evolution of ligands like the exponential enrichment SELEX process (see Hicke and Stephens, 2000, "Escort Aptamers: A Delivery Service for Diagnosis and Therapy," J. Clin. Invest., 106(8), pp. 923-928).

In another alternative embodiment of the invention, the targeting moiety of the EDC of the invention is not an antibody but is instead ganglioside, which acts as the functional equivalent, in terms of targeting, of an antibody in this embodiment. Gangliosides comprise a family of amphipathic molecules that contain a ceramide moiety as a lipophilic anchor embedded in the outer leaflet of plasma membranes and a sialo-oligosaccharide residue exposed towards the extracellular space. Gangliosides can thus be used to target drugs to the cell surface and, particularly, to lipid rafts where important drug targets are located. Molecules such as biotin and digitoxigenin have been attached to gangliosides to observe the distribution of gangliosides [see J Histochemistry & Cytochemistry 47(8): 1005-1014, 1999; and Chemistry and Physics of Lipids 86 (1997) 37-50].

Typically, the targeting moiety (or other binding or targeting moiety) will be purified to greater than 95% by weight (as determined, for example, by the Lowry method), and often to more than 99% by weight prior to use in forming an EDC of the invention. Ordinarily, the targeting moiety will be prepared by at least one purification step. Once a targeting moiety of interest is available, it can be linked to a therapeutic agent by any of a variety of linkers and linker technologies, as discussed in the following section.

Illustrative targeting moieties for EDCs of the invention include antibodies to FXYD5 such as NCC-M53 or a humanized form of M53. Additional targeting moieties for EDCs of the invention include antibodies specific to CD147 such as EMMPRIN or basigin, antibodies specific to integrins such as MEDI-522 also known as Vitaxin, ReoPro, Tysabri, and Ambegrin, and antibodies that have high affinities to extracellular epitopes of extracellular targets. Thus, there is a wide variety of targets and targeting moieties that can be used to make EDCs of the invention. Targeting moieties of particular interest are those that target disease specific extracellular targets that are located in close proximity to agent targets. The EDCs of the present invention include EDCs comprising agents that are not specific enough, as single or stand-alone agents, to be used for therapeutic purposes. Such agents now find therapeutic application as agents in EDCs of the invention.

Figure 3:
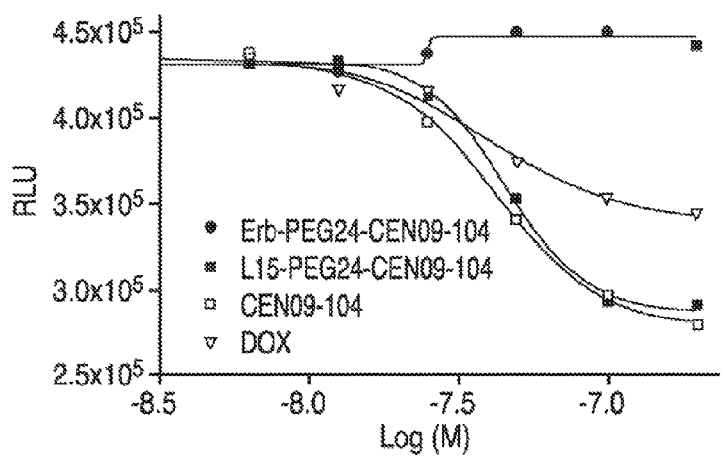
FIG. 3 shows the A549 cytotoxic testing at concentrations indicated. Two conjugates, the free agent and doxorubicin (Dox) were used. CEN09-104 is the free drug not attached to an antibody. Dox=doxorubicin positive control. RLU=Relative Luminescent Units. See Example 4.
Figure 4:
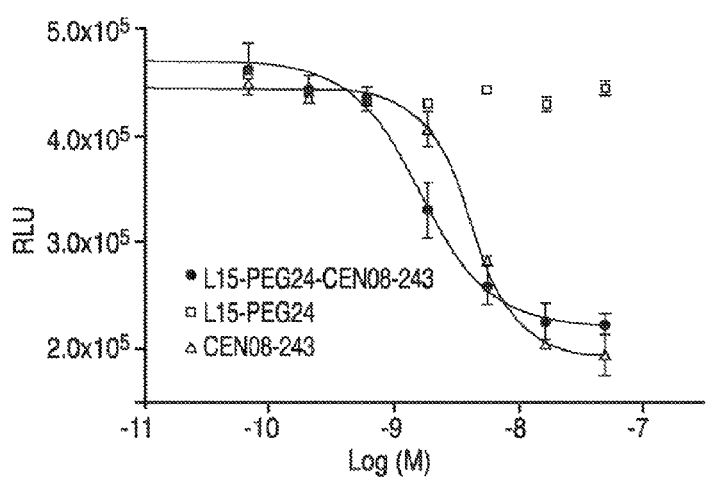
FIG. 4 shows the A549 cytotoxic testing at concentrations indicated. One conjugate, the free agent and a linker attached antibody without agent (L15-) were used. See Example 4.

Targets of the targeting moieties include, without limitation, tumor-associated antigens, including but not limited to BMPR1B (bone morphogenetic protein receptor-type IB, Genbank accession no. NM-001203) ten Dijke, P., et al Science 264 (5155):101-104 (1994), Oncogene 14 (11):1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4) NP-001194 bone morphogenetic protein receptor, type IB/pid=NP.sub.-001194.1-Crossreferences: MIM:603248, NP.sub.-001194.1; AY065994(2) E16 (LAT1, SLC7A5, Genbank accession no. NM.sub.-003486) Biochem. Biophys. Res. Commun. 255 (2), 283-288 (1999), Nature 395 (6699):288-291 (1998), Gaugitsch, H. W., et al (1992) J. Biol. Chem. 267 (16): 1126711273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136);

US2003224454 (FIG. 3); W02003025138 (claim 12; Page 150); US 20050107595; US 20050106644; NP.sub.-003477 solute carrier family 7 (cationic amino acid transporter, y+system), member 5/pid=NP.sub.-003477.3-*Homo sapiens* Cross-references: MIM:600182, NP.sub.-003477.3; NM.sub.-015923, NM.sub.-003486.sub.-1.

Figure 2:
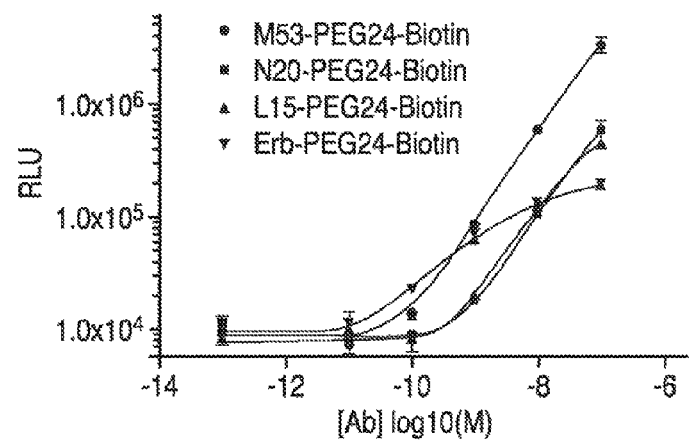
FIG. 2 shows antibody-linker-biotin binding to A549 cells after their addition at the indicated concentrations. See Example 3.

Another illustrative target for the targeting moieties of the EDCs of the invention is STEAP1 (six transmembrane epithelial antigen of prostate, Genbank accession no. NM.sub.-012449) Cancer Res. 61 (15), 5857-5860 (2001), Hubert, R. S., et al (1999) Proc. Natl. Acad. Sci. U.S.A. 96 (25):14523-14528); W02004065577 (claim 6); W02004027049 (FIG. 1L); EP1394274 (Example 11); W02004016225 (claim 2); W02003042661 (claim 12); US2003157089 (Example 5); US2003185830 (Example 5); US2003064397 (FIG. 2); W0200289747 (Example 5; Page 618619); W02003022995 (Example 9; FIG. 13A, Example 53; Page 173, Example 2; FIG. 2A); NP.sub.-036581 six transmembrane epithelial antigen of the prostate. Cross-references: MIM:604415 NP.sub.-036581.1; NM.sub.-012449.sub.-1.

Another illustrative target for the targeting moieties of the EDCs of the invention is 0772P (CA125, MUC16, Genbank accession no. AF361486) J. Biol. Chem. 276 (29):27371-27375 (2001)); W02004045553 (claim 14); W0200292836 (claim 6; FIG. 12); W0200283866 (claim 15; Page 116-121); US2003124140 (Example 16); US2003091580 (claim 6); W0200206317 (claim 6; Page 400-408); Cross-references: GI:34501467; AAK74120.3; AF361486.sub.-1.

Another illustrative target for the targeting moieties of the EDCs of the invention is MPF (MPF, MSLN, SMR, megakaryocyte potentiating factor, mesothelin, Genbank accession no. NM.sub.-005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); W02003101283 (claim 14); (W02002102235 (claim 13; Page 287-288); W02002101075 (claim 4; Page 308-309); W0200271928 (Page 320-321); W09410312 (Page 52-57); Cross-references: MIM:601051, NP.sub.-005814.2; NM.sub.-005823.sub.-1.

Another illustrative target for the targeting moieties of the EDCs of the invention is Napi3b (NAPI-3B, NPTIIb, SLC34A2, solute carrier family 34 (sodium phosphate), member 2, type II sodium-dependent phosphate transporter 3b, Genbank accession no. NM.sub.-006424) J. Biol. Chem. 277 (22):19665-19672 (2002), Genomics 62 (2):281-284 (1999), Feild, J. A., et al (1999) Biochem. Biophys. Res. Commun. 258 (3):578-582); W02004022778 (claim 2); EP1394274 (Example 11); W02002102235 (claim 13; Page 326); EP875569 (claim 1; Page 17-19); W0200157188 (claim 20; Page 329); W02004032842 (Example IV); W0200175177 (claim 24; Page 139-140); Cross-references: MIM:604217, NP.sub.-006415.1; NM.sub.-006424.sub.-1.

Another illustrative target for the targeting moieties of the EDCs of the invention is Sema 5b (FU10372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et at (2000) DNA Res. 7 (2):143-150); W02004000997 (claim 1); W02003003984 (claim 1); W0200206339 (claim 1; Page 50); W0200188133 (claim 1; Page 41-43, 48-58); W02003054152 (claim 20); W02003101400 (claim 11); Accession: Q9P283; EMBL; AB040878; BAA95969.1. Genew; HGNC:10737.

Another illustrative target for the targeting moieties of the EDCs of the invention is PSCA hlg (2700050C12Rik, C530008016Rik, RIKEN cDNA 2700050012, RIKEN cDNA 2700050012 gene, Genbank accession no. AY358628); Ross et al (2002) Cancer Res. 62:2546-2553; US2003129192 (claim 2); US2004044180 (claim 12); US2004044179 (claim 11); US2003096961 (claim 11); US2003232056 (Example 5); W02003105758 (claim 12); US2003206918 (Example 5); EP1347046 claim 1); W02003025148 (claim 20); Cross-references: GI:37182378; AAQ88991.1; AY358628.sub.-1.

Figure 6:
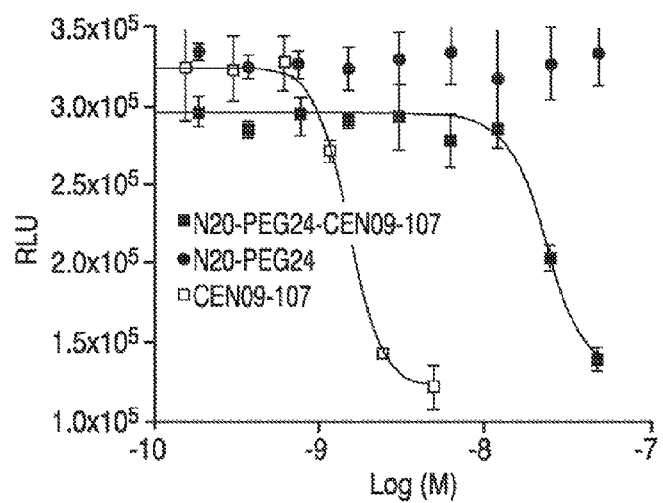
FIG. 6 shows the A549 cytotoxic testing at concentrations indicated. One conjugate, the free agent and a linker attached antibody without agent (N20-) were used. See Example 4.

Another illustrative target for the targeting moieties of the EDCs of the invention is ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et at J. Biol. Chem. 268, 3463-3470, 1993; Sakamoto A., Yanagisawa M., et al Biochem. Biophys. Res. Commun. 178, 656663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et at Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et at Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et at Hum. Genet. 103, 145-148, 1998; Fuchs S., et al Mol. Med. 7, 115-124, 2001; Pingault V., et al (2002) Hum. Genet. 111, 198-206; W02004045516 (claim 1); W02004048938 (Example 2); W02004040000 (claim 151); W02003087768 (claim 1); W02003016475 (claim 1); W02003016475 (claim 1); W0200261087 (FIG. 1); W02003016494 (FIG. 6); W02003025138 (claim 12; Page 144); W0200198351 (claim 1; Page 124-125); EP522868 (claim 8; FIG. 2); W0200177172 (claim 1; Page 297-299); US2003109676; U.S. Pat. No. 6,518,404 (FIG. 3); U.S. Pat. No. 5,773,223 (Claim Ia; Col 31-34); W02004001004; (10) MSG783 (RNF124, hypothetical protein FU20315, Genbank accession no. NM.sub.-017763); W02003104275 (claim 1); W02004046342 (Example 2); W02003042661 (claim 12); W02003083074 (claim 14; Page 61); W02003018621 (claim 1); W02003024392 (claim 2; FIG. 93); W0200166689 (Example 6); Cross-references: LocusID:54894; NP.sub.-060233.2, NM.sub.-017763.sub.-1.

Figure 10:
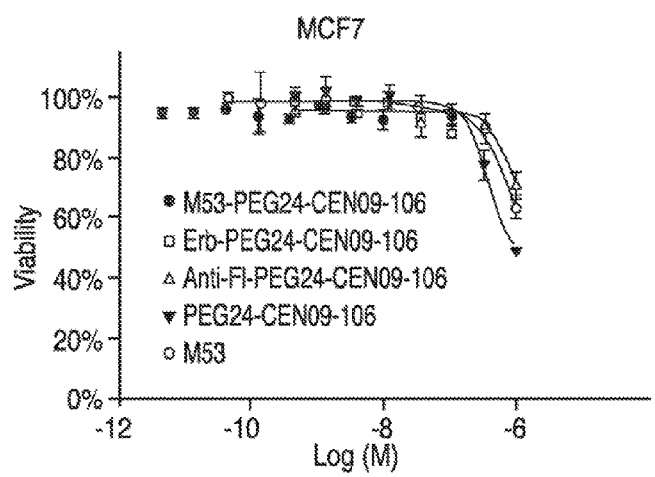
FIG. 10 shows the MCF7 cytotoxic testing using the agents at concentrations indicated. Three conjugates, the free linker-agent and antibody M53 without agent or linker were tested. See Example 5.

Another illustrative target for the targeting moieties of the EDCs of the invention is STEAP2 (HGNC.sub.-8639, IPCA-1, PCANAP1, STAMP!, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); W02003087306; US2003064397 (claim 1; FIG. 1); W0200272596 (claim 13; Page 54-55); W0200172962 (claim 1; FIG. 4B); W02003104270 (claim 11); W02003104270 (claim 16); US2004005598 (claim 22); W02003042661 (claim 12); US2003060612 (claim 12; FIG. 10); W0200226822 (claim 23; FIG. 2); W0200216429 (claim 12; FIG. 10); Cross-references: GI:22655488; AAN04080.1; AF455138.sub.-1.

Another illustrative target for the targeting moieties of the EDCs of the invention is TrpM4 (BR22450, FU20041, TRPM4, TRPM4B, transient receptor potential cation channel, subfamily M, member 4, Genbank accession no.

NM.sub.-017636) Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (claim 4); W0200040614 (claim 14; Page 100-103); W0200210382 (claim 1; FIG. 9A); W02003042661 (claim 12); W0200230268 (claim 27; Page 391); US2003219806 (claim 4); W0200162794 (claim 14; FIG. 1A-D); Cross-references: MIM:606936, NP.sub.-060106.2; NM.sub.-017636.sub.-1.

Another illustrative target for the targeting moieties of the EDCs of the invention is CRIPTO (CR, CR1, CRGF, CRIPTO, TDGF1, teratocarcinoma-derived growth factor, Genbank accession no. NP.sub.-003203 or NM.sub.-003212) Ciccodicola, A., et at EMBO J. 8 (7):19871991 (1989), Am. J. Hum. Genet. 49 (3):555-565 (1991)); US2003224411 (claim 1); W02003083041 (Example 1); W02003034984 (claim 12); W0200288170 (claim 2; Page 52-53); W02003024392 (claim 2; FIG. 58); W0200216413 (claim 1; Page 94-95, 105); W0200222808 (claim 2; FIG. 1); U.S. Pat. No. 5,854, 399 (Example 2; Col 17-18); U.S. Pat. No. 5,792,616 (FIG. 2); Cross-references: MIM:187395, NP.sub.-003203.1; NM.sub.-003212.sub.-1.

Figure 9:
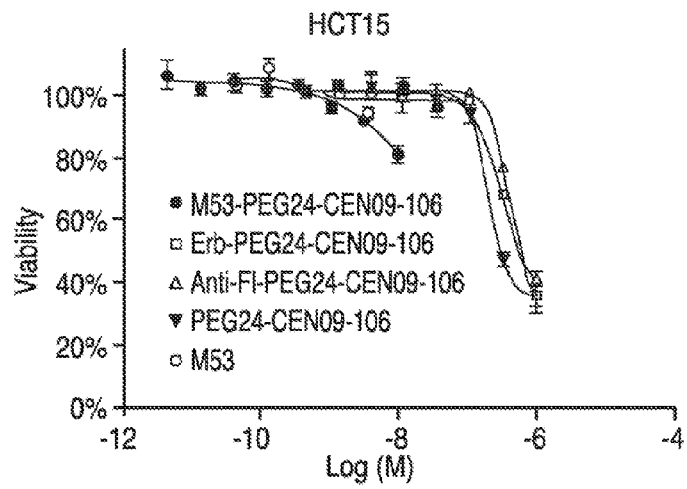
FIG. 9 shows the HCT15 cytotoxic testing using the agents at concentrations indicated. Three conjugates, the free linker-agent and antibody M53 without agent or linker were tested. See Example 5.

Another illustrative target for the targeting moieties of the EDCs of the invention is CD21 (CR2 (Complement receptor 2) or C3DR(C3d/Epstein Barr virus receptor) or Hs.73792 Genbank accession no. M26004) Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 91949198, 1987; Bare! M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; W02004045520 (Example 4); US2004005538 (Example 1); W02003062401 (claim 9); W02004045520 (Example 4); W09102536 (FIGS. 9.1-9.9); W02004020595 (claim 1); Accession: P20023; Q13866; Q14212; EMBL; M26004; AAA35786.1.

Another illustrative target for the targeting moieties of the EDCs of the invention is CD79b (CD79B, CD79.beta., IGb (immunoglobulin-associated beta), B29, Genbank accession no. NM.sub.-000626 or 11038674) Proc. Natl. Acad. Sci. U.S.A. (2003) 100 (7):4126-4131, Blood (2002) 100 (9): 3068-3076, Muller et al (1992) Eur. J. Immunol. 22 (6):1621-1625); W02004016225 (claim 2, FIG. 140); W02003087768, US2004101874 (claim 1, page 102); W02003062401 (claim 9); W0200278524 (Example 2); US2002150573 (claim 5, page 15); U.S. Pat. No. 5,644,033; W02003048202 (claim 1, pages 306 and 309); WO 99/558658, U.S. Pat. No. 6,534,482 (claim 13, FIG. 17A/B); W0200055351 (claim 11, pages 1145-1146); Cross-references: MIM:147245, NP.sub.-000617.1; NM.sub.-000626.sub.-1.

Another illustrative target for the targeting moieties of the EDCs of the invention is FcRH2 (IFGP4, IRTA4, SPAP1A (SH2 domain containing phosphatase anchor protein Ia), SPAP1B, SPAP1C, Genbank accession no. NM.sub.-030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; W02004016225 (claim 2); W02003077836; W0200138490 (claim 5; FIG. 18D-1-18D-2); W02003097803 (claim 12); W02003089624 (claim 25); Cross-references: MIM:606509, NP.sub.-110391.2; NM.sub.-030764.sub.-1.

Figure 7:
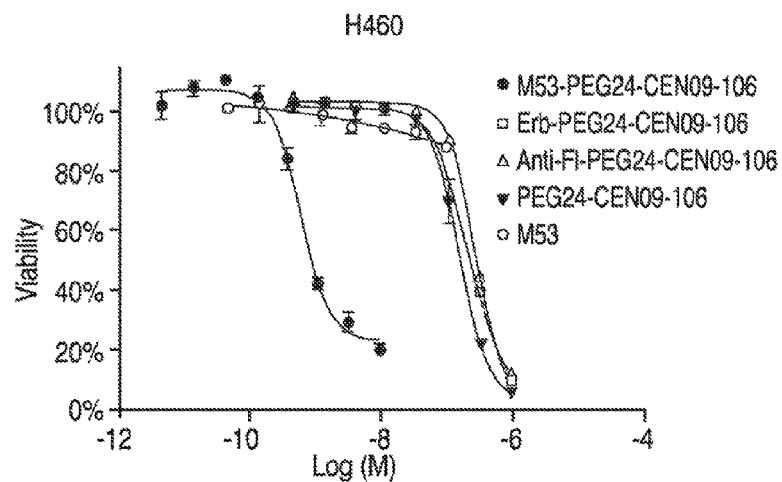
FIG. 7 shows the H460 cytotoxic testing using the agents at concentrations indicated. Three conjugates, the free linker-agent and antibody M53 without agent or linker were tested. See Examples 5 and 7.
Figure 11:
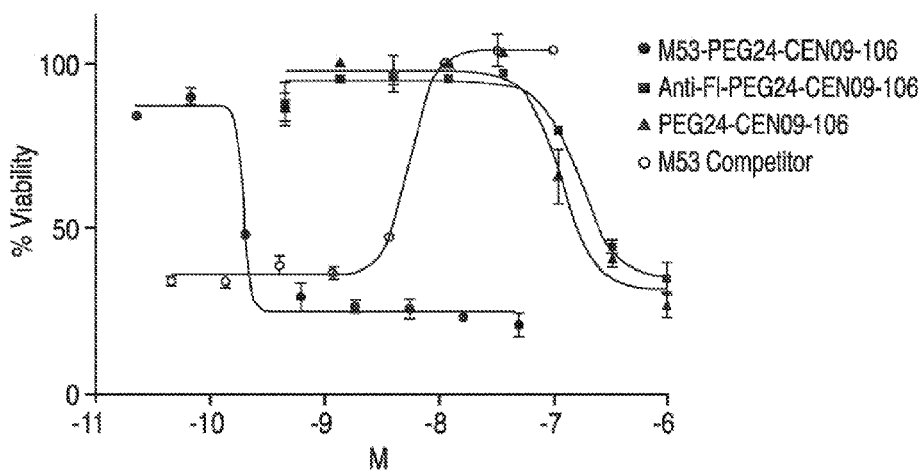
FIG. 11 shows A549 cell cytotoxic testing using the agents indicated. For the M53 Comp, M53-106 was held at 1 nM, and M53 was used at the concentrations indicated. All other agents were tested at the concentrations indicate on the M axis. See Example 8.

Another illustrative target for the targeting moieties of the EDCs of the invention is HER2 (ErbB2, Genbank accession no. M11730) Coussens L., et al Science (1985) 230(4730): 11321139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; W02004048938 (Example 2); W02004027049 (FIG. 11); W02004009622; W02003081210; W02003089904 (claim 9); W02003016475 (claim 1); US2003118592; W02003008537 (claim 1); W02003055439 (claim 29; FIG. 1A-B); W02003025228 (claim 37; FIG. 5C); W0200222636 (Example 13; Page 95-107); W0200212341 (claim 68; FIG. 7); W0200213847 (Page 71-74); W0200214503 (Page 114-117); W0200153463 (claim 2; Page 41-46); W0200141787 (Page 15); W0200044899 (claim 52; FIG. 7); W0200020579 (claim 3; FIG. 2); U.S. Pat. No. 5,869,445 (claim 3; Col 31-38); W09630514 (claim 2; Page 56-61); EP1439393 (claim 7); W02004043361 (claim 7); W02004022709; W0200100244 (Example 3; FIG. 4); Accession: PO4626; EMBL; M11767; AAA35808.1. EMBL; M11761; AAA35808.1.

Another illustrative target for the targeting moieties of the EDCs of the invention is NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; W02004063709; EP1439393 (claim 7); W02004044178 (Example 4); W02004031238; W02003042661 (claim 12); W0200278524 (Example 2); W0200286443 (claim 27; Page 427); W0200260317 (claim 2); Accession: P40199; Q14920; EMBL; M29541; AAA59915.1. EMBL; M18728.

Figure 8:
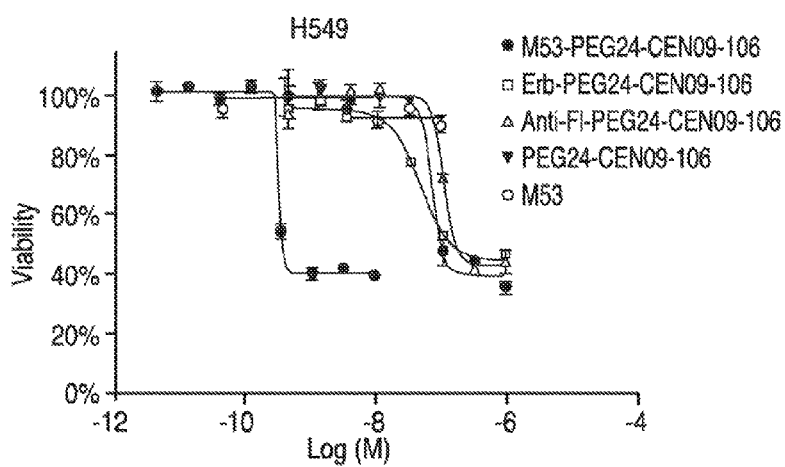
FIG. 8 shows the A549 cytotoxic testing using the agents at concentrations indicated. Three conjugates, the free linker-agent and antibody M53 without agent or linker were tested. See Example 5.

Another illustrative target for the targeting moieties of the EDCs of the invention is MDP (DPEP1, Genbank accession no. BC017023) Proc. Natl. Acad. Sci. U.S.A. 99 (26):16899-16903 (2002)); W02003016475 (claim 1); W0200264798 (claim 33; Page 85-87); JP05003790 (FIG. 6-8); W09946284 (FIG. 9); Cross-references: MIM:179780; AAH17023.1; BC017023.sub.-1.

Another illustrative target for the targeting moieties of the EDCs of the invention is IL2OR.alpha. (IL2ORa, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); W02003029262 (Page 74-75); W02003002717 (claim 2; Page 63); W0200222153 (Page 45-47); US2002042366 (Page 20-21); W0200146261 (Page 57-59); W0200146232 (Page 63-65); W09837193 (claim 1; Page 55-59); Accession: Q9UHF4; Q6UWA9; Q96SH8; EMBL; AF184971; AAF01320.1.

Another illustrative target for the targeting moieties of the EDCs of the invention is Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); W02003016475 (claim 1); W0200202634 (claim 1); (22) EphB2R (DRT, ERK, HekS, EPHT3, Tyro5, Genbank accession no. NM.sub.-004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); W02003042661 (claim 12); W0200053216 (claim 1; Page 41); W02004065576 (claim 1); W02004020583 (claim 9); W02003004529 (Page 128-132); W0200053216 (claim 1; Page 42); Cross-references: MIM: 600997, NP.sub.-004433.2; NM.sub.-004442.sub.-1.

Another illustrative target for the targeting moieties of the EDCs of the invention is ASLG659 (B7h, Genbank accession no. AX092328) US20040101899 (claim 2); W02003104399 (claim 11); W02004000221 (FIG. 3); US2003165504 (claim 1); US2003124140 (Example 2); US2003065143 (FIG. 60); W02002102235 (claim 13; Page 299); US2003091580 (Example 2); W0200210187 (claim 6; FIG. 10); W0200194641 (claim 12; FIG. 7b); W0200202624 (claim 13; FIG. 1A-1B); US2002034749 (claim 54; Page 45-46); W0200206317 (Example 2; Page 320-321, claim 34; Page 321-322); W0200271928 (Page 468-469); W0200202587 (Example 1; FIG. 1); W0200140269 (Example 3; Pages 190-192); W0200036107 (Example 2; Page 205-207); W02004053079 (claim 12); W02003004989 (claim 1); W0200271928 (Page 233-234, 452-453); WO 0116318; (24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; W02004022709; EP1394274 (Example 11); US2004018553 (claim 17); W02003008537 (claim 1); W0200281646 (claim 1; Page 164); W02003003906 (claim 10; Page 288); W0200140309 (Example 1; FIG. 17); U52001055751 (Example 1; FIG. 1b); W0200032752 (claim 18; FIG. 1); W09851805 (claim 17; Page 97); W09851824 (claim 10; Page 94); W09840403 (claim 2; FIG. 1B); Accession: 043653; EMBL; AF043498; AAC39607.1.

Another illustrative target for the targeting moieties of the EDCs of the invention is GEDA (Genbank accession No. AY260763); AAP14954 lipoma HMGIC fusion-partner-like protein/pid=AAP14954.1-*Homo sapiens* Species: *Homo sapiens* (human) W02003054152 (claim 20); W02003000842 (claim 1); W02003023013 (Example 3, claim 20); US2003194704 (claim 45); Cross-references: GI:30102449; AAP14954.1; AY260763.sub.-1.

Another illustrative target for the targeting moieties of the EDCs of the invention is BAFF-R (B cell-activating factor receptor, BLyS receptor 3, BR3, Genbank accession No. AF116456); BAFF receptor/pid=NP.sub.-443177.1-*Homo sapiens* Thompson, J. S., et al Science 293 (5537), 2108-2111 (2001); W02004058309; W02004011611; W02003045422 (Example; Page 32-33); W02003014294 (claim 35; FIG. 6B); W02003035846 (claim 70; Page 615-616); W0200294852 (Col 136-137); W0200238766 (claim 3; Page 133); W0200224909 (Example 3; FIG. 3); Cross-references: MIM: 606269, NP.sub.-443177.1; NM.sub.-052945.sub.-1; AF132600.

Another illustrative target for the targeting moieties of the EDCs of the invention is CD22 (B-cell receptor CD22-B isoform, BL-CAM, Lyb-8, Lyb8, SIGLEC-2, FU22814, Genbank accession No. AK026467); Wilson et al (1991) J. Exp. Med. 173:137-146; W02003072036 (claim 1; FIG. 1); Cross-references: MIM:107266, NP.sub.-001762.1; NM.sub.-001771.sub.-1.

Another illustrative target for the targeting moieties of the EDCs of the invention is CD79a (CD79A, CD79.alpha., immunoglobulin-associated alpha, a B cell-specific protein that covalently interacts with Ig beta (CD79B) and forms a complex on the surface with Ig M molecules, transduces a signal involved in B-cell differentiation) PROTEIN SEQUENCE Full mpggpgv . . . dvqlekp (1 . . . 226; 226 aa), pl: 4.84, MW: 25028 TM: 2 [P] Gene Chromosome: 19q13.2, Genbank accession No. NP.sub.-001774.10) W02003088808, US20030228319; W02003062401 (claim 9); US2002150573 (claim 4, pages 13-14); W09958658 (claim 13, FIG. 16); W09207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464.

Another illustrative target for the targeting moieties of the EDCs of the invention is CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) PROTEIN SEQUENCE Full mnypltl . . . atslttf (1.372; 372 aa), pl: 8.54 MW: 41959 TM: 7 [P] Gene Chromosome: 11 q23.3, Genbank accession No. NP.sub.-001707.1) W02004040000; W02004015426; US2003105292 (Example 2); U.S. Pat. No. 6,555,339 (Example 2); W0200261087 (FIG. 1); W0200157188 (claim 20, page 269); W0200172830 (pages 12-13); W0200022129 (Example 1, pages 152-153, Example 2, pages 254-256); W09928468 (claim 1, page 38); U.S. Pat. No. 5,440,021 (Example 2, col 49-52); W09428931 (pages 56-58); W09217497 (claim 7, FIG. 5); Dobner et al (1992) Eur. J. Immunol. 22:2795-2799; Barella et al (1995) Biochem. J. 309:773-779; (30) HLA-DOB (Beta subunit of MHC class II molecule (Ia antigen) that binds peptides and presents them to CD4+ T lymphocytes) PROTEIN SEQUENCE Full mgsg-wvp . . . vllpqsc (1.273; 273 aa, pl: 6.56 MW: 30820 TM: 1 [P] Gene Chromosome: 6p21.3, Genbank accession No. NP.sub.-002111.1) Tonnelle et al (1985) EMBO J. 4(11):28392847; Jonsson et al (1989) Immunogenetics 29(6):411-413; Beck et al (1992) J. Mol. Biol. 228:433-441; Strausberg et al (2002) Proc. Natl. Acad. Sci. USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; W09958658 (claim 13, FIG. 15); U.S. Pat. No. 6,153,408 (Col 35-38); U.S. Pat. No. 5,976,551 (col 168-170); U.S. Pat. No. 6,011,146 (col 145-146); 6sahara et al (1989) Immunogenetics 30(1):66-68; Larhammar et al (1985) J. Biol. Chem. 260(26):14111-14119.

Another illustrative target for the targeting moieties of the EDCs of the invention is P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) PROTEIN SEQUENCE Full mgqagck . . . lephrst (1.422; 422 aa), pl: 7.63, MW: 47206 TM: 1 [P] Gene Chromosome: 17p13.3, Genbank accession No. NP.sub.-002552.2) Le et al (1997) FEBS Lett. 418(1-2):195-199; W02004047749; W02003072035 (claim 10); Touchman et al (2000) Genome Res. 10:165-173; W0200222660 (claim 20); W02003093444 (claim 1); W02003087768 (claim 1); W02003029277 (page 82).

Another illustrative target for the targeting moieties of the EDCs of the invention is CD72 (B-cell differentiation antigen CD72, Lyb-2) PROTEIN SEQUENCE Full maeaity . . . tafrfpd (1.359; 359 aa), pl: 8.66, MW: 40225 TM: 1 [P] Gene Chromosome: 9p13.3, Genbank accession No. NP.sub.-001773.1) W02004042346 (claim 65); W02003026493 (pages 51-52, 57-58); W0200075655 (pages 105-106); Von Hoegen et al (1990) J. Immunol. 144(12):4870-4877; Strausberg et al (2002) Proc. Natl. Acad. Sci. USA 99:16899-16903.

Another illustrative target for the targeting moieties of the EDCs of the invention is LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis) PROTEIN SEQUENCE Full mafdvsc . . . rwkyqhi (1.661; 661 aa), pI: 6.20, MW: 74147 TM: [P] Gene Chromosome: 5q12, Genbank accession No. NP.sub.-005573.1) US2002193567; W09707198 (claim 11, pages 39-42); Miura et al (1996) Genomics 38(3):299-304; Miura et al (1998) Blood 92:2815-2822; W02003083047; W09744452 (claim 8, pages 57-61); W0200012130 (pages 24-26).

Another illustrative target for the targeting moieties of the EDCs of the invention is FcRH1 (Fc receptor-like protein 1, a putative receptor for the immunoglobulin Fc domain that contains C2 type Ig-like and ITAM domains, may have a role in B-lymphocyte differentiation) PROTEIN SEQUENCE Full mlprIII . . . vdyedam (1.429; 429 aa), pI: 5.28, MW: 46925 TM: 1 [P] Gene Chromosome: 1q21-1q22, Genbank accession No. NP.sub.-443170.1) W02003077836; W0200138490 (claim 6, FIG. 18E-1-18-E-2); Davis et al (2001) Proc. Natl. Acad. Sci. USA 98(17):9772-9777; W02003089624 (claim 8); EP1347046 (claim 1); W02003089624 (claim 7).

Another illustrative target for the targeting moieties of the EDCs of the invention is IRTA2 (Immunoglobulin superfamily receptor translocation associated 2, a putative immunoreceptor with possible roles in B cell development and lymphomagenesis; deregulation of the gene by translocation occurs in some B cell malignancies) PROTEIN SEQUENCE Full mllwvil . . . assaphr (1.977; 977 aa), pI: 6.88 MW: 106468 TM: 1 [P] Gene Chromosome: 1q21, Genbank accession No. Human:AF343662, AF343663, AF343664, AF343665, AF369794, AF397453, AK090423, AK090475, AL834187, AY358085; Mouse:AK089756, AY158090, AY506558, NP.sub.-112571.1 W02003024392 (claim 2, FIG. 97); Nakayama et al (2000) Biochem. Biophys. Res. Commun. 277(1):124-127; W02003077836; W0200138490 (claim 3, FIG. 18B-1-18B-2).

Another illustrative target for the targeting moieties of the EDCs of the invention is TENB2 (TMEFF2, tomoregulin, TPEF, HPP1, TR, putative transmembrane proteoglycan, related to the EGF/heregulin family of growth factors and follistatin) PROTEIN SEQUENCE Full mvlwesp . . . rastrli (1.374; 374 aa, NCBI Accession: AAD55776, AAF91397, AAG49451, NCBI RefSeq: NP.sub.-057276; NCBI Gene: 23671; OMIM: 605734; SwissProt Q9UIK5; Genbank accession No. AF179274; AY358907, CAF85723, CQ782436 W02004074320 (SEQ ID NO 810); JP2004113151 (SEQ ID NOS 2, 4, 8); W02003042661 (SEQ ID NO 580); W02003009814 (SEQ ID NO 411); EP1295944 (pages 69-70); W0200230268 (page 329); W0200190304 (SEQ ID NO 2706); US2004249130; US2004022727; W02004063355; US2004197325; US2003232350; US2004005563; US2003124579; U.S. Pat. No. 6,410,506; U.S. Pat. No. 66/420,061; Horie et al (2000) Genomics 67:146-152; Uchida et al (1999) Biochem. Biophys. Res. Commun. 266:593602; Liang et al (2000) Cancer Res. 60:4907-12; Glynne-Jones et al (2001) Int 1 Cancer. October 15; 94(2):178-84.

Thus, there are a wide variety of targets suitable for targeting by the targeting moieties of the EDCs of the invention. Antibody targeting moieties for many of these targets already exist or can be made by one of ordinary skill in the art in view of the disclosure herein.

III. LINKERS

To form an EDC of the invention, a therapeutic agent is coupled to the targeting moiety via a stable linker. The linker attaches the targeting moiety to an agent through one or more covalent bond(s), and, because stable linkers are required, the linker typically does not include a disulfide group or ester group. The linker is a bifunctional or multifunctional moiety which can be used to link one or more agents and a targeting moiety to form an EDC of the invention. EDCs can be conveniently prepared using a linker having reactive functionality for binding to the agent and to the targeting moiety. For example, a cysteine thiol, or an amine, e.g. N-terminus or amino acid side chain such as lysine, of an antibody type targeting moiety can form a bond with a functional group of a linker reagent, drug moiety or drug-linker reagent.

The linkers employed in the EDCs of the invention are stable. After administration, the EDC is stable and remains intact, i.e. the targeting moiety remains linked to the agent via the linker. The linkers are stable outside the target cell and remain uncleaved for efficacy. An effective linker will: (i) maintain the specific binding properties of the antibody; (ii) allow delivery of the conjugate or agent; (iii) remain stable and intact, i.e. not cleaved, for as long as the antibody and/or agent remains stable and intact; and (iv) maintain a cytotoxic, cell-killing effect or a cytostatic effect of the agent while the EDC is intact. Stability of the EDC may be measured by standard analytical techniques such as mass spectroscopy, HPLC, and the separation/analysis technique LC/MS.

Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

A stable linker forms a covalent bond between the therapeutic agent and a targeting moiety such that, when attached, the agent and targeting moiety can bind and act on their respective targets. While a stable linker can simply be a covalent bond formed between reactive sites on the targeting moiety and the agent, the stable linkers of the invention typically include a linker spacer group. To attach a targeting moiety to an agent through a linker, one utilizes complementary reactive groups. For example, accessible sulfhydryl groups on a targeting moiety, can react with active maleimide groups to form stable thioether linkages. An additional example is accessible amines on an agent can react with succinimide esters to form stable amide bonds. Bifunctional linkers which have maleimides on one end and succinimide esters on the other can be used in the invention to link the agent to the targeting moiety.

Thus, distinct chemical linkers (as opposed to a single covalent bond) are typically used in the EDCs of the invention. Linkers of this type are typically linear chains of atoms or polymers consisting of one or more "linker spacer groups" with two "ends" that contain functional groups that can serve as linking reagents to connect the targeting moiety and/or therapeutic agent to the linker covalently. Suitable linkers can include a wide variety of functional groups and moieties, including but not limited to substituted or unsubstituted alkyl, substituted or unsubstituted heteroalkyl, substituted or unsubstituted aryl, aldehydes, acids, esters and anhydrides, sulfhydryl or carboxyl groups, such as maleimido benzoic acid derivatives, maleimidocaproic acid derivatives, and succinimido derivatives, or may be derived from cyano bromide or chloride, succinimidyl esters or suiphonic halides and the like.

The functional groups on the linker ends that are used to form covalent bonds between the linker and therapeutic agent on one end and the linker and targeting moiety on the other end, may be different types of functional groups and include but not limited to amino, hydrazino, hydroxyl, thiol, maleimido, carbonyl, and carboxyl groups, making the linker bifunctional. A linker may also be polyfunctional. It will be evident to those skilled in the art upon review of this disclosure that a variety of bifunctional or polyfunctional reagents, both homo- and hetero-functional (such as those described in the catalog of the Pierce Chemical Co., Rockford, Ill.), can be employed as a linker group. Coupling can occur, for example, through amino groups, carboxyl groups, sulfhydryl groups or oxidized carbohydrate residues (see, e.g., U.S. Pat. No. 4,671,958). Cyanogen bromide or chloride derivative groups; carbonyldiimidazole, thiocarbonyldiimidazole of succinimide esters or sulfonic halides; phosgene, thiophosgene; or self-rearrangeable (or "self-immolative") spacers can also be used. In one embodiment, the linker is a heterobifunctional linker such that one of the two ends reacts with the targeting moiety while the other end reacts with the drug, thus forming covalent attachments between the three portions. Heterobifunctional coupling reagents can be prepared by matching the above chemically compatible reactive groups. Some common examples are 4-fluoro-3-nitrophenylazide (FNPA), N-succinimidyl-6-(4'-azido-2'-nitrophenylamino)hexanoate (SANPAH), m-maleimidobenzoyl-N-hydroxysuccinimide ester (MBS), and succinimidyl-4-(N-maleimidomethyl)cyclohexane-1-carboxylate ester.

Typical linking reagents include those that are commercially available from Thermo Scientific and listed in the Cross linking Handbook (accessible on the world wide web at piercentet.com/Files/1601673_Crosslink_HB_Intl.pdf) as well as those from Thermo Scientific P.O. Box 117, Rockford, Ill. 61105 U.S.A, U.S.A 1-800-874-3723, International+815-968-0747. Typical linking reagents can also include amine-to-amine coupling reagents, e.g., dimethyl imidates, such as dimethyl adipimidate, dimethyl malonimidate, and dimethyl suberimidate; bisN-oxysuccinimidyl esters, such as disuccinimidyl suberate (DS) and disuccinimidyl tartarate; and bis-nitrofluorobenzenes, such as 1,5-difluoro-2,4-dinitrobenzene and 4,4'-difluoro-3,3'-dinitrophenylsulfone; sulfhydryl coupling reagents, e.g., bis-maleimido reagents, such as 1,2-phenylenedimaleimide and 1,4-phenylenedimaleimide; bis-iodoacetamides such as N,Nethylene-bis-iodoacetamide; and bis-organomercury reagents such as 3,6-bis-(mercurimethyl)-dioxan; and the highly reactive diisothiocyanates such as 4,4'-diisothiocyano-2,2'-disulfonic acid and p-phenylene-diisothiocyanate (DTIC) and aryl azides such as 4,4'-dithio-bis-phenylazide. In one embodiment, a bifunctional linker consists of a N-hydroxysuccinimide ester on one end (amine reactive) and a maleimide group (sulfhydryl reactive) on the other. N-hydroxysuccinimde (NHS) esters react with primary amines at pH 7-9 to form amide bonds, while maleimides react with sulfhydryl groups at pH 6.5-7.5 to form stable thioether bonds. Several primary amine and sulfhydryl groups are present on antibodies, and additional groups can be designed into recombinant antibody molecules. Agents can be synthesized to contain a variety of functional groups used to link them to the linkers.

The linker can impart beneficial properties to an EDC of the invention in addition to physically linking the targeting moiety and the drug. The linker can be used to minimize agent self-association or aggregation of the EDC caused by the agent (for example, by introducing a hydrophilic methoxytriethylene glycol chain onto the doxorubicin portion of the branched peptide linkers, aggregation was greatly reduced in the immunoconjugate products). The linker may also improve the therapeutic efficacy of the EDC (for example, increased linker stability between doxorubicin and BR64 monoclonal antibody resulted in increased efficacy and potency). The linker may also improve the pharmacokinetics of the EDC (for example, polyethylene glycol can increase serum half-life of antibodies and other molecules). A linker can also serve to increase the chemical reactivity of the agent or targeting moiety, and thus increase the coupling efficiency to the targeting moiety or agent. An increase in chemical reactivity can also facilitate the use of moieties, or functional groups on moieties, which otherwise would not be feasible to use. When the targeting moiety is linked to the therapeutic agent, the linker group may have several other functions, such as making the compound of the invention more bioresistant, more bio-compatible, less immunogenic, less toxic, and/or more stable while in the circulatory structure or more stable to other types of destruction or elimination or to make it non-cleavable. Thus in certain embodiments, the stable or non-cleavable linker maintains the attachment of the targeting moiety to the therapeutic agent under physiological conditions, but may also have therapeutic effects as well.

The linkers used in the EDCs of the invention are stable, and in various embodiments non-cleavable. In all embodiments, for the EDC of the invention to exert it's maximal therapeutic effect, the linker must remains intact, which requires the following: (i) the linkage between the targeting moiety and the therapeutic agent of the compound of the invention remains stable for a prolonged period of time in the circulatory structure, sufficient to allow the EDC to find and bind its target(s); (ii) the linkage remains stable while the EDC of the invention is stored under various conditions and temperatures for a prolonged period of time; and (iii) the stable characteristics of the EDC of the invention can be determined experimentally by one skilled in the art. By way of example, stable linkers are those that, when in an EDC of the invention, show minimal (i.e., less than 10%) cleavage while present in the circulatory structure, at the surface of target tissue, at the surface of target cell, or in the extracellular matrix for a period of at least 4 to 8 hours or longer, such as 8 to 24 hours, or 1 to 10 days or longer; non-cleavable linkers are stable in these conditions for longer periods, including periods as long as 20 days or longer (Durcy, L. et. al. Bioconjugate Chem. 2010, 21, 5-13).

An example of a stable, non-cleavable linker is the polyalkylene glycol linker. Polyalkyleneglycol linkers are linear chains that have at least two, and typically more than two, alkylene moieties linked together by oxygen in the form of an ether linkage. The alkylene groups can be substituted, but typically are unsubstituted, and can comprise any desired number of alkylene units, but typically at least 2 and no more than 5, or no more than 10, or no more than 25 or no more than 50, or no more than 100 such units, e.g., ethylene, propylene, hexylene, and the like. In one embodiment, the linker is composed of 24 repeating ethyleneglycol units making a PEG24-type linker. This linker would be approximately 90-100 angstoms long depending on the reactive groups attached to either end. In one embodiment, the linker is composed of a sugar. In one embodiment, the linker is composed of an amino sugar. The polyalkyleneglycol residue can comprise repeating alkylene units which are all the same or which vary in length and/or substitution. In various embodiments, the linker of the EDC of the invention is constructed using a (PEG)36 bifunctional linker. In a particular embodiment, the linker of the EDC of the invention is constructed using SM(PEG)24 from Thermo Scientific.

Any substituent of one or more alkylene units will of course be selected such that the advantageous properties of the present invention are not substantially compromised. One skilled in the art will be able to make appropriate selections in view of the disclosure herein. Typically such substituents, if present, are hydroxyl, alkoxyl, or disubstituted amino moieties. When polyethyleneglycol (PEG) is used to link the targeting moiety to the drug, the EDC may be capable of withstanding attacks by the immune system. Adding PEG to proteins or small molecules has been shown to improve therapeutic efficacy of some protein or small molecule therapeutics (see PEGylated Protein Drugs: Basic Science and Clinical; Applications Series: Milestones in Drug Therapy Veronese, Francesco M. (Ed.) 2009 and Advanced Drug Delivery Reviews Volume 55, Issue 10, 26 Sep. 2003, Pages 1261-1277, incorporated herein by reference). PEG can therefore increase the half-life, reduce the requirement for frequent dosing, and reduce antigenicity as well. In one embodiment, the bifunctional linker succinimidyl-[(Nmaleimidopropionamido)-tetracosaethyleneglycol] ester is used to couple the targeting moiety to the drug. In one embodiment, the bifunctional linker succinimidyl-[(Nmaleimidopropionamido)-dodecaethyleneglycol] ester is used to couple the targeting moiety to the drug. In one embodiment, the bifunctional linker succinimidyl-[(N-ma leimidopropionamido)-octaethyleneglycol] ester is used to couple the targeting moiety to the drug.

Drugs may be coupled through linkers to site-specific locations engineered onto antibodies to make an EDC of the invention. For example, aldehyde tags can be made through the use of the formylglycine generating enzyme (FGE) which performs posttranslational modification converting cysteines within amino acid consensus sequences, also termed "sulfatase motifs" to the aldehyde-bearing residue formylglycine (FGIy). The motifs can be installed within heterologous proteins as a genetically encoded "aldehyde tag" for site-specific labeling with aminooxy- or hydrazide-functionalized probes (see Cell. 2003 May 16; 113(4):435-44; 0.1 Am Chem Soc. 2008 Sep. 17; 130(37): 12240-12241). Another example of modifying antibodies site selectively also is accomplished through cysteines and involves first identifying reactive thiol groups on the antibody surface using a Phage ELISA selction (see J Immunol Methods. 2008 Mar. 20; 332(1-2):41-52, and US Patent Application 20080305044). Yet another method to site specifically label antibodies is through the use of unnatural amino acids incorporated into the antibody polypeptide chain (see Annu Rev Biophys Biomol Struct. 2006; 35:225-49).

Polyfunctional linkers or dendrimers can be used in accordance with the methods of the invention so that multiple agents are attached to a single attachment site on the targeting moiety. In this way, multiple agents could be attached to a single specific site on the targeting moiety, which may be engineered as discussed above, or to multiple sites where reactive side chains are located. The number of drugs and linkers will be, in any event, at least one and an upper limit can be determined experimentally by one skilled in the art. An optimal number of linkers and drugs can be determined but this is not required. For example, one linker could have multiple therapeutic agents attached (dendrimer), and an EDC with multiple linkers could have a fraction of linkers free of therapeutic agent.

An optimal linker length may be determined by experimental measurements, for example by testing multiple linker lengths in the assay used to determine activity of the resulting EDC of the invention. For example, if linker length is too short (not allowing the drug and targeting moiety to reach their binding sites simultaneously), one can readily identify and correct the problem to provide an EDC of the invention. Typically, the linker length will be in the range of about 50 to about 500 Angstroms or about 50 to about 200 Angstroms. The linker length and composition is selected to ensure that the EDC remains stable in the circulatory structure where enzymes and other environmental substances may otherwise break it down and to reflect the distance from where the targeting moiety binds to its antigen and where the agent acts on its target. A wide variety of linkers that comply with these requirements are available or can be synthesized, which creates a very large class of EDCs provided by the invention, particularly when one considers the wide variety of linkers, therapeutic agents and targeting moieties that can be employed in the EDCs of the invention.

Agent loading refers to the average number of agents per targeting moiety (i.e., antibody). Where each linker is linked to one agent, the average number of agents will equal the average number of linkers on the targeting moiety. Agent loading typically ranges from 1 to 8 agents per targeting moiety, if the targeting moiety is an antibody (Ab), i.e. where 1, 2, 3, 4, 5, 6, 7, and 8 agents are covalently attached to the antibody. Thus, compositions of EDCs include collections of antibodies conjugated with a range of drugs, from 1 to 8. The average number of drugs per antibody in preparations of EDC from conjugation reactions may be characterized by conventional means such as mass spectroscopy, ELISA assay, electrophoresis, and HPLC. By ELISA, the averaged value of agents in a particular preparation of EDC may be determined (Hamblett et al (2004) Clinical Cancer Res. 10:7063-7070; Sanderson et al (2005) Clinical Cancer Res. 11:843-852). However, the distribution of agents and/or linkers are not discernible by the antibody-antigen binding and detection limitation of ELISA. Also, ELISA assay for detection of antibody-drug conjugates does not determine where the drugs are attached to the antibody, such as the heavy chain or light chain fragments, or the particular amino acid residues. In some instances, separation, purification, and characterization of homogeneous EDC where the number of agents is a certain value from EDC with other drug loadings may be achieved by means such as reverse phase HPLC or electrophoresis.

For some EDCs, the number of agents and/or linkers may be limited by the number of attachment sites on the targeting moiety. For example, where the attachment is a cysteine thiol, as in certain illustrative embodiments herein, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with a drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. Additionally, the antibody must be subjected to denaturing conditions to reveal reactive nucleophilic groups such as lysine or cysteine. The loading (drug/antibody ratio) of an EDC may be controlled in several different manners, including: (i) limiting the molar excess of drug-linker intermediate (D-L) or linker reagent relative to antibody, (ii) limiting the conjugation reaction time or temperature, and (iii) partial or limiting reductive conditions for cysteine thiol modification.

Where more than one nucleophilic or electrophilic group of the antibody reacts with a drug-linker intermediate, or linker reagent followed by drug moiety reagent, then the resulting product is a mixture of EDC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of EDC with a single agent loading value may be isolated ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). However, these single loading value EDCs may still be heterogeneous mixtures because the drug moieties may be attached, via the linker, at different sites on the antibody.

Thus, the EDCs of the invention can utilize any of a wide variety of stable or non-cleavable linkers.

IV. THERAPEUTIC AGENTS (DRUGS)

A wide variety of therapeutic agents are suitable for use in the EDCs of the invention. For example and without limitation, the therapeutic agent can be an agent with anti-tumor, anti-angiogenic, or anti-inflammatory therapeutic activity. Preferably, the site where the drug is attached to the linker is at a position where the linker attachment only minimally interferes or does not interfere at all with the drug's activity. The drugs used in the EDCs of the invention bind extracellular targets.

In one embodiment of the invention, the agent is a "non-internalizing therapeutic agent". In various embodiments of the invention, the targeting moiety's target is a cell membrane receptor, and the agent it acts on is a site that is on the extracellular portion of and in close proximity to the targeting moiety target. Advantageous properties of agents that do not require cellular internalization include: (i) increased potency because the process of cellular uptake of certain therapeutic agents is not efficient; (ii) endocytosis does not occur and therefore the agent remains near or on the target for a prolonged period of time depending on its binding affinity; (iii) endocytosis does not occur and therefore the agent does not reach the lysosomal system and is not degraded to a significant extent by lysosomal enzymes; and/or (iv) cellular uptake can require special physiological properties and thus the EDC is easier to construct. The non-internalizing characteristic of a therapeutic agent can be determined experimentally by one skilled in the art. In various embodiments, the non-internalizing therapeutic agent of the invention interacts with a target present at the surface of target cell.

In another embodiment, the therapeutic agent is not a microtubule inhibitor, a DNA alkylating agent or an inducer of DNA double strand breaks. In another embodiment, the therapeutic agent is not an auristatin, maytansinoid, duocarmycin, or calicheamicin. In another embodiment, the therapeutic agent has an $IC_{50}$ (in vitro) not less than 10 picomolar (pM), 20 pM, 30 pM, 40 pM, 50 pM, 60 pM, 70 pM, 80 pM, 90 pM or 100 pM. In another embodiment, where the therapeutic agent is a glycoside or cardiac glycoside, the glycoside or cardiac glycoside does not have an $IC_{50}$ less than about 1 nM.

In many cases, therapeutic agents have side effects not related to the target of activation specified to the specific indication. Such side effects are complex phenomenological observations that have been attributed to a number of molecular scenarios including direct interaction with off-target binding [see Keiser, M J, et. al. Nature 462, 175 (2009), Blagg, Annu. Rep. Med. Chem. 41, 353 (2006), Toxicity and Drug Discov. Today 10, 1421 (2005)]. Subsequent activation of other targets can lead to harmful side effects, and several lines of evidence suggest that drugs may have multiple physiological targets [see Campillos et al. Drug target identification using side-effect similarity. Science 321, 263-266 (2008)]. For example, antiParkinsonian drugs such as Permax and Dostinex activate not only dopamine receptors but also $5-HT_{2B}$ serotonin receptors, thereby causing valvular heart disease and severely restricting their use (see Roth, Drugs and valvular heart disease. N. Engl. J. Med. 356, 6-9 (2007)].

For anticancer (and other) agents, the term therapeutic index is used, in many cases to compare actual antitumor (or other therapeutic) effects to off-target toxic effects. An example of a potential anticancer drug is digitoxin, which has strong antitumor activities but high cardiotoxicity (see, Goldin. Digitalis and cancer. Lancet 1984; 1:1134). Therefore the drug alone has not been found effective as an anticancer agent in humans. Various cardiac glycoside agents such as digitoxin or proscillaridin are useful in various embodiments of the invention even though they have been reported to exhibit cytotoxic activity against several different cancer types but at concentrations not achievable in patient plasma due to their cardiotoxic effects at such concentrations [see Felth, J. et. al. J. Nat. Prod. 72, 1969 (2009)]. Cardiac glycosides are a class of drugs derived from plants of the genera Digitalis, Strophanthus, and others, which have been prescribed for centuries to treat congestive heart failure and arrhythmias. In these conditions, cardiac glycosides bind to the $Na^+/K^+$ ATPase and inhibit its pumping activity. Studies performed over the last decade show that cardiac glycosides have activity as anticancer agents [Mijatovic et al. (2007) Biochim Biophys Acta 1776:32-57 and PCT Pub. No. 2010/017480].

In one embodiment of the invention, the therapeutic agent in the EDC is a cardiac glycoside. In one embodiment of the invention, the agent is proscillaridin. In another embodiment of the invention, the agent is composed of a novel sugar enhanced proscillaridin. In another embodiment of the invention, the agent is composed from a cardiac glycoside which is void a sugar. In various embodiments of the invention, the cardiac glycoside is a compound identified in PCT Pub. No. WO 2010/017480 (PCT/US2009/053159).

Non-limiting examples of suitable cardiac glycoside compounds of Formula I as well as pharmaceutically acceptable esters, derivatives, conjugates, hydrates, solvates, prodrugs and salts thereof, or mixtures of any of the foregoing:

(I)

where the steroidal rings are either saturated, unsaturated or a combination thereof,

R =

$R^a$ is $CH_3$;
$R^b$ is $CH_3$, $CH_2OH$, or CHO;
$R_c$ is H, OH or $CH_3COO$;
$R_d$ is H, OH or $CH_3COO$;
$R_e$ is H or no group;
$R_f$ is H, OH or, when $R_e$ is H or a C=C exists between the atoms joined to $R_e$, $R_f$ and $R_g$, $R_f$ is no group;
$R_g$ is H or, when $R_e$ is H or a C=C exists between the atoms joined to $R_e$, $R_f$ and $R_g$, $R_g$ is no group;
$R_h$ is H or OH;
X is 0 or N(OR');
R' is an alkyl or aryl group; and
Sugar is D or L of hexose, pentose, deoxyhexose, deoxypentose, deoxy-halohexose, deoxy-halopentose, deoxy-aminopentose, deoxy-aminohexose, tetrose, heterosugar, carboxysugar, a derivative of the aforementioned sugars, a disaccharide derived from at least one of the aforementioned sugars, or a polysaccharide derived from at least one of the aforementioned sugars. Suitable sugars include, e.g., L-ribose, D-ribose, L-fucose, D-fucose, 2-deoxy-D-ga lactose, 3-deoxy-D-glucose, 6-deoxy-D-glucose, 2-deoxy-2-fluoro-D-glucose, 6-deoxy6-fluoro-D-glucose, L-lyxose, D-lyxose, L-rhamnose, L-allose, D-allose, L-altrose, D-altrose, L-galactose, D-galactose, L-xylose, D-xylose, D-gulose, L-mannose, D-mannose, L-idose, D-idose, Lmycarose, 6-keto-D-galactose, L-arabinose, D-arabinose, N-acetyl-D-galactosaminose, melibiose, lactose, maltose, D-galacturonose, L-talose, D-talose, 6-deoxy-6-azo-D-mannose, L-glucose, D-glucose, and mixtures thereof.

In another embodiment, the cardiac glycoside is of Formula (II) as well as pharmaceutically acceptable esters, derivatives, conjugates, hydrates, prodrugs, solvates and salts thereof, and mixtures of any of the foregoing:

(II)

wherein $R^1$ is selected from the group consisting of

, , and ;

$R^2$ and $R^3$ are each independently hydrogen, or $R^2$ and $R^3$ along with the attached carbons represent a carbon-carbon double bond;

$R^4$ is selected from the group consisting of

, ,

, and their epimers and conformers; and X is 0 or $NR^5$, wherein $R^5$ is selected from hydrogen, methyl, ethyl, isopropyl and propyl.

In still other embodiments, suitable cardiac glycosides are of Formula (II) wherein when X=NMe, $R^1$ is

;

$R^2$ and $R^3$ together with the attached carbons represent a carbon-carbon double bond; and $R^4$ is selected from the group consisting of

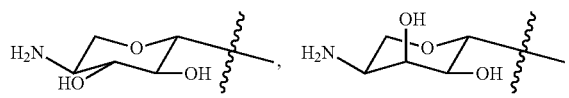 [SMILES: *C1OCC(N)C(O)C1O ; *C1OCC(N)C(O)C1O]

and their epimers and conformers.

In other embodiments, suitable cardiac glycosides are of formula II wherein when X=O, $R^1$ is selected from the group consisting of

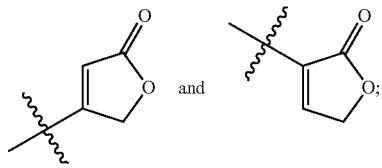 [SMILES: *C1=CC(=O)OC1 ; "and" ; *C1=CCOC1=O]

$R^2$ and $R^3$ are each hydrogen, and $R^4$ is selected from the group consisting of

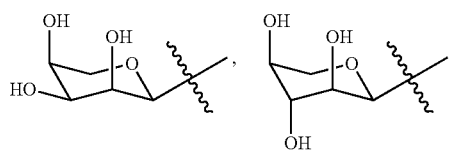 [SMILES: *C1OCC(O)C(O)C1O ; *C1OCC(O)C(O)C1O]

and their epimers and conformers.

In another embodiment, cardiac glycosides useful in accordance with various embodiments of the invention include compounds of Formula (II) wherein X=O; $R^1$ is

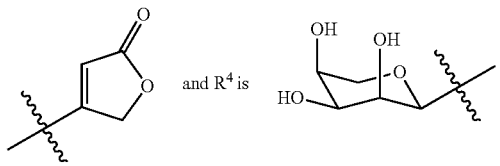 [SMILES: *C1=CC(=O)OC1 ; *C1OCC(O)C(O)C1O]

and its epimers and conformers.

In still another embodiment, cardiac glycosides useful in accordance with the invention include a compound of Formula (II) wherein X=O; $R^1$ is

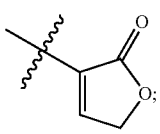 [SMILES: *C1=CCOC1=O]

and $R^4$ is selected from

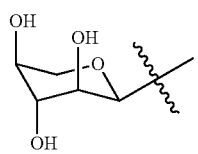 [SMILES: *C1OCC(O)C(O)C1O]

and its epimers and conformers.

In yet another embodiment, cardiac glycosides suitable for use in accordance with the invention include compounds of Formula (II) wherein X=NMe; $R^1$ is

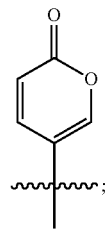 [SMILES: *c1ccc(=O)oc1]

$R^2$ and $R^3$ along with the attached carbons represent a carbon-carbon double bond; and $R^4$ is selected from

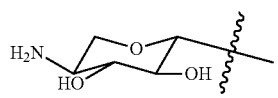

and its epimers and conformers.

In yet another embodiment, cardiac glycoside compounds useful in accordance with the invention include compounds of Formula (II) wherein X=NMe; $R^1$ is

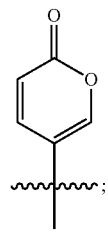 [SMILES: *c1ccc(=O)oc1]

$R^2$ and $R^3$ along with the attached carbons represent a carbon-carbon double bond; and $R^4$ is selected from

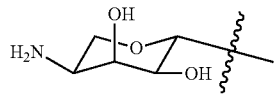

and its epimers and conformers.

In one embodiment, cardiac glycoside compounds suitable for use in accordance with the invention include CEN08-178 (3-O-digitoxigenin-L-riboside), CEN08-193 (3-0-isodigitoxigenin-L-xyloside), CEN08-243 ((3S)-3-N-methoxyamino-scillarenin-L-neo-4-amino-4-deoxyxyloside), or CEN08-244 ((3S)-3-N-methoxyamino-scillarenin-L-neo-4-amino-4-deoxyriboside).

In other embodiments of the EDCs of the invention, the agent is or is a derivative of a compound selected from the group consisting of cyclopamine, statins, itraconazole, LDE225, BMS 833923, GDC-0449, purmorphamine, SANT1, Cur-61414, SAG, IPI-926, 1-amino-4a rylphthalazine, AR-C117977, ARC155858, DIDS, luteolin, phloretin, quercetin, gammahydroxybutyric acid, alpha-cyano-4-hydroxycinnamic acid, lonidamide, integrin inhibitors, RGD peptides, EMD 121974 (Cilengitide), 536578, 5247, 5137, PSK1404, SEW 2871, W146, FTY720-P, semaphorin, alpha-cobratoxin, quinidine, AMD3100, L365-260, Dapagliflozin, BMS-512148, GW189075, GW-869682, AVE-2268, KGT-1681, KGT-1251, TS-033, YM-543, T-1095, Fluoxetine, serotonin, Sonnoside B, CYM 5442, miniglucagon, 2-deoxyglucosamine, dipyridalone, flavonoids, isoflavones, phloretin, phlorizin, imatinib, gefitinib, 2-(2-methyl)-thiadiazolylsufanyl-3-triflouromethyl-6,7-dichloroq uinoxaline, methyltryptophan, CYM 5442, omeprazole, esomeprazole, lansoprazole, pantoprazole, rabeprazole, concanamycin, bafilomycin, higrolidin, chondropsin, salicylihalamide, lobatamide, concanamycin, plecomacrolide, benzolactone enamide, archazolid, chondropsin, indole, benzolactone enamide (salicylihalamide), lobatamide A and B, apicularen, indolyl, oximidine, macrolactone archazolid, lobatamide C, cruentaren, plecomacrolide, benzolactone enamide, archazolid, chondropsin and indole, benzolactone enamide (salicylihalamide), lobatamide A and B, apicularen, indolyl, oximidine, macrolactone archazolid, lobatamide C, cruentaren, NiK12192, FR202126, PPI SB 242784, NiK12192, FR202126, PPI SB 242784, cardiac glycoside, CEN-09-106, CEN-09-107, ivermectins, gramadicins, istaroximes, AR-C117977, ARC155858, DIDS, luteolin, phloretin, quercetin, gammahydroxybutyric acid, itraconazole, LDE225, BMS 833923, GDC-0449, purmorphamine, SANT1, Cur-61414, SAG, IPI-926, 1-amino-4-arylphthalazines, robotokinin, and peptide antagonist like NH2-DXFSRYLWS. In various embodiments, the agent is a channel blocker; in other embodiments, the agent is not a channel blocker.

Thus, a wide variety of therapeutic agents can be employed in the EDCs of the invention.

V. EDC CONSTRUCTION, SCREENING, AND SPECIFIC EMBODIMENTS

The present invention provides EDCs that comprise a targeting moiety linked to a therapeutic agent via a stable (and, in some embodiments, non-cleavable) linker and where drug and targeting moiety dissociation is not required for efficacy. Thus, the EDCs of the invention comprise (i) a targeting moiety targeting an extracellular target, (ii) a stable or non-cleavable linker, and (iii) a therapeutic agent that targets an extracellular target. The EDC can be represented as follows: (targeting moiety)-(linker)-(therapeutic agent).

An EDC of the invention may be prepared by any of several routes, employing organic chemistry reactions, conditions, and reagents known to those skilled in the art, including: (1) reaction of a nucleophilic group or an electrophilic group of a targeting moiety with a bivalent linker reagent, to form antibody-linker intermediate, via a covalent bond, followed by reaction with an activated agent; and (2) reaction of a nucleophilic group or an electrophilic group of an agent with a linker reagent, to form drug-linker intermediate, via a covalent bond, followed by reaction with the nucleophilic group or an electrophilic group of a targeting moiety. Conjugation methods (1) and (2) may be employed with a variety of targeting moieties, agents, and linkers to prepare an EDC of the invention.

Nucleophilic groups on antibodies for example include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody-drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium metaperiodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

In one embodiment, EDCs of the invention are constructed by combinatorial synthesis and screening. Libraries or combinations of targeting moieties and agents linked through non-cleavable or stable linkers can be constructed and screened to identify specific EDCs of the invention. In one embodiment, a single non-internalizing agent is linked to a library of targeting moieties and screened for a particular therapeutic effect to identify EDCs of the invention. In one embodiment, a single non-internalizing targeting moiety is linked to a library of agents and screened for a particular therapeutic effect to identify EDCs of the invention. In one embodiment, a a library of non-internalizing agents is linked to a library of targeting moieties and screened for a particular therapeutic effect to identify EDCs of the invention.

One of skill in the art will appreciate that EDCs can be prepared by any of several routes, employing well known organic chemistry reactions, conditions, and reagents, including: (1) reaction of a nucleophilic group or an electrophilic group of a targeting moiety with a bivalent linker reagent to form targeting moiety-linker intermediate via a covalent bond, followed by reaction with an activated drug moiety; and (2) reaction of a nucleophilic group or an electrophilic group of a drug moiety with a linker reagent, to form drug-linker intermediate, via a covalent bond, followed by reaction with the nucleophilic group or an electrophilic group of a targeting moiety. Conjugation methods (1) and (2) may be employed with a variety of targeting moieties, drug moieties, and stable or non-cleavable linkers to prepare the EDC of the invention.

Nucleophilic groups on targeting moieties include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain targeting moieties like antibodies may have reducible interchain disulfides, i.e. cysteine bridges. Antibodies may be made reactive for conjugation with linker reagents by treatment with a reducing agent such as DTT (Cleland's reagent, dithiothreitol) or TCEP (tris (2-carboxyethyl)phosphine hydrochloride; Getz et al (1999) Anal. Biochem. Vol 273:73-80; Soltec Ventures, Beverly, Mass.). Each cysteine disulfide bridge will thus form, theoretically, two reactive thiol nucleophiles. Additional nucleophilic groups can be introduced into protein targeting moieties through the reaction of lysines with 2-iminothiolane (Traut's reagent) resulting in conversion of an amine into a thiol.

EDC's may also be produced by modification of the targeting moiety to introduce electrophilic moieties, which can react with nucleophilic substituents on the linker reagent or drug. For example, sugars of glycosylated proteins may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated protein with either galactose oxidase or sodium meta-periodate may yield carbonyl (aldehyde and ketone) groups in the protein that can react with appropriate groups on the drug (Hermanson, G. T. (1996) Bioconjugate Techniques; Academic Press: New York, p 234-242). In another embodiment, proteins containing N-terminal serine or threonine residues can react with sodium metaperiodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Close proximity targets may be chosen in a number of methods. One such method will be to search literature references for targets that are important to a disease or indication of interest. Drugs relevant to these targets can then be identified either by searching for preexisting drugs (e.g. FDA approved drugs) or by screening drug libraries. If drugs exist, one would search for epitopes near the drugs' target to which targeting moieties would bind yet not interefere with the drugs binding.

In some cases, the epitopes may be on the same protein. Finding close proximity epitopes on the same protein may be accomplished through known molecular structures such as co-crystal structures where the drug and target are shown at the molecular level. Epitopes near the drugs' binding site can then be assessed, selected, mimics produced and screened for binding targeting moieties. One examples of this would be to produce peptides identical to the epitope whereby antibodies could be produced and screened. Another method would be to produce the entire protein or over-express the protein on the surface of cells and produce antibodies which would subsequently be screened for specific epitope binding.

In some cases, the epitopes may be on a protein that forms a complex with the drug's target or on different proteins that may merely be in close proximity. In many of these cases, the complex or the two proteins will be located on the cell surface membrane. Interactions between membrane-bound proteins play a significant role in a variety of cellular phenomena, including the transduction of signals across membranes, the transfer of membrane proteins between the plasma membrane and internal organelles, and the assembly of oligomeric protein structures. In some cases, close proximity proteins may be known. In other cases, known close proximity proteins that form complexes have been tested by crosslinking studies or by testing their interactions in model systems or by removing one of the proteins in a model cell and running tests to analyze the outcome. When specific antibodies are available, immunoprecipitation of the target protein along with its noncovalent binding protein partners, i.e., coimmunoprecipitation (co-IP), has been a commonly used technique for identifying potential interacting proteins surrounding the target proteins. Co-IP methods have generated large-scale protein interaction data in yeast, mammalian, and many other organisma, and the validation of many of these results with orthogonal methods confirms the utility of these methods. Chemical cross-linking coupled with immunoprecipitation provides an alternative strategy for in vivo identification of protein—protein interactions which has been extensively reviewed. Cross-linking reactions can be carried out with intact cells and chemically "freeze" protein—protein interactions with stable covalent bonds that allow subsequent purification steps to be carried out under much harsher or more stringent conditions. Consequently, nonspecific binding can be reduced considerably. In addition, immunoprecipitation in conjunction with cross-linking is well suited for investigating the interactions of membrane proteins. Isolation and purification of membrane proteins usually requires use of detergents that can sometimes disrupt interactions among membrane proteins. Thus, stabilization of the complexes with cross-linkers prior to immunoprecipitation of membrane proteins significantly increases the chances of identification of the proteins bound to the antigens.

In this case, one skilled in the art would know how to crosslink associated or complex targets chemically. For example, protein—protein contacts can be revealed by incubating samples with cross-linking reagents. Complexes can be detected and isolated either by SDSPAGE or by HPLC. Once isolated the targets can be digested and analyzed by mass spectroscopy to determine the fragments molecular mass and entered into databases or through computer algorithms, such as Mink (Lee Y J. et al. *J Proteome Res.* 2007 Oct.; 6(10):3908-17) to determine the actual proteins that form the close proximity targets. Employing chemical cross-linkers with added hydrophobicity coupled with immunoprecipitation is a more recent finding and a practical strategy for mapping protein—protein interactions in cell membranes (Tang, X. et al. MoL BioSyst., 2010, 6, 939-947). Once close proximity targets of this type are believed to exist, antibodies labeled with fluorescent dye pairs to both proteins can be used to confirm close proximity. The process of finding drugs and targeting moieties in close proximity to targets of this type would be as described above for targets that exist on the same protein.

An EDC of the invention would then be prepared as described above by attaching the drug and the targeting moiety which both interacts with targets suspected of or confirmed as being in close proximity via a stable and/or non-cleavable linker. Generally speaking, the linker should be no less than 50 angstoms in length but could be as long as 500 angstroms in length. The EDC consisting of a drug, a linker and a targeting moeiety all attached covalently would then be purified away from uncoupled drug, linker and targeting moiety using standard affinity, size exclusion, filtration, or other methods known to one skilled in the art.

Once a particular EDC is constructed, it may be screened using any of various methods known to those skilled in the art. It should be noted that in cases where the targets of the drug and targeting moiety are found on different proteins, these targets may only be in close proximity on certain cell types and thus multiple screens should be conducted in order to better understand the specificity and what cell types may have the targets in close proximity. These include but are not limited to various in vitro and in vivo methods known in the art. Candidate EDCs may be screened serially and individually, or in parallel under medium or high-throughput screening formats. The rate at which EDC may be screened for utility for prophylactic or therapeutic treatments of diseases or disorders is limited only by the rate of synthesis or screening methodology, including detecting/measuring/analysis of data.

Generally, in vitro screening is conducted first. For example, the cytotoxic or cytostatic activity of an EDC is first measured by: exposing test cells, e.g. mammalian cells having tumor-associated antigens or receptor proteins to the antibody of the EDC, in a cell culture medium; culturing the cells for a period from about 6 hours to about 5 days; and measuring cell viability (or other property). Cell-based in vitro assays are used to measure viability, i.e. proliferation ($IC_{50}$), cytotoxicity ($EC_{50}$), and induction of apoptosis (caspase activation) of the EDC.

For in vivo testing, transgenic animals and cell lines are particularly useful in screening antibody-drug conjugates (EDC) that have potential as prophylactic or therapeutic treatments of diseases or disorders involving overexpression of tumor-associated antigens and cell surface receptors, e.g. HER2 (U.S. Pat. No. 6,632,979). Screening for a useful EDC may involve administering candidate EDC over a range of doses to the transgenic animal, and assaying at various time points for the effect(s) of the EDC on the disease or disorder being evaluated. Alternatively, or additionally, the drug can be administered prior to or simultaneously with exposure to an inducer of the disease, if applicable.

EDCs of the invention are provided in a variety of embodiments. In one embodiment, the target of the targeting moiety and the target of the agent are the same. In one embodiment, the target of the targeting moiety and the target of the agent are part of the same multi-target complex. In one embodiment, the targeting moiety and the therapeutic agent, when linked together, act on the same target, and targeting moiety binding does not prevent the agent's effect or binding. In one embodiment, the targeting moiety and the therapeutic agent, when linked together, act on the same target where targeting moiety binding occurs simultaneously with agent binding and effect. In one embodiment, the targeting moiety and the therapeutic agent, when linked together, act synergistically. In all embodiments, the target of the targeting moiety and the target of the agent are both extracellular. In one embodiment, the target of the targeting moiety forms a complex with the target of the agent. In one embodiment, the invention provides an EDC that comprises a non-internalizing targeting moiety linked through a stable or non-cleavable linker to an agent. In all embodiments, the invention provides an EDC that does not require internalization to cause a therapeutic effect. In all embodiments, the invention provides an EDC that is composed of a non-internalizing targeting moiety and a therapeutic agent that acts on an extracellular target. In all embodiments, the linker of the invention is selected to allow both the targeting moiety and the agent to bind or act on their targets without requiring linker cleavage. In all embodiments, the targeting moiety and the therapeutic agent bind simultaneously to create a desired therapeutic effect. In all embodiments, the linker is long enough to allow simultaneous binding of the targeting moiety and the agent. In various embodiments, the targeting moiety and the therapeutic agent, linked by a stable or non-cleavable linker, act on different targets. In the latter embodiments, the targeting moiety and the therapeutic agent are linked by a stable or non-cleavable linker that is long enough to allow the targeting moiety and agent to act on or bind simultaneously to different targets.

In various embodiments, the target antigens are on tumor cells, stromal cells, endothelial cells of tumors, cells such as macrophages, neutrophils, and monocytes, or are otherwise antigens associated with cancer, inflammatory reactions, diabetes, or pain. The compounds of the invention are administered to the patient, carried through the blood stream, and, when in the vicinity of a target cell or antigen, bind to a target antigen via the targeting moiety and simultaneously or contemporaneously bind to the target of the drug to create a desired therapeutic effect. In another embodiment, EDCs of the invention comprise a targeting moiety that recognizes targets associated with metastatic diseased cells. Targets such as dysadherin have been found associated with metastatic diseased cells. Thus, in some embodiments, EDCs of the invention comprise a targeting moiety that binds to dysadherin.

In another embodiment, the invention provides an EDC that comprises an agent, a stable or non-cleavable linker, and a targeting moiety that recognizes an isoform of a subunit of the Na,K-ATPase ion transporter complex. The Na,K-ATPase is characterized by a complex molecular heterogeneity that results from the expression and differential association of multiple isoforms of its alpha-, beta- and gamma-subunits (see review in Am. J. Physiol. 275 (Renal Physiol. 44): F633-F650, 1998). The Na,K-ATPase belongs to a widely distributed class of P-type ATPases that are responsible for the active transport of a variety of cations across cell membranes. At present, as many as four different alpha-isoforms, three distinct beta-isoforms, and nine distinct gamma-isoforms have been identified in mammalian cells. The stringent constraints on the structure of the complex's isoforms during evolution and their tissue specific and developmental pattern of expression suggests that different Na,K-ATPase complexes have evolved distinct properties to respond to cellular requirements. Different isoforms of the alpha-subunit are expressed at different levels on different cell types and behave differently. Therefore, EDCs of the invention include those targeting the various different Na,K-ATPase complexes. The alpha-subunit contains the binding sites for cations, ATP, Src kinase, and various therapeutic agents. Some of the agents are derived from the cardiac glysoside class of molecules. Therefore in one embodiment of the invention, the alphi-subunit can act as the target for the agent of EDCs of the invention and the agent is a cardiac glycoside. In another embodiment, the invention provides an EDC that comprises a targeting moiety that recognizes a subunit isoform of the Na,K-ATPase complex, a stable or non-cleavable linker, and a therapeutic agent which acts on the alpha-subunit of the Na,K-ATPase. Specifically, the cardiac glycoside class of molecules has been mainly used therapeutically in the treatment of cardiac failure, due to their anti-arrhythmic effects. Recently it was determined that this class of drugs also has anticancer activities, yet use as an anti-cancer drug has not yet been approved due to cardiotoxicity at levels required. Targeting this class of molecules away from the heart and toward cancer cells would thus be beneficial. Therefore, in one embodiment of the invention, cardiac glycoside derivatives can act as the agent of the EDC of the invention. In one embodiment, these EDCs comprise a therapeutic agent that is a member of the cardiac glycoside class of small molecules. In various embodiments of the invention, cardiac glycosides and related agents are attached through a stable linker to antibodies that target the drugs to cancerous tissue providing therapeutically useful EDCs of the invention for treating cancer [(Johansson, et al, Anti-Cancer Drugs (2001) 12; 475-483) and (Prassas and Diamandis, Nature Drug Discovery (2008) 7; 926932) and (Mijatovic et al. Expert Opin. Ther. Targets (2008) 12 (11) 1403-1417).

The beta-subunit of the Na,K-ATPase complex is believed to act as a chaperone for the alpha-subunit, directing its location on the cell membrane and can be aberrantly glycosylated on certain diseased cells. Targeting moieties that differentially bind to certain glycosylated forms of proteins have been generated. Therefore, in one embodiment of the invention, aberrantly glycosylated targets can act as a target for the targeting moiety of EDCs of the invention. The different isoforms of the beta-subunit are found on different cells and expressed at different levels. Therefore, in one embodiment of the invention, EDCs of the invention comprise targeting moieties that specifically recognize an isoform of the target complex. More specifically, in another embodiment of the invention, EDCs of the invention comprise targeting moieties that specifically recognize a beta-subunit isoform of the target complex.

The gamma-subunit's specific role is thought to regulate the activity of ion transport and has been shown to modify voltage dependence of the complex. The gamma-subunit is thought not to be required for ATPase activity (Biochem Biophys Res Commun 1981 102:250-257). Specifically, the gamma subunit isoform 5 is over-expressed on certain cancer cell types and appears to be a sole prognosticator of metastasis (Nam, J. et. al Cancer Lett. 255(2): 161-169). Gamma-subunits are constructed from a FXYD peptide span that is universal. There are multiple FXYD or gamma-subunit isoforms and expression differs by cell type and cell environment. This subunit also has been shown to complex with other proteins besides the Na,K-ATPase ion pump. Tissue/cell-specific expression of the regulatory FXYD subunits of Na-K-ATPase is not static, and may be changed to adapt to a given physiological or pathological situation. It is believed that a complex that includes an FXYD subunit will do so base on expression levels of the various isoforms and competition with the complexes it associates with. Therefore, expression of FXYD and specifically FXYD5, does not always indicate that it will be associated with the Na,K-ATPase ion channel.

Thus in another embodiment of the invention, gamma-subunit 5 (also known as dysadherin and FXYD5) can act as a target for the targeting moiety of EDCs of the invention. In particular, one embodiment of an EDC of the invention comprises an agent that acts on the Na,K-ATPase ion pump, a non-cleavable linker and an antibody which binds to the gamma 5 subunit FXYD5. In another embodiment of the invention, a cardiac glycoside is attached through a non-cleavable or stable linker to a targeting moiety which binds to FXYD5. In another embodiment of the invention, a cardiac glycoside is attached through a non-cleavable or stable linker to an targeting moiety which is an antibody that binds to FXYD5. In another embodiment of the invention, an cardiac glycoside is attached through a non-cleavable or stable linker to the antibody M53. In another embodiment of the invention, the cardiac glycoside CEN-09-106 is attached through a non-cleavable or stable linker to the antibody M53. In another embodiment of the invention, the cardiac glycoside CEN-09-106 is attached through a PEG linker to the antibody M53. In another embodiment of the invention, the cardiac glycoside CEN-09-106 is attached through a PEG24 linker to the antibody M53.

The invention also provides EDCs that comprise a targeting moiety linked to a cardiac glycoside that can be used as anti-inflammatory agent or to treat other diseases. Studies suggest the Na,K-ATPase subunit isoform/modulator distribution and levels in the lungs of cystic fibrosis patients are distinct from those of a normal lung, and so are a target for therapeutic agents against cystic fibrosis hyperinflammation. Studies reveal that cardiac glycosides that bind to the Na,K-ATPase can suppress hypersecretion of IL-8 from cultured CF epithelial cells via specific inhibition phosphorylation of a NF-kappa B inhibitor (see Srivastava, M., et. al. Proc. Natl. Acad. Sci. USA 2004, 101, 7693-7698, incorporated herein by reference). A review of the potential therapeutic uses of cardiac glycosides discusses obesity, kidney disease, migraines, epilepsy, dystonia, Parkinsonism (2007 Journal of Internal Medicine 261; 44-52).

In another embodiment, the invention provides an EDC that comprises an agent, a stable or non-cleavable linker, and a targeting moiety that recognizes the monocarboxilate transporter (MOT) or an a protein complexed with MOT protein. MCT1 and MCT4 (known as SLC16A1 and SLC16A3, respectively) key lactate membrane importer (MCT1) and exporter (MCT4) are overexpressed in various cancers to compensate for altered lactate production (a basic signature of cancer). The glycoprotein CD147 (also known as basigin, EMMPRIN, OX-47 and HT7—overexpressed in many cancers and used as a prognostic marker) is required for functional assembly of MCT1 and MCT4 and exists in the functional transporter complex. Therefore, EDCs of the invention include those targeting various monocarboxilate transporter proteins or proteins that are complexed with MCT proteins. While small molecule inhibition of MCT, CD147 silencing and CD147-targeted mAbs display anticancer properties, most MCT inhibitors to date lack specificity and/or sufficient potency. Conjugation of MCT inhibitors to anti-CD147 mAbs (as described in this application) is anticipated to overcome these limitations.

In another embodiment, the invention provides an EDC that comprises an agent, a stable or non-cleavable linker, and a targeting moiety that recognizes the facilitative glucose transporters (GLUTs). The facilitative transporter GLUT1 is overexpressed and confers poor prognosis in a wide range of solid tumors, the role of which is to compensate for altered metabolism (glucose metabolism widely recognized as the Warburg effect) in cancer cells. GLUT1 overexpression is believed to also contribute non-metabolic protumorigenic effects and inhibition of GLUT1 (siRNA, mAbs or small molecule inhibitors) reduce tumorgenicity. Additionally GLUT1 is a receptor for the human T cell leukemia virus (HTLV) associated with leukemia and neurological syndromes. Notably, GLUT inhibitors to date have moderate affinity at best and display fairly broad specificity. Therefore, EDCs of the invention include those targeting various monocarboxilate transporter proteins or proteins that are complexed with GLUT transporter proteins. Conjugation of GLUT inhibitors to anti-GLUT mAbs (as described in this application) is anticipated to overcome these limitations.

In another embodiment, the invention provides an EDC that comprises an agent, a stable or non-cleavable linker, and a targeting moiety that recognizes the Sodium-glucose cotransporters (SGLTs) or proteins associated with SGLTs. In the kidney tubule, the bulk of the filtered glucose is reabsorbed by the low-affinity sodium-glucose cotransporter (SGLT)2, with the residue being reabsorbed by the high affinity SGLT1. SGLT2 plays a dominant role in the control of glucose transport in the kidney, with SGLT1 having a supporting role. SGLT2 inhibitors cause excess glucose energy to be discarded in the urine by inhibiting renal glucose reabsorption, and consequently shift the energy balance in a negative direction. This renal glucose excretion has the potential to lower the plasma glucose level, abolish glucose toxicity and thereby achieve an improvement in the pathogenesis associated with diabetes. Therefore, EDCs of the invention include those targeting various monocarboxilate transporter proteins or proteins that are complexed with SGLTs.

In another embodiment, the invention provides an EDC that comprises an agent, a stable or non-cleavable linker, and a targeting moiety that recognizes proteins associated with the Hedgehog pathway. In the Hedgehog (Hh) pathway, the 12 transmembrane receptor patched (PTCH) is a negative regulator of the seven transmembrane receptor smoothened (SMO). PTCH is the receptor for the Hh ligand and inhibits SMO until the Hh ligand binds, allowing SMO to signal. Through an intracellular pathway that is still incompletely understood, this signaling event results in the nuclear translocation of the Hh transcription factors Gli1 and Gli2, which initiate transcription of Hh responsive genes. During development, this pathway is responsible for embryonic patterning in a variety of tissues. There is also strong evidence linking alterations in the Hh pathway (leading to uncontrolled SMO signaling) in a number of cancers. Therefore, EDCs of the invention include those targeting various proteins of the Hedgehog pathway. Specifically conjugation of small molecule effectors of the Hedgehop pathway to antiSMO or anti-Patch mAbs (as described in this application) are embodiments of EDCs of this invention. More specifically conjugation cyclopamine deriviatives to anti-SMO or anti-Patch mAbs (as described in this application) are further embodiments of EDCs of this invention.

In another embodiment, the invention provides an EDC that comprises an agent, a stable or non-cleavable linker, and a targeting moiety that recognizes the V-ATPase or a protein complexed with V-ATPase protein. The V-ATPase is the primary regulator of the tumor microenvironment, by means of proton extrusion to the extracellular medium. The decrease in extracellular pH confers the cells a resistant, highly invasive and metastatic phenotype. However, the acid medium confers an optimum pH to the degradative enzymes (such as proteases and MMPs) for their proper functioning. Aberrant and/or overexpression of VATPases and/or specific V-ATPase subunits is a signature of many cancers. In normal cells, VATPases are found within intracellular plasma membranes however, there is some evidence to suggest aberrant display of these proton pumps within the extracellular membrane, thereby providing an alteration of extracellular pH. Therefore, EDCs of the invention include those targeting various V-ATPase proteins or proteins that are complexed with V-ATPases associated proteins. V-ATPase small molecule inhibitors are known to provide both anticancer effects and resensitize cancer cells to classical chemotherapeutics. However, existing V-ATPase inhibitors can not discriminate between extracellular versus intracellular V-ATPases and therefore remain highly toxic non-specific agents. Conjugation of V-ATPases inhibitors to V-ATPases mAbs or mAbs to V-ATPase associated proteins (as described in this application) is anticipated to overcome these limitations.

In another embodiment, the invention provides an EDC that comprises an agent, a stable or non-cleavable linker, and a targeting moiety that recognizes CD44/MDR. A correlation between the expression of MDR proteins (such as Pgp or BCRP) and CD44 has been found in various cancer cell lines and these studies also revealed that the two proteins co-localize within the cell membrane. One protein directly influences the expression of the other and disruption of this interaction has profound effects on drug resistance, cell migration, and in vitro invasion. Therefore, EDCs of the invention include those targeting various CD44/MDR proteins or proteins that are complexed with CD44/MDR proteins. It is anticipated that this invention could be used significantly improve existing small molecule MDR reversal agents.

In another embodiment, the invention provides an EDC that comprises an agent, a stable or non-cleavable linker, and a targeting moiety that recognizes the GPCR thyrotropin receptor. Antibodies to the activated state of the thyrotropin receptor coupled to a small molecule agonist through a a stable or non-cleavable linker could be produced to treat hypothyroidism. Monoclonal antibodies have already been generated that function as thyrotropin receptor agonists and small molecule drug (N-(4-(5-(3-(furan-2-ylmethyl)-4-oxo-1,2,3,4-tetrahydroquinazolin-2-yl)-2-methoxybenzyloxy) phenypacetamide) has been determined as a lead for activation of the receptor. The combination of a targeting moiety and agent that both activate heteromers of the thyrotropin receptor complex may lead to a novel method of dual activation using an EDC of the invention. Since the targeting moiety can lock the receptor into a conformation allowing for better binding and activity of the agent. GPCR heteromerization has been found to alter the properties of individual receptors where multiple forms of related receptors exist in a complexes.

The following two tables provide an illustrative list of EDCs of the invention. The first table shows illustrative EDCs (agent and targeting moiety's target) of the invention where the target for both the targeting moiety and agent are on the same molecule and thus, the sites for binding are in close proximity. The second table shows illustrative EDCs (agent, agent's target and targeting moiety's target) of the invention where the target for the targeting moiety and agent are not on the same molecule but in close proximity. The tables also show possible disease indications for which they can be employed.

TABLE 1

EDCs for which the targets of the targeting moiety and the agent are the same.

| Targets | Agents | Illustrative Antibodies | Therapeutic Indications |
|---|---|---|---|
| Smoothen (SMO) | cyclopamine analogs, statins, itraconazole, LDE225, BMS 833923, GDC-0449, purmorphamine, SANT1, Cur-61414, SAG, IPI-926, 1-amino-4-arylphthalazines | | cancer, tissue regeneration |
| MCT1 | AR-C117977, ARC155858, DIDS, luteolin, phloretin, quercetin, gamma-hydroxybutyric acid, alpha-cyano-4-hydroxycinnamic acid, lonidamide | | arthritis, tissue transplantation, cancer |
| Integrins (alphaV-beta3, alpha5-beta1, alpha6-beta4, alpha4-beta1, alpha5-beta6, alphaV-beta5) | integrin inhibitors, RGD peptides, EMD 121974 (Cilengitide), S36578, S247, S137, PSK1404 | ReoPro, Tysabri, Ambegrin, Vitaxin (anti-alphaVbeta3) | Osteoporosis, cancer |
| Eph receptors | | | |
| S1P Receptors 1-5 | SEW 2871 -agonist<br>W146 antagonist<br>FTY720-P | Cancer<br>Graft Rejection | Cancer<br>Immunosuppreion<br>Graft Rejection and multiple sclerosis |
| Plexins | semaphorins | | Cancer |
| nAChR | alpha-Cobratoxin | | Cancer |
| Eag-1 | quinidine | | Cancer |
| CXCR4/fusin | AMD3100 | | Stem Cell Mobilization |
| CCK-2 Receptor | L365-260 | sc-16177 | Cancer/Diabetes |
| SGLT-2 | Dapagliflozin (BMS-512148), 189075 (GW-189075), 869682 (GW-869682), AVE-2268, KGT-1681, KGT1251, TS-033, YM-543, T-1095 (see Isaji, M. *Curr. Opin. Invest. Drugs* 2007, 8, 285-292 for additional examples) | | Diabetes |
| SERT/SLC6A4 Anti-Serotonin Transporter | Fluoxetine serotonin | | psychiatric disorders |
| PGDF-beta receptors | Sonnoside B | | Cancer |
| Sphingosine-1-phosphate Receptors S1P1 | CYM 5442 | | Cancer |
| Insulin Receptor | Miniglucagon | | Severe reactive hypoglycemia |
| GLUT transporters (exemplified by GLUT1 and GLUT4) | 2-deoxyglucosamine, dipyridalone, flavonoids, isoflavones, phloretin, phlorizin, imatinib, gefitinib (see Amann, T.; Hellerbrand, C. *Exp. Opin. Ther. Targets* 2009, 13, 1411-1427 for additional examples) | | Cancer, diabetes, HTLV |
| GLP-1 | 2-(2-methyl)thiadiazolylsufanyl-3-triflouromethyl-6,7-dichloroquinoxaline | | diabetes |
| ABO+ | methyltryptophan | | Cancer |
| Class B GPCR | | | Cancer |
| Vacuolar ATPase (V-ATPase) | Proton pump inhibitors (e.g., omeprazole, esomeprazole, lansoprazole, pantoprazole, rabeprazole) concanamycin, bafilomycins, higrolidins, chondropsins, salicylihalamides, lobatamides, concanamycin, plecomacrolides, benzolactone enamides, archazolids, chondropsins and indoles, benzolactone enamides (salicylihalamide), lobatamide A and B. apicularen, indolyls, oximidine, macrolactone archazolid, lobatamide C, and cruentaren. The latest generation of inhibitors includes NiK12192, FR202126, and PPI SB 242784 | | Cancer |

TABLE 2

EDCs for which the targets of the targeting moiety and the agent are different.

| Targeting Moeity's Target | Agent's Target | Agent | Indications |
|---|---|---|---|
| Gamma-subunit of Na,K-ATPase, beta-subunit of Na,KATPase | Alpha-subunit of Na,K-ATPase | Cardiac glycoside and derivatives CEN-09-106, CEN-09-107, ivermectins, gramadicins, istaroximes | Cancer Inflammation |

TABLE 2-continued

EDCs for which the targets of the targeting moiety and the agent are different.

| Targeting Moeity's Target | Agent's Target | Agent | Indications |
|---|---|---|---|
| CD147 | MCT1 | AR-C117977, ARC155858, DIDS, luteolin, phloretin, quercetin, gamma-hydroxybutyric acid, alpha-cyano-4-hydroxycinnamic acid | arthritis, tissue transplantation, cancer |
| Patched | SMO | cyclopamine analogs, statins, itraconazole, LDE225, BMS 833923, GDC-0449, purmorphamine, SANT1, Cur-61414, SAG, !PI-926, 1-amino-4-arylphthalazines | cancer, tissue regeneration |
| Patched, SMO | Shh | robotokinin | cancer, tissue regeneration |
| urokinase-type plasminogen activator (uPAR, CD87) | integrins (alphaVbeta3, alpha5-beta1, alpha6-beta4, alpha4-beta1, alpha5-beta6, alphaV-beta5) | integrin inhibitors, RGD peptides, EMD 121974 (Cilengitide), S36578, S247, S137, PSK1404 | Cancer |
| urokinase-type plasminogen activator (uPAR, CD87) | MMP | MMP inhibitors (see Cancer Metastasis Rev. 2006, 25, 115-136 for representative examples) | cancer, tissue regeneration, clotting, thrombosis |
| integrins (alphaV-beta3, alpha5-beta1, alpha6-beta4, alpha4-beta1, alpha5-beta6, alphaV-beta5) | MMP | MMP inhibitors (see Cancer Metastasis Rev. 2006, 25, 115-136 for representative examples) | cancer, tissue regeneration, clotting, thrombosis |
| urokinase-type plasminogen activator (uPAR, CD87) | heparanase | heparanase inhibitors | cancer, tissue regeneration, clotting, thrombosis |
| integrins (alphaVbeta3, alpha5-beta1, alpha6-beta4, alpha4-beta1, alpha5-beta6, alphaV-beta5) | heparanase | heparanase inhibitors | cancer, tissue regeneration, clotting, thrombosis |
| integrins (alphaV-beta3, alpha5-beta1, alpha6-beta4, alpha4-beta1, alpha5-beta6, alphaV-beta5) | urokinase-type plasminogen activator (uPAR, CD87) | Peptide antagonist NH2-DXFSRYLWS | Cancer Biochem Soc Trans 2002 Apr; 30(2): 177-83 |
| CFTR | Beta-2-adenergic receptor | Beta blockers | gloucoma |
| Plexin B1 | Neuropilin-1 | semaphorins | |
| LRP5 or 6 | Wnt | 5-thiophene pyrimidines, | Type-1 diabetes |
| CD44 | MDR proteins (e.g., BCRP, Pgp) | MDR reversal agents (e.g., verapamil) | Cancer |
| thyrotropin receptor | Thyrotropin heteromer | Thyrotropin mimetic, (N-(4-(5-(3-(furan-2-ylmethyl)-4-oxo-1,2,3,4-tetrahydroquinazolin-2-yl)-2-methoxybenzyloxy)phenyl)acetamide) | hypothyroidism | target for the targeting moiety and agent are not on the same molecule)

Table 1 EDCs are useful, for example and without limitation, in cases where agents are effective yet the specificity of the agent is such that off target side effects, low activity, poor pharmacokinetics, drug resistance (e.g. MDR mediated drug resistance) or other problems exist and where attaching a targeting moiety to a stable linker shows improved therapeutic effect. Table 1 EDCs also include those in which the agent and the targeting moiety work synergistically to enhance the desired therapeutic effect.

Table 2 EDCs are useful, for example and without limitation, in cases where better specificity for the agent is desirable. This is the case when the agent's target may exist on many different types of normal cells and diseased cells but only as a complex or in close proximity with the targeting moiety's target on diseased or cells of interest. Table 2 EDCs also include those in which the agent and the targeting moiety work synergistically to enhance the desired therapeutic effect.

EDCs of the invention also include those that comprise a targeting moiety that recognizes a portion or subunit or isoform of the target antigen that are found preferentially on cells in or near the diseased targeted tissue area. These target antigens include those that are mutated, differentially expressed or aberrantly glycosylated proteins (relative to those same proteins in normal tissue) in the diseased or targeted tissue area.

In other embodiments, the EDCs are generally useful for research purposes. In various embodiments of the invention, the EDCs are generally useful for the treatment of cancer or cystic fibrosis. Examples of diseases for cancer treatment include breast cancer, colorectal cancer, liver cancer, lung cancer, prostate cancer, ovarian cancer, brain cancer, and pancreatic cancer. Specifically, treatment for one of the following tumor types can be effected: B-cell lymphoblastic leukemia, T-cell lymphoblastic leukemia, lymphoma, including Hodgkin's lymphoma and non-Hodgkin's lymphoma, follicular lymphoma, Burkitt lymphoma, melanoma, ocular melanoma, cutaneous melanoma, colon adenocarcinomas, hepatocellular carcinomas, renal cell carcinoma, ovarian carcinoma, prostate adenocarcinoma, liver carcinoma, transitional cell carcinoma, pancreatic adenocarcinoma, lung carcinoma, breast carcinoma, and colon carcinoma.

VI. PEPTIDES AND ANTIBODIES

In one embodiment, the invention provides a purified polypeptide, the amino acid sequence which comprises, consists essentially of or consists of SEQ ID NO: 1. In another embodiment, the invention provides a purified polypeptide comprising at least 10 consecutive residues of SEQ ID NO: 1. In another embodiment, the invention provides a purified polypeptide comprising an immunogenic domain comprising at least 10 consecutive residues of SEQ ID NO: 1. In another embodiment, the invention provides a purified polypeptide comprising an amino acid sequence which comprises SEQ ID NO: 1 with 0 to about 20 conservative amino acid substitutions. In another embodiment, the invention provides a purified polypeptide that binds specifically to an antibody that binds specifically to SEQ ID NO: 1. In another embodiment, the invention provides a single-stranged nucleic acid that hybridizes under physiological conditions to a probe having the sequence of SEQ ID NO: 1.

In another embodiment, the invention provides a purified antibody that binds specifically to FXYD5. In another embodiment, the invention provides a purified antibody that selectively binds to an epitope within the polypeptide represented by SEQ ID NO: 1 of FXYD5. In another embodiment, the invention provides a purified antibody that binds to FXYD5 or to an epitope within the polypeptide represented by SEQ ID NO: 1 of FXYD5 and inhibits binding of FXYD5 to its receptor. In another embodiment the invention provides a purified antibody that binds to the antigen recognized by the M53 antibody. In another embodiment the invention provides a purified antibody that binds to the epitope on FXYD5 recognized by the M53 antibody. In another embodiment the invention provides a purified antibody that binds to the antigen recognized by the M53 antibody and competes for binding with the M53 antibody. In another embodiment, the invention provides a purified antibody to FXYD5 that binds selectively to cancer cells (e.g. lung cancer cells), but not to normal cells (e.g. normal lung cells). In these above embodiments, the antibody may be monoclonal or polyclonal, humanized or fully human. On one embodiment, antibodies as disclosed herein are useful as an antidote to treatment with an EDC composed of an antibody to FXYD5 linked to a therapeutic agent.

VII. PHARMACEUTICAL FORMULATIONS

The administration of the compounds according to the invention can be done by any of the administration methods accepted for the therapeutic agents and generally known in the art. These processes include, but are not limited to, systemic administration, for example by parenteral, oral, nasal, or topical administration. Parenteral administration is done generally by subcutaneous, intramuscular or intravenous injection, or by perfusion. In general, antibody based therapeutics are typically administered intravenously. The injectable compositions can be prepared in standard forms, either in suspension or liquid solution or in solid form that is suitable for an extemporaneous dissolution in a liquid. In one embodiment, parenteral administration uses the installation of a system with slow release or extended release that ensures the maintenance of a constant dose level. For intranasal administration, it is possible to use suitable intranasal vehicles that are well known to those skilled in the art. The oral administration can be done by means of tablets, capsules, soft capsules (including formulations with delayed release or extended release), pills, powders, granules, elixirs, dyes, suspensions, syrups and emulsions. This form of presentation is more particularly suited for the passage of the intestinal barrier.

The dosage for the administration of compounds according to the invention is selected according to a variety of factors including the type, strain, age, weight, sex and medical condition of the subject; the severity of the condition to be treated; the method of administration; the condition of the renal and hepatic functions of the subject and the nature of the particular compound or salt that is used. A normally experienced doctor will easily determine and prescribe the effective amount of the desired compound to prevent, disrupt or stop the progress of the medical condition that is to be treated. By way of examples, when given parenterally, the effective levels of the compounds according to the invention will be in the range of from about 0.002 to about 500 mg per kg of body weight, more particularly from about 0.02 mg to about 50 mg per kg of body weight and administered daily, weekly, or biweekly. The compounds according to the invention can be administered in the form of single daily doses, or the total daily dosage can be administered in two, three, four or more doses per day. More specifically, the dosage can in some embodiments be similar in the range of 1-20 mgs/meter squared (mgs/m$^2$) body surface area (bsa), and the doses can be administered weekly or every two weeks. For solid tumors the dosage may in some embodiments be higher, e.g., an initial dose in the range of 200 to 600 mgs/m$^2$ bsa or ~1 to 20 mgs/kg (given, e.g., through a 120-minute intravenous infusion) and 150-350 mgs/m$^2$ or 1-10 mgs/kg (given through 60-minute intravenous infusion). Therefore the dosing range of the compounds according to the invention can be daily to weekly dosages of 1 mgs/m$^2$ to 500 mgs/m$^2$ bsa.

The compositions according to the invention can be sterilized and/or can contain one or more of: non-toxic adjuvants and auxiliary substances such as agents for preservation, stabilization, wetting or emulsification; agents that promote dissolution; and salts to regulate osmotic pressure and/or buffers. In addition, they can also contain other substances that offer a therapeutic advantage. The compositions are prepared, respectively, by standard processes of mixing, granulation or coating well known to those skilled in the art.

The compounds of the invention herein can be administered concurrently, sequentially, or alternating with the second drug or upon non-responsiveness with other therapy. Thus, the combined administration of a second drug includes co-administration, using separate formulations or a single pharmaceutical formulation, and consecutive administration in either order, wherein preferably there is a time period while both (or all) therapies simultaneously exert their biological activities. Multiple second drugs may be used in combination the compounds of the invention.

In another embodiment of the invention, articles of manufacture containing materials useful for the treatment of the disorders described above are provided. In one aspect, the article of manufacture comprises (a) a container comprising the compounds herein (preferably the container comprises the EDC and a pharmaceutically acceptable carrier or diluent within the container); and (b) a package insert with instructions for treating the disorder in a patient.

Also provided herein are methods for assessing the activity of an EDC of the invention. In one method, a targeting moiety can be used to recognize the target of the targeting moiety of the invention, but most preferably it is one of those disclosed herein. One of these methods is a method of assessing the presence of the antibody's target of the invention comprising subjecting patient tissue from tumors (such as lung cancer, but including all tumor types) to the targeting moiety alone of the EDC and analyzing binding by immunohistological methods which are known in the art. One method for assessing the activity of an EDC of the invention in tumor tissue comprises subjecting patient tissue from a tumor to fluorescent resonance transfer to determine whether the agent's and targeting moiety's targets are within close proximity. In this method the targeting moiety is labeled with one fluorophore and an agent target specific antibody (or similar) labeled with another fluorophore can absorb energy of a specific wavelength and re-emit energy at a different (but equally specific) wavelength. Another method for assessing the activity of the EDC in tumor tissue comprising subjecting patient tissue from tumors (such as lung cancer, but including all tumor types) treated with the EDC to FDG-PET imaging and then determining if the targeting moiety alone inhibits FDG uptake into the tissue. Inhibition of FDG uptake correlates with delayed tumor growth in this method by the EDC of the invention. Methods for carrying out the imaging and determining if FDG uptake is inhibited are known in the art.

Therapeutic EDCs of the invention may be administered by any route appropriate to the condition to be treated. The EDC will typically be administered parenterally, i.e. infusion, subcutaneous, intramuscular, intravenous, intradermal, intrathecal, bolus, intratumor injection or epidural (Shire et al (2004) J. Pharm. Sciences 93(6):1390-1402). Pharmaceutical formulations of EDCs are typically prepared for parenteral administration with a pharmaceutically acceptable parenteral vehicle and in a unit dosage injectable form. An EDC having the desired degree of purity is optionally mixed with pharmaceutically acceptable diluents, carriers, excipients or stabilizers, in the form of a lyophilized formulation or an aqueous solution (Remington's Pharmaceutical Sciences (1980) 16th edition, Osol, A. Ed.).

Acceptable parenteral vehicles, diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference. An exemplary formulation of an EDC contains about 100 mg/ml of trehalose (2-(hydroxymethyl)-643,4,5-trihydroxy-6-(hydroxymethyptetrahydropyran2-ylloxy-tetrahydropyran-3,4,5-triol; $C_{12}H_{22}O_{11}$; CAS Number 99-20-7) and about 0.1% TWEEN™ 20 (polysorbate 20; dodecanoic acid 21243,4-bis(2-hydroxyethoxy)tetrahydrofuran2-yl]-2-(2-hydroxyethoxy)et-hoxy]ethyl ester; $C_{26}H_{50}O_{10}$; CAS Number 9005-64-5) at approximately pH 6.

Pharmaceutical formulations of a therapeutic EDC may contain certain amounts of unreacted drug moiety (D), antibody (or other targeting moiety)-linker intermediate (Ab-L), and/or drug-linker intermediate (D-L), as a consequence of incomplete purification and separation of excess reagents, impurities, and by-products, in the process of making the EDC; or time/temperature hydrolysis or degradation upon storage of the bulk EDC or formulated EDC composition. For example, it may contain a detectable amount of drug-linker or various intermediates. Alternatively, or in addition to, it may contain a detectable amount of the unlinked free targeting moiety. An exemplary formulation may contain up to 10% molar equivalent of the agent of agent linker as it was determined by the in vitro cellular proliferation assays that in some cases the drug-linker conjugate less potent in cell killing than free drug.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the EDC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions contain the active materials (EDC) in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl phydroxybenzoate, one or more coloring agents, one or more flavoring agents and one or more sweetening agents, such as sucrose or saccharin.

The pharmaceutical compositions of EDC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 .mu.g of the active ingredient per milliliter of solution in order that infusion of a suitable volume at a rate of about 30 mL/hr can occur. Subcutaneous (bolus) administration may be effected with about 1.5 ml or less of total volume and a concentration of about 100 mg EDC per ml. For EDC that require frequent and chronic administration, the subcutaneous route may be employed, such as by pre-filled syringe or autoinjector device technology.

As a general proposition, the initial pharmaceutically effective amount of EDC administered per dose will be in the range of about 0.01-100 mg/kg, namely about 0.1 to 20 mg/kg of patient body weight per day, with the typical initial range of compound used being 0.3 to 15 mg/kg/day. For example, human patients may be initially dosed at about 1.0 mg EDC per kg patient body weight. The dose may be escalated to the maximally tolerated dose (MTD). The dosing schedule may be about every 3 weeks, but according to diagnosed condition or response, the schedule may be more or less frequent. The dose may be further adjusted during the course of treatment to be at or below MTD which can be safely administered for multiple cycles, such as about 4 or more.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are generally disfavored due to poor bioavailability due to limited absorption, hydrolysis or denaturation in the gut, formulations of EDC suitable for oral administration may be prepared as discrete units such as capsules, cachets or tablets each containing a predetermined amount of the EDC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered pa renterally, orally or by any other desired route.

It is contemplated that the EDCs of the present invention may be used to treat various diseases or disorders, such as cancer and autoimmune conditions in human or animal subjects. In one embodiment, the subject is a human. In another embodiment, the subject is a nonhuman animal (e.g dog, cat, horse, bird, etc.) Exemplary conditions or disorders include benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders.

The EDC compounds which are identified in the animal models and cell-based assays can be further tested in tumor-bearing higher primates and human clinical trials. Human clinical trials can be designed similar to the clinical trials testing efficacy. The clinical trial may be designed to evaluate the efficacy of an EDC in combination with known therapeutic regimens, such as radiation and/or chemotherapy involving known chemotherapeutic and/or cytotoxic agents (Pegram et al (1999) Oncogene 18:2241-2251). In one embodiment, the combination therapeutic agent is selected from Bevacizumab; Carboplatin; Cisplatin; Cyclophosphamide; Docetaxel injection; Doxorubicin; Etoposide; Etoposide Phosphate; Gemzar (gemcitabine HCL); Hycamtin (topotecan hydrochloride); Ifosfamide; Iressa (gefitinib); Irinotecan injection; Methotrexate injection; Mitomycin; Paclitaxel; Photofrin, QLT; Premetrexed; Procarbazine; Streptozocin; Tarceva (erlotinib); Vinblasine; Vincristine; and Vinorelbine tartrate.

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

For the prevention or treatment of disease, the appropriate dosage of an EDC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 .mu.g/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 .mu.g/kg to 100 mg/kg or more, depending on the factors mentioned above. An exemplary, dosage of EDC to be administered to a patient is in the range of about 0.1 to about 10 mg/kg of patient weight.

An EDC of the invention may be combined in a pharmaceutical combination formulation, or dosing regimen as combination therapy, with a second compound having anticancer properties. The second compound of the pharmaceutical combination formulation or dosing regimen preferably has complementary activities to the EDC of the combination such that they do not adversely affect each other.

The second compound may be a chemotherapeutic agent, cytotoxic agent, cytokine, growth inhibitory agent, anti-hormonal agent, aromatase inhibitor, protein kinase inhibitor, lipid kinase inhibitor, anti-androgen, antisense oligonucleotide, ribozyme, gene therapy vaccine, antiangiogenic agent and/or cardioprotectant. Such molecules are suitably present in combination in amounts that are effective for the purpose intended. A pharmaceutical composition containing an EDC may also have a therapeutically effective amount of a chemotherapeutic agent such as a tubulin-forming inhibitor, a topoisomerase inhibitor, or a DNA binder.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

In one embodiment, treatment with an EDC of the present invention involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and doxetaxel) and/or anthracycline antibiotics. Preparation and dosing schedules for such chemotherapeutic agents may be used according to manufacturers's instructions or as determined empirically by the skilled practitioner. Preparation and dosing schedules for such chemotherapy are also described in Chemotherapy Service Ed., M. C. Perry, Williams & Wilkins, Baltimore, Md. (1992).

The anticancer agent may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide an effect achieved when the active ingredients used together is greater than the sum of the effects that results from using the compounds separately. The effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, an effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Also falling within the scope of this invention are the in vivo metabolic products of the EDC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products may be identified by preparing a radiolabelled EDC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the EDC compounds.

Metabolites include the products of in vivo cleavage of the EDC where cleavage of any bond occurs that links the drug moiety to the antibody. Metabolic cleavage may thus result in the naked antibody, or an antibody fragment. The antibody metabolite may be linked to a part, or all, of the linker. Metabolic cleavage may also result in the production a drug moiety or part thereof. The drug moiety metabolite may be linked to a part, or all, of the linker.

In another embodiment, an article of manufacture, or "kit", containing EDC and materials useful for the treatment of the disorders described above is provided. The article of manufacture comprises a container and a label or package insert on or associated with the container. Suitable containers include, for example, bottles, vials, syringes, or blister pack. The containers may be formed from a variety of materials such as glass or plastic. The container holds an EDC composition which is effective for treating the condition and may have a sterile access port (for example the container may be an intravenous solution bag or a vial having a stopper pierceable by a hypodermic injection needle). At least one active agent in the composition is an EDC. The label or package insert indicates that the composition is used for treating the condition of choice, such as cancer. For example, the cancer may be one which overexpresses one of the targets of the EDC of the invention. The label or package insert may also indicate that the composition can be used to treat cancer, wherein the cancer is not characterized by overexpression of one of the targets of the EDC of the invention. In other embodiments, the package insert may indicate that the EDC composition can be used also to treat hormone independent cancer, prostate cancer, colon cancer or colorectal cancer.

The article of manufacture may comprise a container with a compound contained therein, wherein the compound comprises an EDC of the present invention. The article of manufacture in this embodiment may further comprise a package insert indicating that the EDC can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Further advantages and characteristics of the invention will emerge from the following Examples, given by way of illustration and which are not to be construed as limiting, and in which reference will be made to the accompanying drawings. It will be clear that the invention may be practiced otherwise than as particularly described in the foregoing Examples. Numerous modifications and variations of the present invention are possible in light of the above teachings and, therefore, are within the scope of the appended claims following these Examples. The Examples are divided into an Agent Synthesis section, an Antibody section and an EDC section.

Agent Synthesis

Example 1

Synthesis of Linker Ready Therapeutic Agents and Biotin

To show that illustrative compounds of the invention are useful at targeting and killing tumor cells, therapeutic agents with activity toward the Na,K-ATPase were synthesized and then coupled to Na,K-ATPase specific antibodies via non-cleavable linkers. The agents were synthesized with active groups which could be coupled to non-cleavable linkers. The agents can also be used as controls to test agent activity when not coupled to antibodies via the linkers.

Glycinyl hydrazone of scillarenone (CEN09-104) was prepared as follows and used in Example 3.

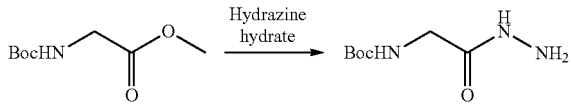

[(tert-Butyloxycarbonyl)amino]acetyl-hydrazine. N-Boc-glycine methyl ester (2.12 g, 10.87 mmol) and hydrazine hydrate (3.2 g, 54.34 mmol) were stirred for 2 hours at reflux. The solvent was removed under reduced pressure and the crude was purified by flash chromatography (CH$_2$Cl$_2$/MeOH, 90:10), the NMR data agreed with literature. (Borg, S.; Estenne-Bouhtou, G.; *J. Org. Chem.* 1995, 60, 3112-3120).

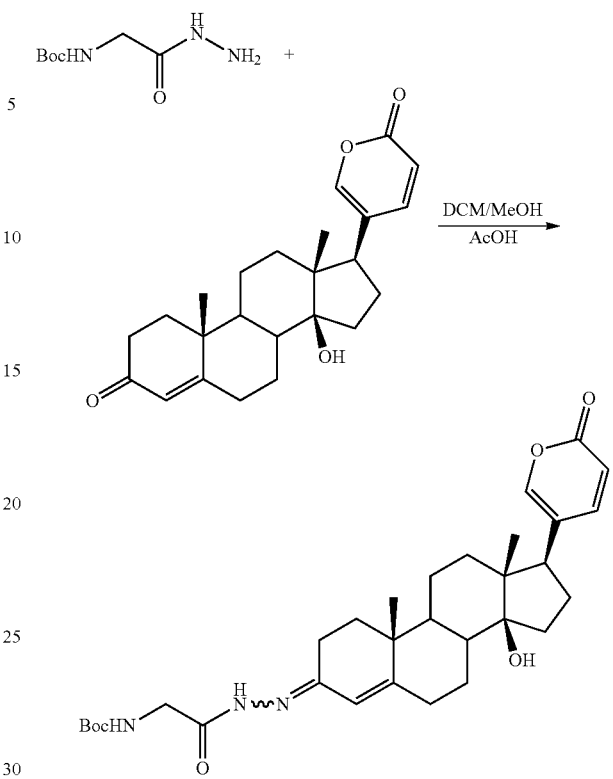

[(tert-Butyloxycarbonyl)amino]acetyl-hydrazone of scillarenone. Scillarenone was prepared as described in PCT App. No. U.S. Ser. No. 09/153,159 (Pub. No. 2010/017480; see Example 3), incorporated herein by reference. [(tert-Butyloxycarbonyl)amino]acetyl-hydrazine (1.4 g, 7.4 mmol) and scillarenone (1.4 g, 3.7 mmol) were dissolved in methanol (10 mL) and dichloromethane (20 mL). AcOH (0.2 mL) was added. The reaction was stirred for 20 hours at room temperature. The solvent was removed under reduced pressure. The residue was purified by flash chromatography (DCM/MeOH, 95:5) to afford [(tert-Butyloxycarbonyl)amino]acetyl-hydrazone of scillarenone as a yellow powder (2.05 g, 100%). $^1$H-NMR (300 MHz, CDCl$_3$) δ 0.72 (s, 3H), 1.02-2.60 (m, 31H), 3.84 (d, 1H, J=5.7 Hz), 4.25 (d, 1H, J=4.0 Hz), 5.79 (s, 1H), 6.24 (dd, 1H, J=9.7, 0.6 Hz), 7.20-7.21 (m, 1H), 7.80 (dd, 1H, J=9.7, 2.5 Hz); $^{13}$C-NMR (75 MHz, CDCl$_3$) δ 16.6, 18.1, 19.1, 21.8, 27.8, 28.4, 28.5, 28.7, 29.8, 32.1, 32.8, 32.9, 34.9, 38.0, 40.6, 42.8, 48.3, 49.6, 51.1, 51.2, 77.2, 77.4, 85.1, 115.5, 121.1, 122.7, 146.8, 148.7, 162.2

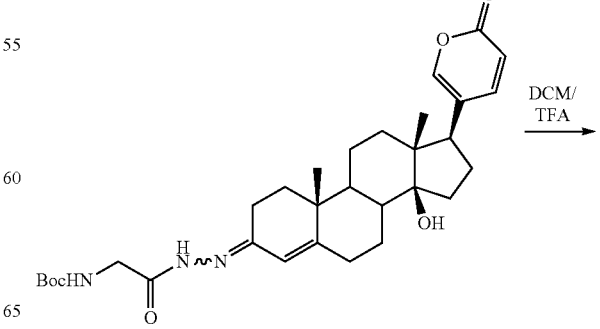

-continued

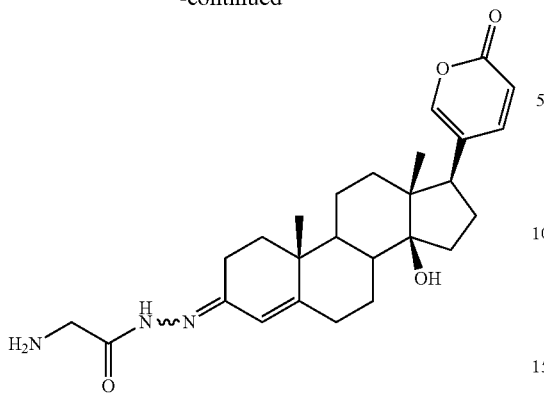

CEN09-104 also named glycinyl hydrazine of scillarenone. [(tert-Butyloxycarbonyl)amino-acetyl]hydrazone of scillarenone (2 g, 3.61 mmol) was dissolved in dichloromethane (25 mL). Trifluoroacetic acid (11 mL) was added dropwise at 0° C. The reaction was stirred for 2 hours at 0° C. to produce the TFA salt (MW=566). Solvent was removed under reduced pressure (1.39 g, 85%). $^1$H-NMR (300 MHz, CD$_3$OD) δ 0.76 (s, 3H), 1.10-1.26 (m, 5H), 1.42-1.81 (m, 8H), 1.94-2.49 (m, 7H), 2.54-2.59 (m, 1H), 2.64-2.77 (m, 1H), 3.82 (d, 1H, J=5.5 Hz), 4.08 (d, 1H, J=3.8 Hz), 5.83 (s, 1H), 6.29 (dd, 1H, J=9.7, 0.6 Hz), 7.43-7.44 (m, 1H), 8.00 (dd, 1H, =9.7, 2.4 Hz)

CEN08-243 or also named scillarenin neo-4-amino-4-deoxy-L-xylopyranoside was prepared using 4-(N-trifluoroacetyl)-amino-4-deoxy-L-xylopyranose and scillarenone as described in PCT application No. US09/53159 and used in Example 4.

CEN09-107 or Scillarenin-4-amino-4-deoxy-L-ribopyranoside was prepared as follows and used in Example 4.

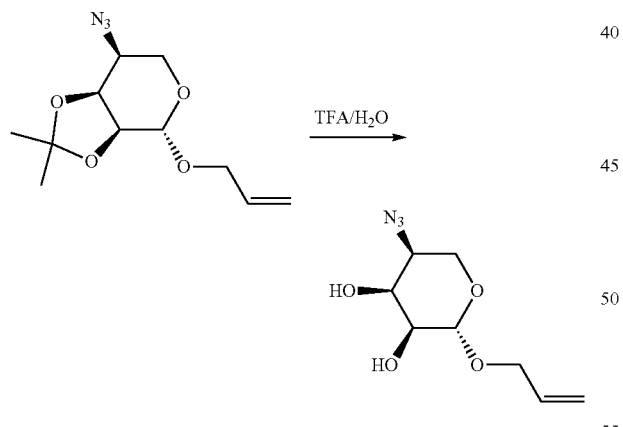

1-Allyl-4-azido-4-deoxy-L-ribopyranoside. 1-Allyl-2,3-0-isopropylidene-4-azido-4-deoxy-L ribopyranoside (8.53 g, 33.6 mmol) was dissolved in TFA/H$_2$0 (80:20, 40 mL). The reaction mixture was stirred for 30 min at 0° C. The solvents was removed under reduced pressure and the resulting residue was purified by flash chromatography (CH$_2$Cl$_2$/MeOH, 95:5) to give 1-allyl4-azido-4-deoxy-L-ribopyranoside as brown oil (26.3 g, 72%) R$_f$ 0.5 (CH$_2$Cl$_2$/MeOH, 95:5); $^1$H-NMR (300 MHz, CD$_3$OD) δ, 3.49 (dd, 1H, J=5.1, 3.5 Hz, H-2), 3.58 (ddd, 1H, J=6.7, 3.9, 3.2 Hz, H4), 3.75 (dd, 1H, J=11.6, 6.7, H-5b), 3.83 (dd, 1H, J=11.6, 3.9 Hz, H-5a), 4.05 (ddt, 2H, J=1.4, 6.0, 13.0 Hz, CH$_2$—CH=CH$_2$), 4.09 (dd, 1H, J=3.2 Hz, H-3), 4.23 (ddt, 1H, J=1.5, 5.2, 13.0 Hz, CH$_2$—CH=CH$_2$), 4.70 (d, 1H, J=5.1 Hz, H-1), 5.17 (ddd, 1H, J=1.4, 2.9, 10.4 Hz, CH$_2$=CH), 5.30 (ddd, 1H, J=1.7, 3.4, 17.3 Hz, CH$_2$=CH), 6.00-5.87 (m, 1H, CH$_2$=CH).

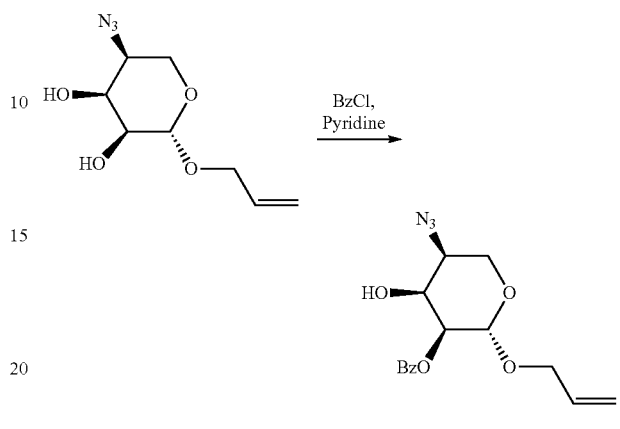

1-Allyl-2-O-benzoyl-4-azido-4-deoxy-L-ribopyranoside. 1-Allyl-4-azido-4-deoxy-L-ribopyranoside (4.0 g, 18.6 mmol) was dissolved in dry dichloromethane (120 mL) under argon. Pyridine (4.5 mL, 55.76 mmol) was added and the mixture was stirred for 30 min at −30° C. BzCl (2.25 mL, 19.51 mmol) was then added drop wise. It was then stirred overnight at room temperature. The solvent was removed under reduced pressure. The resulting residue was dissolved in EtOAc, washed with water, 0.1N HCl and brine. The organic layer was dried over Na$_2$SO$_4$, filtered and concentrated. The crude product was purified by flash chromatography (Toluene/EtOAc, 95:5 to 90:10) to give 1-ally)-2-0-benzoyl-4-azido-4-deoxy-L-ribopyranoside as brown oil (4.46 g, 75%) R$_f$ 0.45 (Toluene/EtOAc, 90:10). $^1$H-NMR (300 MHz, CD$_3$OD) δ, 3.77-3.86 (m, 2H, H-4, H-5b), 3.96 (dd, 1H, I=2.8, 11.7 Hz, H-5a), 4.02-4.10 (m, 1H, CH$_2$—CH=CH$_2$), 4.204.27 (m, 1H, CH$_2$—CH=CH$_2$), 4.36 (dd, 1H, J=3.4 Hz, H-3), 4.95 (d, 1H, J=3.9 Hz, H-1), 5.15-5.33 (m, 2H, CH$_2$=CH), 5.85-5.98 (m, 1H, CH$_2$=CH), 7.47-7.53 (m, 2H, H—Ar), 7.59-7.65 (m, 1H, H—Ar), 8.10-8.17 (m, 2H, H—Ar); $^{13}$C-NMR (75 MHz, CD$_3$OD) δ 60.1 (C-4), 62.3 (C-5), 67.7 (C-3), 70.1 (CH$_2$—CH=CH$_2$), 73.1 (C-2), 98.7 (C-1), 117.7 (CH$_2$=CH), 129.65 (C—Ar), 131.1 (C—Ar), 134.6 (CH$_2$=CH), 135.6 (C—Ar), 167.7 (C=0).

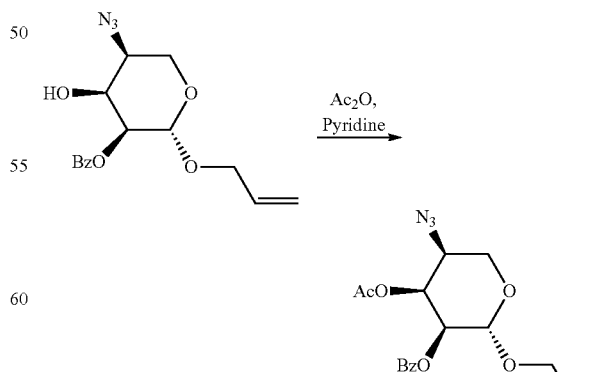

1-Allyl-3-0-acetyl-2-0-benzoyl-4-azido-4-deoxy-L-ribopyranoside. 1-Allyl-2-0-benzoyl-4-azido-4-deoxy-L-ribopyranoside (4.45 g, 13.93 mmol) was dissolved in anhydrous pyridine (5.6 mL, 69.65 mmol) at 0° C., under argon and Ac₂O was added drop wise. The mixture was stirred overnight at room temperature. Dichloromethane was then added; the organic layer was washed with water, 0.1 N HCl and brine, dried over Na₂SO₄, filtered and concentrated. The crude product was purified by flash chromatography (Toluene/EtOAc, 90:10) to give 1-allyl-3-0-acetyl-2-0-benzoyl-4-azido-4-deoxy-L-ribopyranoside as a yellow oil (5.03 g, 100%) R$_f$ 0.50 (Toluene/EtOAc, 90:10); ¹H-NMR (300 MHz, CDCl3) δ 2.01 (s, 3H), 3.81 (dd, 1H, J=12.4, 3.1 Hz, H-5b), 3.92-3.95 (m, 1H, H-4), 4.00-4.06 (m, 2H, H-5a, CH₂—CH=CH₂), 4.21 (ddt, 1H, J=12.8, 5.3, 1.4 Hz, CH₂—CH=CH₂) 4.96 (d, 1H, J=2.6 Hz, H-1), 5.18-5.34 (m, 2H, H-2, CH₂—CH=CH₂), 5.51 (dd, 1H, J=3.77 Hz, H-3), 5.82-5.95 (m, 1H, CH=CH₂), 7.42-7.48 (m, 2H), 7.55-7.60 (m, 1H), 8.12-8.15 (m, 2H); ¹³C-NMR (75 MHz, CDCl3) δ 20.8 (CH₃) 56.8 (C-4), 61.2 (C-5), 68.6 (C-3), 68.7 (C-2), 69.0 (CH₂=CH—), 97.5 (C-1), 118.3 (CH₂—CH=CH₂), 128.7 (C—Ar), 129.7 (C—Ar), 130.2 (C—Ar), 133.4 (C—Ar), 133.6(CH₂=CH), 166.0 (C=O), 169.9 (C=O).

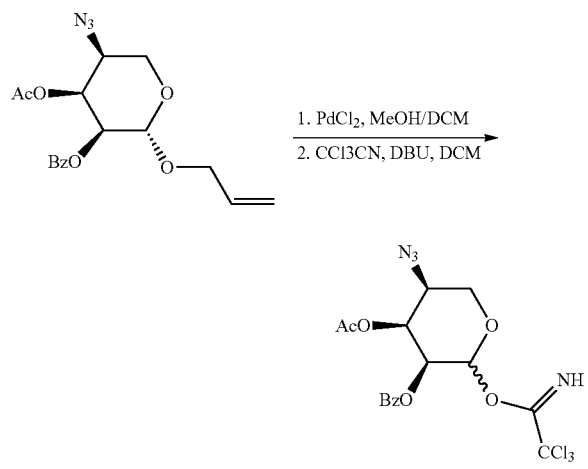

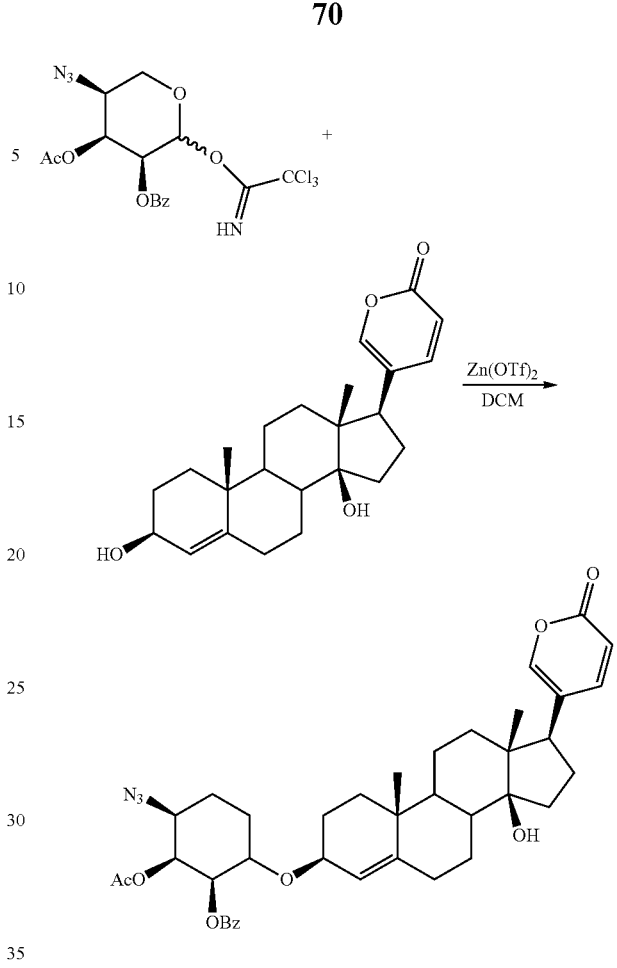

1-Trichloroacetimido-3-0-Acetyl-2-0-benzoyl-4-azido-4-deoxy-L-ribopyranoside. 1-Allyl-3-0-acetyl-2-0-benzoyl-4-azido-4-deoxy-L-ribopyranoside (5.03 g, 13.93 mmol) was dissolved in dichloromethane/methanol (40 mL, 90:10) under argon and PdCl₂ (0.5 g, 2.6 mmol) was added. The reaction mixture was stirred overnight at room temperature. The mixture was filtered through a pad of Celite and concentrated under reduced pressure. The residue was filtered through a pad of silica gel (hexane/EtOAc, 80:20 to 50:50). The resulting compound (2 g, 6.22 mmol) was dissolved in dry DCM (50 mL) under argon and the solution was cooled to 0° C. CCl₃CN (6.24 mL, 62.2 mmol) was added, followed by dropwise addition of DBU (0.46 mL, 3.11 mmol). The reaction was stirred for 2 hours at 0° C. The solvent was removed under reduced pressure. The crude product was taken up in hexanes-EtOAc (60:40) and filtered through a pad of silica gel (hexane/EtOAc, 60:40 to 40:60) to afford 1-trichloroacetimido-3-0-Acetyl-2-0-benzoyl-4-azido-4-deoxy-L-ribopyranoside as a white gum (1.7 g, 26%) This material was carried forward without further purification. R$_f$ 0.55 (hexane/EtOAc, 50:50).

Scillarenin-3-0-Acetyl-2-0-benzoyl-4-azido-4-deoxy-L-ribopyranoside. To a suspension of activated 4A molecular sieves (160 mg) in dry dichloromethane (60 mL0 at 0° C. under argon was added a solution of 1-trichloroacetimido-3-0-acetyl-2-0-benzoyl-4-azido-4-deoxy-Lribopyranoside (5.03 g, 13.93 mmol) in the minimum amount of dry dichloromethane. Scillarenin (0.7 g, 1.825 mmol) was added and after 5 minutes at 0° C., Zn(OTf)₂ (0.133 g, 0.365 mmol) was added. The reaction mixture was stirred for 30 minutes at 0° C. Another 0.5 eq of scillarenin (0.7 g, 1.825 mmol) was added. The reaction mixture was stirred for an additional period of 30 minutes at 0° C. The reaction was quenched with few drops of Et₃N. The mixture was filtered and the solvent was removed under reduced pressure. The crude product was purified by flash chromatography (hexane/EtOAc, 60:40 to 40:60) to afford scillarenin-3-0-Acetyl-2-0-benzoyl-4-azido-4-deoxy-L-ribopyranoside as a white solid (1.64 g, 65%) R$_f$ 0.39 (hexane/EtOAc, 50:50). ¹H-NMR (300 MHz, CDCl₃) δ 0.72 (s, 3H), 1.03-2.20 (m, 24H), 2.42-2.48 (m, 1H), 3.82 (dd, 1H, J=12.4, 3.1 Hz, H-5b), 3.94-3.97 (m, 1H), 4.12 (dd, 1H, J=12.4, 2.4 Hz, H-5a), 4.17-4.22 (m, 1H), 5.10 (d, 1H, J=2.6 Hz, H-1), 5.26 (dd, 1H, J=2.8 Hz, H-2), 5.31 (s, 1H), 5.53 (dd, 1H, J=3.75 Hz, H-3), 6.24-6.27 (m, 1H), 7.22 (d, 1H, J=1.6 Hz), 7.44-7.49 (m, 2H), 7.56-7.61 (m, 1H), 7.82 (dd, 1H, J=9.7, 2.6 Hz,), 8.13-8.16 (m, 2H); ¹³C-NMR (75 MHz, CDCl₃) δ 16.4, 18.9, 20.6, 21.2, 25.2, 28.5, 28.6, 32.2, 32.6, 35.0, 37.5, 40.6, 42.7, 48.2, 50.1, 51.0, 56.7 (C-4), 60.9 (C-5), 67.7 (C-3), 69.1 (C-2), 73.6, 85.0, 96.2 (C-1), 115.3, 121.2, 121.6, 128.5, 129.5, 129.9, 133.3, 146.7, 147.5, 148.5, 162.3 (C=O), 165.9 (C=O), 169.7 (C=O).

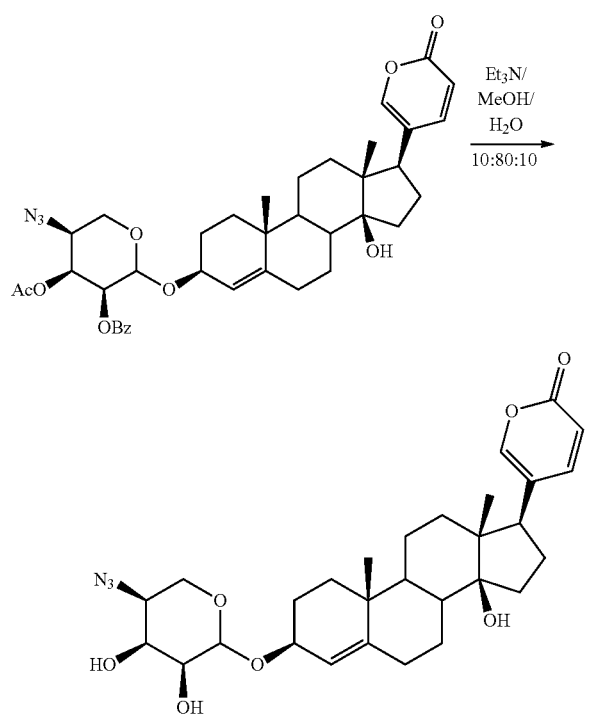

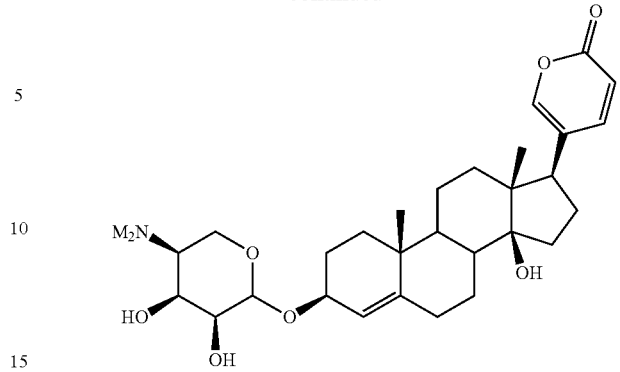

Scillaren in-4-azido-4-deoxy-L-ribopyranoside. Scillaren in-3-0-acetyl-2-0-benzoyl-4-azido-4-deoxy-L-ribopyranoside (1.61 g, 2.34 mmol) was dissolved in methanol (20 mL. Et₃N (2.5 mL) and H₂O (2.5 mL) were added. The reaction mixture was stirred overnight at room temperature. The solvent was removed under reduced pressure. The crude was purified by flash chromatography (CH₂Cl₂/MeOH, 90:10) to afford scillarenin-4-azido-4-deoxy-L-ribopyranoside as a white solid (0.93 g, 73%) R$_f$ 0.25 (CH₂Cl₂/MeOH, 90:10); ¹H-NMR (300 MHz, CD₃OD) δ 0.74 (s, 3H), 1.06-2.22 (m, 21H), 2.52-2.57 (m, 1H), 3.42 (dd, 1H, J=5.4, 3.2 Hz, H-2), 3.54-3.59 (m, 1H, H-4), 3.72-3.89 (m, 2H, H-5a, H-5b), 4.09-4.12 (m, 1H, H-3), 4.16-4.21 (m, 1H), 4.81 (d, 1H, J=5.4 Hz, H-1), 5.34 (s, 1H), 6.28 (dd, 1H, J=9.7, 0.7 Hz), 7.42-7.43 (m, 1H), 7.99 (dd, 1H, J=9.7, 2.6 Hz,); ¹³C-NMR (75 MHz, CD₃OD) δ 17.3, 19.5, 22.4, 26.5, 29.8, 30.0, 33.2, 33.5, 36.5, 38.7, 41.7, 43.4, 49.6, 51.6, 52.1, 60.5 (C-4), 62.1 (C-5), 69.6 (C-3), 72.0 (C-2), 75.5, 85.7, 100.4 (C-1), 115.4, 123.1, 125.0, 148.4, 149.3, 150.5, 164.8 (C=O).

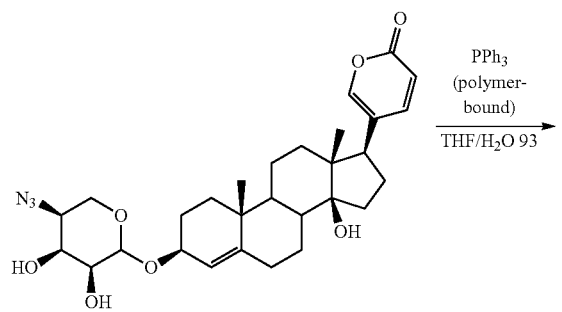

CEN09-107 also named scillarenin-4-amino-4-deoxy-L-ribopyranoside. Scillarenin-4-azido-4-deoxy-L-ribopyranoside (1.61 g, 2.34 mmol) was dissolved in THF/H₂O (30 mL, 90:10). PPh₃ polymer-bound (2.34 g, 3 mmol·g⁻¹) was added. The mixture was stirred for 6 hours at 40° C. The mixture was filtered and the solvent was removed under reduced pressure. The crude was purified by flash chromatography (CH₂Cl₂/MeOH, 90:10 to 80:20) to afford scillarenin-4-amino-4-deoxy-L-ribopyranoside as a yellow powder (0.67 g, 73%) R$_f$ 0.1 (CH₂Cl₂/MeOH1, 80:20); ¹H-NMR (300 MHz, DMSO-d₆)) δ 0.63 (s, 3H), 0.96-2.10 (m, 21H), 2.43-2.46 (m, 1H), 2.90-2.92 (m, 1H, H-4), 3.29 (dd, 1H, J=3.3 Hz, H-2), 3.45 (dd, 1H, J=11.4, 5.4 Hz, H-5b), 3.63-3.68 (m, 2H, H-3, H-5a), 4.02-4.08 (m, 1H), 4.69 (d, 1H, J=4.2 Hz, H-1), 5.24 (s, 1H), 6.29 (dd, 1H, J=9.7, 0.7 Hz), 7.48-7.58 (m, 1H), 7.92 (dd, 1H, J=9.7, 2.5 Hz,); ¹³C-NMR (75 MHz, (CD₃)₂S0) δ 16.6, 18.6, 20.9, 25.2, 28.4, 28.5, 31.8, 31.9, 34.8, 37.0, 39.7, 41.5, 47.8, 49.6, 49.9, 50.8 (C-4), 63.7 (C-5), 67.1, 71.2 (C-3), 72.3 (C-3), 83.1, 99.1 (C-1), 114.2, 122.2, 122.6, 146.1, 147.3, 149.2, 161.3 (O=O).

Scillarenin-4-amino-4-deoxy-L-xylopyranoside (CEN09-106) was prepared as follows and used in Examples 5, 6, 7, and 8.

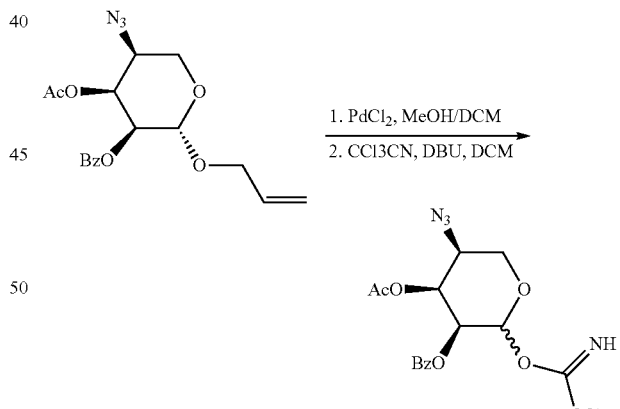

2,3-di-O-benzoyl-4-azido-4-deoxy-L-xylopyranoside-1-Trichloroacetimidate. 1-Allyl-2,3-di-O-benzoyl-4-azido-4-deoxy-L-ribopyranoside (11.9 g, 28.1 mmol) was dissolved in dichloromethane/methanol (80 mL, 90:10) under argon and PdCl₂ (0.5 g, 2.8 mmol) was added to the solution. The mixture was stirred overnight at room temperature, filtered through a pad of Celite and concentrated under reduced pressure. The residue was filtered through a pad of silica gel (hexane/EtOAc, 70:30). The resulting compound (8.38 g, 21.83 mmol) was dissolved in dry dichloromethane (170 mL) under argon. CCl₃CN (21.9 mL, 218.3 mmol) was added, followed by dropwise addition of DBU (1.63 mL, 10.91 mmol) at 0° C. The reaction was stirred for 0° C. The solvent was removed under reduced pressure. The crude product was filtered through a pad of silica gel (hexane/EtOAc, 60:40 to 40:60) to afford 2,3-di-O-benzoyl-4-azido-4-deoxy-L-ribopyranosid-1-trichloroacetimidate as a yellow oil (9.7 g, 65%). The compound was carried forward without further purification. $R_f$ 0.37 (silica gel, hexane/EtOAc, 80:20).

CDCl$_3$) δ 16.7, 19.0, 21.4, 25.8, 28.7, 28.8, 32.4, 32.8, 35.2, 37.6, 40.8, 42.9, 48.4, 50.2, 51.2, 59.2, 63.1, 71.6, 72.9, 76.1, 85.2, 100.0, 115.5, 121.7, 122.8, 128.5, 128.6, 129.1, 129.5, 129.9, 130.1, 133.4, 133.6, 146.9, 147.6, 148.7, 162.5, 165.3, 165.7.

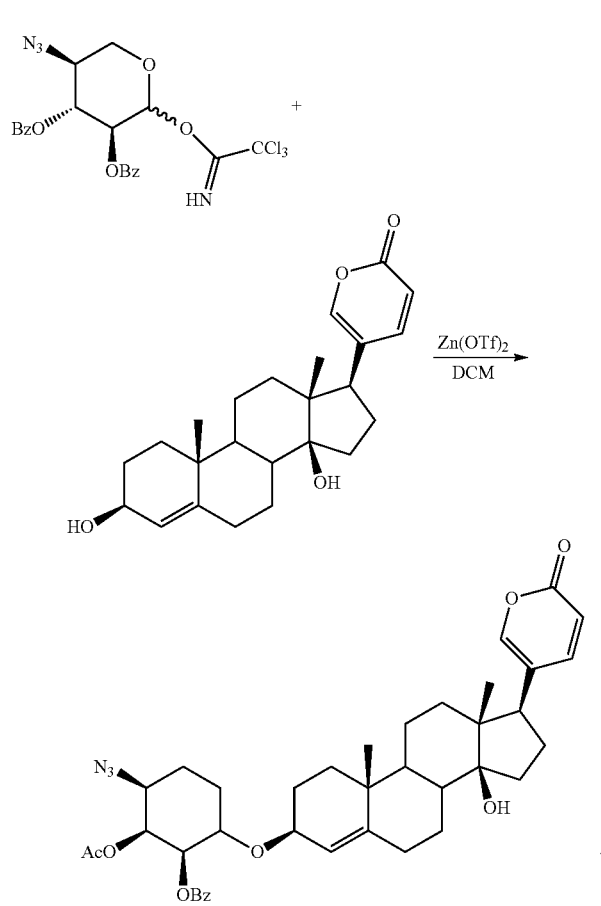

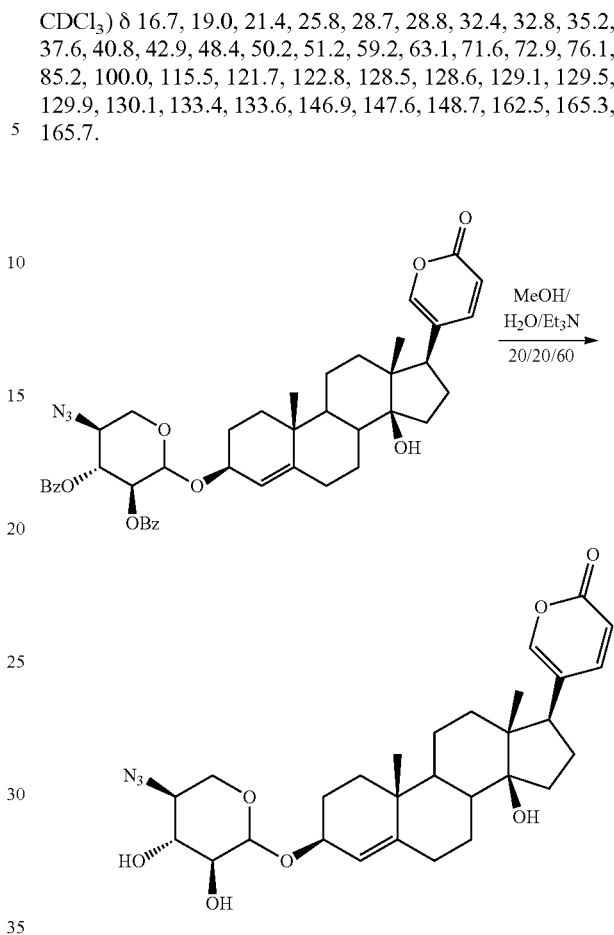

Scillarenin-2,3-di-O-benzoyl-4-azido-4-deoxy-L-xylopyranoside. 2,3-di-O-benzoyl-4-azido-4-deoxy-L-xylopyranoside-1-trichloroacetimidate (0.483 g, 0.915 mmol) was added to a suspension of activated 4A molecular sieves (90 mg) in dry dichloromethane (15 mL) under argon at 0° C. Scillarenin (0.182 g, 0.474 mmol) was then added to the mixture. After 5 minutes, Zn(OTf)$_2$, (17 mg, 0.047 mmol) was added and the reaction mixture was stirred for an additional 30 minutes at 0° C. An additional amount of scillarenin (0.182 g, 0.474 mmol) was added. The reaction mixture was stirred for 30 minutes at 0° C. The reaction was quenched with few drops of Et$_3$N. The mixture was filtered and the solvent was removed under reduced pressure. The crude product was purified by flash chromatography (hexane/EtOAc, 75:25 to 50:50) to afford scillarenin-2,3-di-O-benzoyl-4-azido-4-deoxy-L-xylopyranoside as a white powder (0.521 g, 76%) $R_f$ 0.35 (silica gel, hexane/EtOAc, 50:50). $^1$H-NMR (300 MHz, CDCl$_3$) δ, 0.68 (s, 3H), 0.90-2.17 (m, 21H), 2.39-2.44 (m, 1H), 3.47 (dd, 1H, J=12.0, 9.5 Hz, H-5b), 3.79-3.87 (m, 1H, H-4), 4.17-4.22 (m, 2H, H-5a), 4.78 (d, 1H, J=6.8 Hz, H-1), 5.26 (dd, 1H, J=8.6, 6.8 Hz, H-2), 5.33 (s, 1H), 5.49 (dd, 1H, J=8.7 Hz, H-3), 6.22 (dd, 1H, J=9.7, 0.6 Hz), 7.18-7.19 (m, 1H), 7.33-7.39 (m, 4H), 7.47-7.53 (m, 2H), 7.80 (dd, 1H, J=9.7, 2.6 Hz), 7.92-7.97 (m, 4H); $^{13}$C-NMR (75 MHz, Scillarenin-4-azido-4-deoxy-L-xylopyranoside. Scillarenin-2,3-di-O-benzoyl-4-azido-4-deoxy-L-xylopyranoside (0.351 g, 0.468 mmol) was dissolved in methanol (21 mL). Et$_3$N (7 mL) and H$_2$O (7 mL) were added. The reaction mixture was stirred for 2 days at room temperature. The mixture was filtered and the solvent was stripped under reduced pressure. The crude product was purified by flash chromatography (CH$_2$Cl$_2$/MeOH, 98:2 to 95:5) to afford scillarenin4-azido-4-deoxy-L-xylopyranoside as a yellow powder (40 mg, 24%) $R_f$ 0.31 (CH$_2$Cl$_2$/MeOH, 95:5); $^1$H-NMR (300 MHz, CD$_3$OD) δ, 0.74 (s, 3H), 1.03-2.21 (m, 21H), 2.52-2.57 (m, 1H), 3.12-3.20 (m, 2H), 3.40-3.44 (m, 2H), 3.87-3.92 (m, 1H), 4.17-4.23 (m, 1H), 4.31 (d, 1H, J=7.7 Hz, H-1), 5.35 (s, 1H), 6.28 (dd, 1H, J=9.7, 0.8 Hz), 7.43 (d, 1H, J=1.5 Hz), 7.99 (dd, 1H, J=9.7, 2.6 Hz).

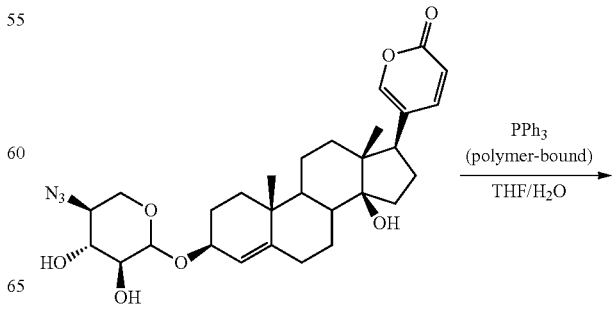

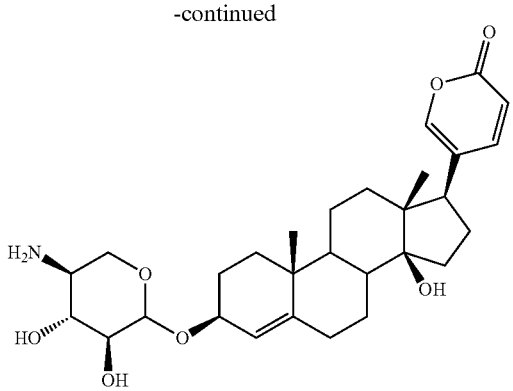

CEN09-106 also named Scillarenin-4-amino-4-deoxy-L-xylopyranoside. Scillarenin-4-azido-4-deoxy-L-xylopyranoside (1.61 g, 2.34 mmol) was dissolved in THF/H$_2$O (2.8 mL, 90:10). PPh3 polymer-bound (79 mg, 3 mmol·g$^{-1}$) was added. The reaction mixture was stirred for 2 hours at 40° C. The mixture was then filtered and the solvent was removed under reduced pressure. The crude product was purified by flash chromatography (CH$_2$Cl$_2$/MeOH, 90:10 to 80:20) to afford scillarenin-4-amino-4-deoxy-L-xylopyranoside as a yellow powder (23 mg, 58%) R$_f$ 0.2 (CH$_2$Cl$_2$/MeOH, 80:20); $^1$H-NMR (300 MHz, CD$_3$OD) δ, 0.74 (s, 3H), 1.06-2.19 (m, 21H), 2.52-2.57 (m, 1H), 2.75-2.86 (m, 1H, H-4), 3.14-3.24 (m, 2H, H-2, H-3), 3.64-3.72 (m, 1H, H-5b), 3.87-3.91 (m, 1H, H-5a), 4.19-4.24 (m, 1H), 4.36 (d, 1H, J=7.1 Hz, H-1), 5.38 (s, 1H), 6.28 (dd, 1H, J=9.7, 0.6 Hz), 7.42 (d, 1H, J=1.6 Hz), 7.99 (dd, 1H, J=9.7, 2.5 Hz); $^{13}$C-NMR (75 MHz, CD$_3$OD) δ 17.4, 19.6, 22.5, 26.8, 29.9, 30.1, 33.3, 33.6, 36.6, 38.8, 41.8, 43.5, 49.4, 51.7, 52.2, 75.3, 76.5, 78.9, 79.3, 79.8, 85.8, 103.7, 115.6, 123.4, 125.1, 148.4, 149.4, 150.5, 164.9.

CEN10-105 also named Mal-PEG24-CEN09-106 was prepared as follows and used in Examples 5, 6, 7 and 8.

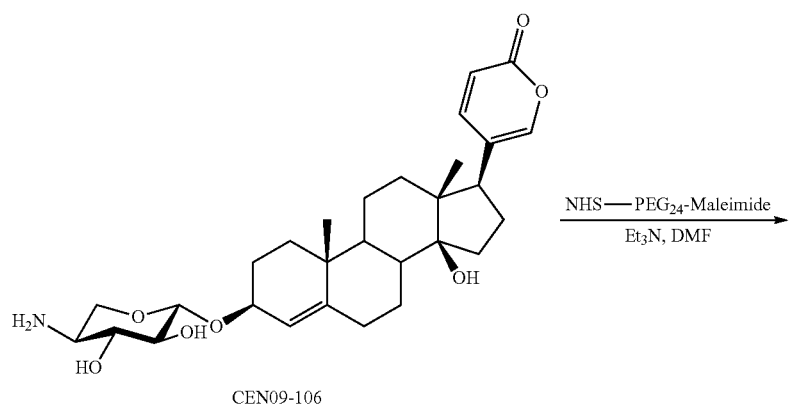

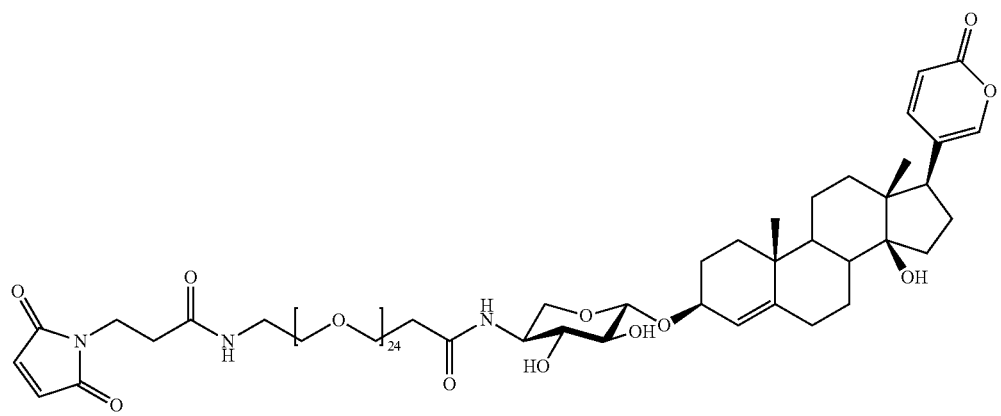

To a solution of CEN09-106 (183 mg, 0.0359 mmol) in DMF (1 mL) at room temperature was added NHS-PEG$_{24}$-Maleimide (50 mg, 0.0359 mmol). Then Et$_3$N (0.025 mL, 0.18 mmol) was added. The reaction was stirred at room temperature for 2 hours. The solvent was removed under reduced pressure. The crude material was purified by flash chromatography (CH$_2$Cl$_2$/MeOH, 95:5 to 80:20) to afford CEN10-105 as a yellow oil (48 mg, 75%) R$_f$ 0.66 (CH$_2$Cl$_2$/MeOH, 80:20). HPLC analysis [Luna C18, 250×4.60 mm, 5 μm, 5% to 95% ACN over 32 minutes, 1 ml·min$^{-1}$] indicated a product which was >95% pure. HRMS-ESI (m/z): calcd for C$_{87}$H$_{147}$N$_3$O$_{35}$ [M+K$^+$]$^+$: 1832.9452. found 1832.9777. The NHS-(PEG)$_n$-maleimide (where n is an integer) can be attached to any amine-bearing molecule (vide infra) using similar reaction conditions.

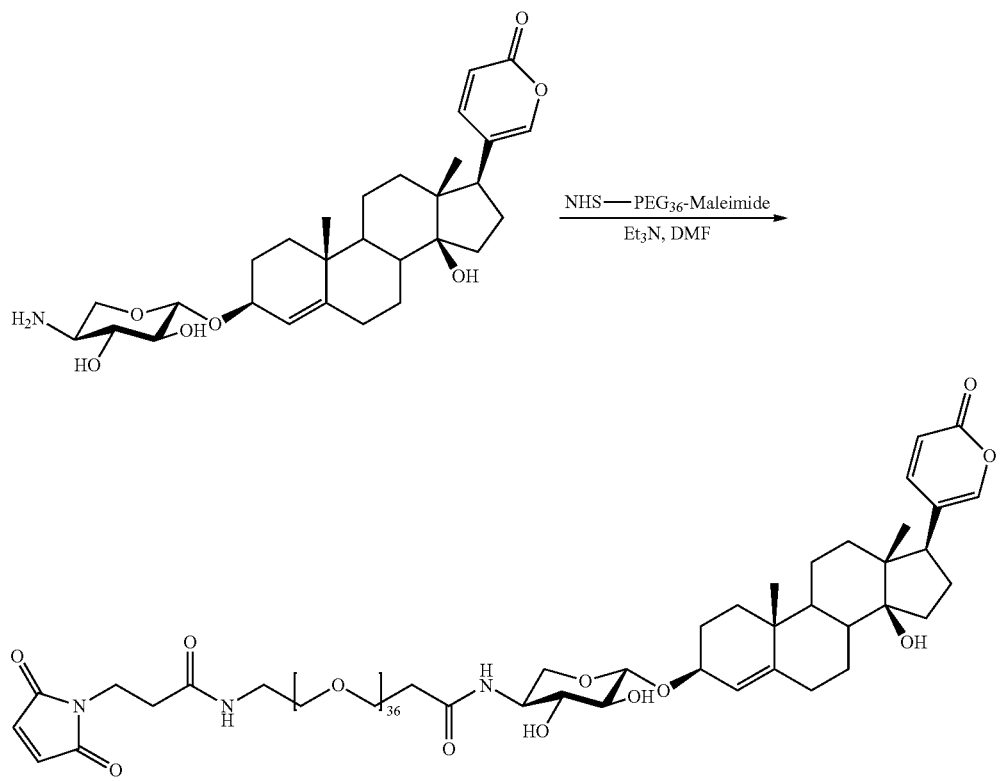

CEN10-131. To a solution of CEN09-106 (26 mg, 0.05 mmol) in DMA (1.5 mL) at room temperature was added NHS-PEG$_{36}$-Maleimide (96 mg, 0.05 mmol), followed by Et$_3$N (0.014 mL, 0.10 mmol). The reaction was stirred at room temperature for 1 hour. The solvant was removed under reduced pressure. The crude material was purified by HPLC (Gemini C$_{18}$, 5 μm, 4.6 mm×250 mm, 30 to 70% ACN, 0.1% TFA; see the chromatogram below) to afford CEN10-131 as oil (24 mg, 21%). Maldi-TOF (m/z): calcd for C$_{111}$H$_{195}$N$_3$O$_{47}$ [M+Na$^+$]$^+$: 2345.2859. found 2345.0769.

Targeting Moiety Section

The antibodies used in Examples 2, 3, 4, 5, 6, 7 and 8 were as follows: 115 (sc-30603 special order without gelatin from Santa Cruz Biotechnologies, Inc.), N20 (sc-30602 special order without gelatin from Santa Cruz Biotechnologies, Inc.), M53 (described in Shimamura et al. J. Clinical Oncology 21(4) 659-667 (2003)), Erb (Erbitux from Imclone Systems, Inc.), and α-FL (31242 from Thermo Scientific). Antibodies L15, N20 and M53 all recognize and bind human FXYD5, Erb recognizes and binds human epidermal growth factor receptor (EGFR) found on the surface of many tumor cell lines, and α-FL recognizes and binds fluorescein. M53 and α-FL are of mouse origin and monoclonal. Erb is a chimeric mouse/human antibody and monoclonal. L15 and N20 are of goat origin and are polyclonal.

Example 2

Mapping of the Epitope to which Antibody M53 Binds

To better understand the recognition of antibodies used for the illustrative compounds of the invention, epitope mapping was conducted. If the genetic sequence or protein sequence is known or determined for the EDC's antibody's target, epitope mapping may allow the pre-use determination of EDC activity. Therefore, where not previously determined, linear epitope recognition of the antibodies used in examples 3, 4, 5, 6, 7 and 8, was determined. Overlapping peptide sequences were synthesized that represent positions 24 through 145 of the extracellular domain of human FXYD5, each peptide was synthesized with a cysteine at its amino terminus to facilitate conjugation to maleimide activated BSA (cat. number: 77116, Pierce Biotechnology). Peptides were coupled to BSA per the manufactures protocol, and any unreacted maleimide groups of the BSA were capped by the addition of L-cysteine. ELISA plates (cat. number: 9017, Corning) were coated with 250 ng of each BSA-peptide in 100 ul of 200 mM carbonate buffer, pH 9.6 overnight at 4° C. Coated ELISA plates were washed 3× with PBS pH 7, blocked 30 min with in PBS pH 7+1% non-fat dry milk (PBS+NFDM), then washed 3× with PBS pH 7. 100 uL of NCC-M53 diluted to 1 ug/mL in PBS+NFDM was added to all wells, incubated for 30 min at room temperature, then washed 3× with PBS pH 7. Goat anti-mouse IgG alkaline phosphatase (cat. number: A1418, Sigma-Aldrich) was diluted 1:15,000 in PBS+NFDM then added in 100 uL to each well, incubated 30 min at room temperature, then washed 3× with PBS pH7. PNPP (cat. number: Pierce Biotechnology) at 1 mg/mL in 1M DEA with 50 mM MgCl2, pH 9.8 added to each well at 100 uL per well, incubated 30 minutes at room temperature and the absorbance at 450 nm was read for each well. Results showed that M53 binds an epitope contained within Seq ID 1.

```
Q96DB9[22-145], FXYD domain-containing ion transport regulator 5,
Homo sapiens
                                                       Seq ID 1
        10         20         30         40         50         60
MSPSGRLCLL TIVGLILPTR GQTLKDTTSS SSADSTIMDI QVPTRAPDAV YTELQPTSPT 70         80         90        100        110        120
PTWPADETPQ PQTQTQQLEG TDGPLVTDPE THKSTKAAHP TDDTTTLSER PSPSTDVQTD 130        140        150        160        170
PQTLKPSGFH EDDPFFYDEH TLRKRGLLVA AVLFITGIII LTSGKCRQLS RLCRNHCR
```

Preparing Targeting Moieties for Conjugation.

Selective conjugation of antibodies through sulfhydryl residues first requires antibody disulfide reduction. This was carried out using one of two methods. In one method, termed BME, 2-Mercaptoethanol was used, and for the second method, termed TCEP, tris(2-carboxyethyl)phosphine was used. Each is described below and was used in various examples to prepare antibodies for coupling. The TCEP method is generally the preferred method.

For antibody reduction using the BME method, 1 mg (β-ME is added to 1 mg of antibody and mixed in 500 ul 0.1 M sodium phosphate, 0.15 M NaCl, 5 mM EDTA and incubated at 37° C. for 1.5 hr. Excess β-ME is removed by gel filtration using Sephadex G-25 or similar. The final solution is brought to 1 ml in PBS.

For antibody reduction using the TCEP method, each antibody was treated with 8 molar equivalents of tris(2-carboxyethyl)phosphine (TCEP) (cat. number: HR2-651, Hampton Research) in 20 mM sodium phosphate pH 7, 150 mM NaCl, and 1 mM diethylenetriamine pentaacetic acid (DTPA) (MP Biomedical LLC) for 2 h at 37° C. Reactions were placed in an ice bath and once cooled; linker-agents were added as discussed.

Targeting Moiety Linker Agent Conjugation and Screening

In this section, all EDCs were constructed using PEG24 linker SM(PEG)24-[Part number 22114 Thermo Scientific] unless otherwise noted. Multiple linkers were not used in any of the examples to link agents or biotin. Sometimes linkers are depicted as dashed lines between the antibody designation and the agent or biotin.

Example 3

Production and Testing of Antibody-Linker-Biotin Conjugates

To demonstrate that the agent linking chemistry performs and does not interfere with antibody binding, biotin was first coupled to antibodies via the same conditions and non-cleavable bifunctional PEG24 linker employed to couple the agents used in Example 4 to show EDC activity. First, linker SM(PEG)24 [Thermo Scientific product number 22114] was attached to EZ-Link Amine-PEG2-Biotin [Thermo Scientific—product number 21346] followed by coupling to BME reduced antibodies. The antibody-biotin conjugates were then tested for binding to cells and peptide of sequence 24-39 of Seq ID 1.

Coupling Linker to Biotin.

1.9 mg of EZ-Link Amine-PEG2-Biotin were dissolved in 100 ul of DMSO to obtain a 50 mM solution. 2 ul of a 250 mM stock of linker SM(PEG)24 was added to 98 ul of DMSO to obtain a 5 mM solution. 50 ul of the 5 mM linker solution were added to 50 ul of the 50 mM Biotin-NH2 solution and di-isopropyl ethylamine (final 58 mM) and incubated for 30 minutes at room temperature to produce a 2.5 mM solution of the linker-biotin.

Coupling Linker-Biotin to Antibody.

5 ul of the 2.5 mM linker-biotin solution were added to 100 ug of the BME reduced antibody in 100 ul PBS and incubated for 2 hours at room temperature. Non-reacted CG-NH2 (biotin-NH2) and uncoupled linker-biotin was removed from coupled antibody-linker-biotin by gel filtration using Sephadex G-25 or similar.

Testing antibody-linker-biotin binding to peptide. The synthetic peptide representing amino acids 24 through 39 of FXYD5 (Seq ID No. 1) was coupled to maleimide activated BSA (cat. number: 77116, Pierce Biotechnology). Wells of white opaque 96 well tissue culture treated plates (cat. number: 3917, Corning) were coated at 0.5 ng per well of this conjugate in 200 mM carbonate buffer, pH 9.6 overnight at 4° C. An ELISA plate (as prepared above) was washed 3× with PBS pH 7, then blocked 30 min with 1% BSA in PBS pH 7. Dilution curves of the biotinylated forms of antibodies L15, N20 and anti-FI (negative control) were prepared in 1% BSA in PBS pH 7; then, 100 uL of each were applied to the washed and blocked ELISA plate. After a 30 min incubation at room temperature (RT) the plate was washed 3× with PBS pH 7; then, 100 uL of a 55 ng/mL solution of streptavidin-HRP conjugate (cat. number: 21130, Pierce Biotechnology) in 1% BSA in PBS pH 7 were added to each well and allowed to incubate 30 min at RT. Following incubation, the plate was washed 4× with PBS pH 7, then 100 uL of chemiluminescent substrate (cat. number: 37075, Pierce Biotechnology) were added to each well, the plate shaken 60 seconds, and then read immediately for luminescence using a Wallac Victor II 1420-041 multi-label plate reader. FIG. 1 shows the results of the relative binding experiment. The relative binding affinity, defined as the concentration giving the half-maximal RLU, was calculated as 38.2 nM and 3.75 nM for biotinylated L15 and N20 (respectively).

The results in FIG. 1 show that antibodies L15 and N20, when coupled to biotin via the same linker and coupling conditions used to make the EDCs in Example 4, bind to FXYD5 peptide sequence, indicating that conjugation does not interfere with antibody binding.

Testing Antibody-Linker-Biotin Binding to Cells.

5000 A549 cells per well of a 96-well tissue culture plate were grown at 37 degrees Celsius at 7% CO2 for 24 hours in growth media RPMI with 10% FCS to exponential growth. Growth media was removed and the cells washed 1× with 200 uL PBS, pH 7.4, then fixed in 100 uL methanol (−10° C.). The methanol was removed and the cells allowed to dry at room temperature. The dried cells were then incubated with 100 uL PBS pH 7.4+1% BSA for 20 min at RT, and PBS removed by aspiration. To the wells, 100 ul of antibody-linker-biotin was added at the following concentrations; 100 pM=0.75 ngs Ab, 1 nM, 10 nM, 100 nM. The wells were then washed 3 times with PBS pH 7.4+1% BSA and 100 uL of a 1:20,000 dilution of High Sensitivity Streptavidin-HRP (Pierce) in PBS pH 7.4+1% BSA was added, and incubated 30 min at RT. Wells were washed again 3 times with PBS pH 7.4+1% BSA and 100 uL of SuperSignal ELISA Femto Maximum Sensitivity Chemiluminescent Substrate was added and mixed 1 min on microplate shaker. Luminescence of each well was measured.

The results, shown in FIG. 2, demonstrate that antibodies M53, L15, N20 and Erbitux, when coupled to biotin via the same linker and coupling conditions used to make the EDCs in Example 4, bind to the non-small cell lung cancer cell line A549, indicating that conjugation does not interfere with binding of the antibody to the cells expressing surface antigen targets. Taken together, the results of this example show that coupling antibodies to the PEG24 linker and a small molecule does not interfere with antibody specific recognition.

Example 4

Production and Testing of Antibody-Linker-Agent Conjugates

In this example, polyclonal antibody mixtures were used to demonstrate that illustrative compounds of the invention are useful at targeting and killing tumor cells. To produce EDCs of the invention, therapeutic agents with expected activity toward the Na,K-ATPase were covalently attached to polyclonal antibody mixtures with specificity to FXYD5 through non-cleavable PEG24 linkers and compared to ADCs containing antibodies to targets not in close proximity to the agents' target. The agents alone, the polyclonal antibodies with linker only (no agent), and the antibody-linker-agent conjugates were tested for their ability to disrupt the viability of A549 cells in culture. The results shown in FIGS. 3 through 6 demonstrate that the EDCs are active at disrupting cell viability at various concentrations. The results also show that the reduced antibodies with attached linker without agent, are inactive at the concentrations tested, thus demonstrating that the antibodies require the agent to show activity. The results also show that different agents with different structures and activities can be used and that different polyclonal antibodies raised to different epitopes of the same target can be used in accordance with the invention. The results also show that antibodies to targets on the cells but not within close proximity to the agent's target are not active, indicating simultaneous binding of the antibody and agent is required.

Coupling Linker to Agent.

10 ul of 60 mM stocks of agent were added to 2 ul of a 250 mM stock of linker in DMSO and 10 ul of a 100 mM stock of diisopropylethylamine in DMSO were brought to a volume of 100 ul and incubated for 30 minutes at room temperature to produce a 5 mM solution of linker coupled agent. To produce antibodies with linkers and no agent, ethanolamine a capping agent was used in place of agent.

Coupling Linker-Agent to Antibody.

14 ul of the linker-agent solution was added to 500 ug of the BME reduced antibody and incubated for 1 hour at room temperature. Non-reacted linker-agent and was removed from coupled antibody-linker-agent by gel filtration using Sephadex G-25 or similar.

In vitro cell proliferation assays. EDCs of the invention and comparative compounds were assayed in three cancer cell lines to confirm cytotoxic activity. All cell lines were maintained in complete media [RPMI medium 1640 supplemented with 10% (wt/vol) fetal bovine serum and Gentamycin (50 mg/ml)]. Cells were plated at a density of 5,000 cells per well of each 96-well black tissue culture treated microtiter plate in 95 ul complete media, then were grown for 24 hour at 37° C. with 7% CO2 in a humidified incubator before agent/conjugate addition. In a separate 96-well plate, agent (in DMSO) and antibody conjugate (in PBS) stocks were serially diluted in complete media at 20× final working concentrations, and 5 ul added to the cells used in the assay. Doxorubicin was used as the control to monitor the behavior of the cell lines used. Cells were incubated with the agent/conjugate for 2 days before luminescence reading. Cell viability testing used the CellTiter-Glo luminescent cell viability assay (Promega, Madison, Wis.).

The experiments which produced the results shown in FIG. 3 through FIG. 6 were run to test whether a polyclonal antibody mixture (prepared by immunizing animals with a FXYD5 specific peptide) would show cytotoxicity on its own and/or when coupled to an agent specific to a target in close proximity to FXYD5. The data in FIG. 3 show that within the testing concentration range, only when the agent CEN09-104 attached through the non-cleavable linker to FXYD5 specific antibodies (L15-CEN09-104) and not when attached to an antibody specific to a target not in close proximity (Erb-EGFR specific antibodies), does the conjugate show A549 cell cytotoxicity. The data also shows that the free agent (CEN09-104) and the FXYD5 specific EDC (L15-CEN09-104) have similar IC50s. The conjugate with Erb antibody shows no detectable cytotoxicity within the testing range. This demonstrates that for any given EDC, the target of the antibody should be within close proximity of the target of the agent. EGFR (a target shown to be on the cells) is not within close proximity of the agent target and thus Erb-CEN09-104 is not active while L15-CEN09-104 is active.

The data in FIG. 4 show that within the testing concentration range, L15 alone (open squares) displayed no A549 cytotoxic activity, while L15 linked to CEN08-243 through the PEG24 linker (L15-PEG24-CEN08-243) and the agent alone do display cytotoxic activity. The data also show that the 1C5Os of the EDC and agent alone are similar, which indicates that the agent is still active when conjugated.

Figure 5:
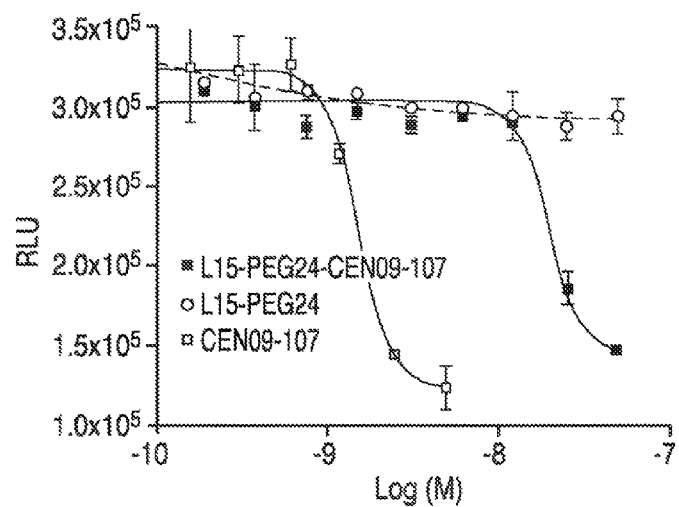
FIG. 5 shows the A549 cytotoxic testing at concentrations indicated. One conjugate, the free agent and a linker attached antibody without agent (L15-) were used. See Example 4.

The data in FIG. 5 shows that within the testing concentration range, FXYD5 specific antibody L15 (open circle) has no effect at killing the A549 cells, yet when the agent CEN09-107 is attached to FXYD5 specific antibody via the non-cleavable linker (closed square), the EDC L15-PEG24-CEN09-107 shows the ability to kill the A549 cells. The data also shows that, unlike the agent (CEN08-243) used to generate the data in FIG. 4, the free agent CEN09-107 is more active when not conjugated to L15. This is similar to the data shown in FIG. 6 when CEN09-107 is linked to different polyclonal antibody mixture (raised to another peptide region on the FXYD5).

The data in FIG. 6 show that within the testing concentration range, FXYD5 specific polyclonal antibody N20 has no effect at killing the A549 cells, yet when the agent CEN09-107 is attached to FXYD5 specific antibody via the noncleavable linker, the EDC produced, L15-PEG24-CEN09-107, shows the ability to kill the A549 cells. The data is similar to that shown in FIG. 5, where the free agent CEN09-107 is more active when not conjugated to a FXYD5 specific polyclonal antibody mixture.

Taken together, the results of Example 4 shown in FIGS. 3-6 demonstrate that, to observe cytotoxic activity of the EDC of the invention, its antibody's target and its agent's target need to be in close proximity, as is the case for FXYD5 and the Na,K-ATPase alpha subunit respectively. The data also demonstrates that therapeutic agents with expected activity toward the Na,K-ATPase show little to no activity when covalently attached to antibodies that bind targets that are not within close proximity to the agents target. These results then indicate simultaneous binding of the antibody and the agent to their respective targets to achieve cytotoxic effects. The example also demonstrates that different agents perform differently when attached to antibodies through the non-cleavable PEG24 linker.

Example 5

Production and Testing of Antibody-Linker-Agent Conjugates

In this example, monoclonal antibody mixtures were used to demonstrate that illustrative compounds of the invention are useful at targeting and killing tumor cells. For this EDC example, the Na,K-ATPase is the target for the agent and FXYD5 is the target for the antibody. Specifically for this example, the EDC was constructed from therapeutic agent CEN09-106, monoclonal antibodies M53 with specificity to FXYD5 (a close proximity target) and the non-cleavable PEG24 linker to produce M53-PEG24-CEN09-106 (sometimes referred to as M53106). M53-PEG24-CEN09-106 was compared in cytotoxicity assays to 1) ADCs containing the agent CEN09-106 covalently attached with a PEG24 linker to monoclonal antibodies Erbitux-106 (EGFR is on the cell surface but not complexed to the Na,K-ATPase complex) or a-Fl-106 (fluorescein is not on the cell surface and not in close proximity to the Na,K-ATPase complex), 2) monoclonal antibodies with specificity to FXYD5 (M53) and 3) the therapeutic agent CEN09-106 covalently attached to the non-cleavable PEG24 linker. The experimental results for this example are shown in FIGS. 7, 8, 9 and 10. The results shown in these figures demonstrate that the conjugates of the invention are active at disrupting cell viability at picomolar to low nanomolar concentrations when the agent and antibody's target are in close proximity on the cell surface. The results also show that, agents attached only to the non-cleavable linker (i.e. not attached to an anti-FXYD5 antibody), are at least 100-fold less active when compared to the EDC constructed for the example. The results also show that the antibodies alone are inactive at the concentrations tested, thus demonstrating that the antibodies require the agent to show activity.

Coupling linker-agent to antibody. Agent CEN09-106 linked to a bifunctional PEG24 linker to produce CEN10-105 was used throughout this Example. To cold TCEP reduced antibody, 9.6 molar equivalents CEN10-105 per equivalent antibody were added. The reaction was allowed to proceed for 30 min on ice. L-Cysteine was then added at a 2-fold excess to CEN10-105 to quench any unreacted maleimide groups. To achieve sample concentration and removal of excess linker-agent that was not coupled to antibody, the conjugation reactions were concentrated then buffer exchanged 3× for 20 mM sodium phosphate pH 7 and 150 mM NaCl using Microcon Ultracel YM-30 (Millipore) 30K cutoff spin concentration devices.

Determination of Drug Loading. Purified antibody concentration was determined using an absorbance value of 1.36 for a 1.0 mg/mL at 260 nm. CEN10-105 (PEG24-CEN09-106) concentration was determined using the extinction co-efficient of 5623 $M^{-1}$ $cm^{-1}$ at 299 nm. EDC loading was determined by first measuring the antibody protein concentration at 260 nm and then measuring the CEN10-105 concentration using extinction co-efficient of 5623 $M^{-1}$ $cm^{-1}$ @ 299 nm and after subtracting the contribution of the antibody absorbance at 299 nm. CEN10-105 loading determined for each antibody-agent conjugate of this example equaled 4.6 for M53, 6.0 for Erb and 6.6 for α-Fl.

In vitro cell proliferation assays. Agents tested in these assays included the antibody drug conjugates, M53-PEG24-CEN09106, Erb-PEG24-CEN09-106, anti-Fl-PEG24-CEN09-106, unconjugated M53, agent with attached linker CEN10-105 (PEG24-CEN09-106) and free agent CEN09-106. Agents were tested on four cancer cell lines to confirm cytotoxic activity. All cell lines were maintained in complete media [RPMI medium 1640 supplemented with 10% (wt/vol) fetal bovine serum and Gentamycin (50 µg/ml)]. Cells were plated at a density of 1250 (H460 and A549) or 1825 (HCT15 and MCF7) cells per well of each 384-well white tissue culture treated microtiter plate in 20 uls complete media, and then were grown for 24 hour at 37° C. with 7% $CO_2$ in a humidified incubator before agent/conjugate addition. In a separate 96-well plate, agent and antibody conjugate (in PBS) stocks were serially diluted in complete media at 5× final working concentrations, and 5 ul added to the cells used in the assay. Cells were incubated with the agent/conjugate for 3 days before cell viability testing. Cell viability testing used the CellTiter-Glo luminescent cell viability assay (Promega, Madison, Wis.). IC50 values of the agents to each cell line were determined using GraphPad Prism 5 software.

|  | H460 | A549 | HCT15 | MCF7 |
| --- | --- | --- | --- | --- |
| M53-PEG24-CEN09-106 | 6.10E−10 | 3.41E−10 | >1.00e−8 | Not detected |
| Erb-PEG24-CEN09-106 | 2.42E−07 | 4.95E−08 | 3.88E−07 | 7.185E−07 |
| α-Fl-CEN09-106 | 2.71E−07 | 1.13E−07 | 3.81E−07 | 9.531E−07 |
| PEG24-CEN09-106 | 1.61E−07 | 7.46E−08 | 2.08E−07 | 3.619E−07 |
| CEN09-CEN09-106 | 1.31E−09 | 5.60E−10 | 2.35E−09 | 1.883E−09 |
| M53 | Not detected | Not detected | Not detected | Not detected |

The Table above shows IC50 values in Molar of drug antibody conjugates and linker-agent conjugates. "Not detected" indicates IC50 values could not be assigned within the given concentration ranges tested.

The data above shows that the strongest cytotoxic agent for these cancer cells lines is the EDC, M53-PEG24-CEN09-106. In cases where the target FXYD5 was determined to be expressed on the cell's surface by immunohistochemistry staining (H460, A549, and HC15 shown in Example 6), data shows that M53-PEG24-CEN09-106 is up to 1000 times more potent then ADCs possessing antibodies to other targets which are on the cell surface (EGFR in the case of Erb-106) but not in close proximity to the agent's target or not on the cell surface at all (Fluorescein in the case of α-Fl. The data also shows that M53-PEG24-CEN09-106 is almost 1000 times more potent then the most likely breakdown product PEG24-106. The data also shows that when FXYD5 is not present on the cell surface, as evidenced by immunohistochemistry staining (H460, A549, and HC15 shown in Example 6, below), M53-PEG24-CEN09-106 activity was not detectable. This demonstrates that the target needs to be present on the cell and in close proximity to the agent's target for the EDC to be active.

For the experiments of this example, the EDC produced was compared to the cysteine capped agent linker PEG24-106 instead of the free active agent CEN09-106. The reason for this is that the main (and perhaps only) breakdown product for the EDC constructed from an antibody, a non-cleavable PEG24 linker and CEN09-106, would be PEG24-106. Other breakdown products could include PEG24-106 with cysteine and other amino acids from the antibody (via protease degradation). Cysteine capped agent linker PEG24-106 could also be a contaminant in the preparation of the EDC described if CEN10-105 is not completely removed during work-up. CEN09-106 is not a likely breakdown product and so is a less preferred control.

The experiments which produced the results in FIG. 7 through FIG. 10 were run to test whether a monoclonal antibody would show cytotoxicity on its own and/or when coupled to an agent specific to a target in close proximity to FXYD5. The data, shown in FIG. 7, demonstrates that within the testing concentration range, FXYD5 specific antibody M53 has no effect at killing the H460 cells. When agent CEN09-106 was attached through a noncleavable linker to produce M53-106, the EDC produced displayed cytotoxic activity against H460 cells in the picomolar range (IC50 6.10E-10 molar). The data also shows that the free agent when conjugated to the non-cleavable linker has similar 1C5Os to the ADCs produced using antibodies to the extracellular target EGFR (Erbitux-106) or antibodies to fluorescein (α-Fl-106), activity is close to 1000× less active at killing the H460 cells than the M53-PEG24-CEN09-106EDC.

The data in FIG. 8 shows that within the testing concentration range, the FXYD5 specific antibody M53 alone does not affect A549 cell growth, yet when M53 is attached to CEN09-106 via the non-cleavable linker to produce M53-PEG24-CEN09-106, strong cytotoxicity activity to kill the A549 cells is observed (IC50 3.41E-10 molar). The data also shows that the free agent when conjugated to the non-cleavable linker has similar IC5Os to the ADCs produced using antibodies to the extracellular target EGFR (Erbitux-106) or antibodies to fluorescein (α-Fl-106) activity is close to 1000× less active at killing the A549 cells than the M53-PEG24-CEN09-106 EDC.

The data in FIG. 9 shows that, within the testing concentration range, the FXYD5 specific antibody M53 alone does not affect HCT15 cell growth, yet when M53 is attached to CEN09-106 via the non-cleavable linker to produce M53-PEG24-CEN09-106, stronger cytotoxicity activity sufficient to kill the HCT15 cells is observed (IC50>1.00e-8 molar). In this experiment, M53-PEG24-CEN09-106 was not tested above 1.00e-8 molar and thus an exact IC50 could not be calculated. The data also shows that when the agent CEN09-106 is conjugated to the non-cleavable linker to generate PEG24-106, or when the agent is conjugated through the non-cleavable linker to anti-EGFR antibodies to generate Erbitux-106, or when the agent is conjugated through the non-cleavable linker to anti-fluorescein antibodies to generate α-Fl-106, similar IC50 values (IC50>1.00e-6 molar) are observed, all of which are close to 100× less active at killing the HCT15 cells than the M53-PEG24-CEN09-106 EDC.

The data in FIG. 10 shows that within the testing concentration range, the FXYD5 specific antibody M53 alone does not affect MCF7 cell growth. The data also shows that for this cell line, which does not express the FXYD5 target (see Example 6, below), EDC M53-PEG24-CEN09-106, ADC Erbitux-106 and ADC α-Fl-106 show similar cell cytotoxicity, as does the agent-linker alone. This indicates that the FXYD5 antibody M53 is not directing the agent to a target (because the target is not present) and that cytotoxicity is dependent on the agent-linker alone.

Taken together, the results in this Example 5 demonstrate that to observe the strongest cytotoxic activity with M53-PEG24-CEN09-106, the antibody and the agent's target need to be present and need to be present in high levels and in close proximity. If the antibody's target is not present on the cell surface the synergistic effect of the antibody with the agent is not observed. FIG. 10 shows that, because MCF7 does not express the FXYD5 target of M53, activity of M53-PEG24-CEN09-106 is no better than the α-Fl-106 activity. The proximity of the antibody's target is also important, because Erb-106 is also not any more effective than α-Fl-106, even though EGFR is present on A549 cells (FIG. 2). In accordance with the invention, these results indicate simultaneous binding of the antibody and the agent to their respective targets are required to achieve maximum cytotoxic effects.

Example 6

Immunohistochemistry of Anti-FXYD5 M53 Antibodies and EDC M53-PEG24-CEN09-106

All cell lines were maintained in complete media [RPMI medium 1640 supplemented with 10% (wt/vol) fetal bovine serum and Gentamycin (50 µg/ml)]. Cells were plated at a density of 5000 (H460 and A549) or 7500 (HCT15 and MCF7) cells per well of each 96-well clear bottom tissue culture treated microtiter plate in 100 ul complete media, then were grown for 72 hour at 37° C. with 7% $CO_2$ in a humidified incubator before antibody staining. To stain, the media was removed and 100 ng/100 uL of M53 or M53-PEG24-CEN09-106 in PBS with 0.9 mM CaCl2, 0.5 mM MgCl2, and 1.5% FBS were added to each well and incubated at room temperature for 30 min. Wells were washed 2× with 100 uL of the antibody diluent; then, 100 uL of a 5 ug/mL solution of goat anti mouse IgG, DyLight 488 (cat. number: 35503, Pierce Biotechnology) in the antibody dilution buffer were added to each well and allowed to incubate 30 min at room temperature. Wells were washed 1× with 100 uL of the antibody diluent, and cells were imaged using a Nikon Diaphot-TMD inverted fluorescence microscope.

Data showed that the M53 antibody stained all cell lines tested in Example 5 with the exception of MCF7 cells, where no detectable staining above background was observed. Data also showed that the M53-PEG24-CEN09-106 antibody drug conjugate strongly stained the H460 cell, which was comparable to the unconjugated M53 staining.

Taken together and specific to the synergy embodiment, the results of Examples 5 and 6 demonstrate that not all cells express FXYD5 on their surface and, when FXYD5 is not expressed, synergy of the antibody to FXYD5 in these EDCs and agent does not occur.

Example 7

EDC Cell Internalization Study

To demonstrate that illustrative compounds of the invention are not internalized, the purpose of this experiment was to observe whether an EDC (M53-PEG24-CEN09-106) or parent monoclonal antibody (M53) are internalized within cells after binding to its cell-surface antigen.

This experiment was modeled after the internalization study performed by Poison et al. (Antibody-Drug Conjugates for the Treatment of Non-Hodgkin's Lymphoma: Target and Linker-Drug Selection. Cancer Res 2009; 69: (6): 2358-64). Briefly, H460 cells (large cell lung cancer) were seeded into 96-well, clear bottom, tissue culture treated plates at a density of 10,000 cells/well in 100 uL media (RPMI 1640 with 10% fetal bovine serum and 50 ug/mL Gentamicin)/well. Cells were incubated at 37° C. and 7% $CO_2$ for 24 hrs. M53 and M53-PEG24-CEN09-106 were diluted in media, with and without protease inhibitors (10 ug/mL leupeptin, and 5 uM pepstatin), to a final concentration of 2 ug/mL. Media was then aspirated from specified wells and replaced with media containing M53 or M53-PEG24-CEN09-106 (100 uL/well) at time points −21.5 hrs or −3 hrs. At time 0 hrs, media was removed by aspiration and the wells were washed 1× with DPBS+1.5% FBS. Cells were then fixed with 4% formaldehyde in PBS for 20 min at room temp and permeabilized with 0.1% TritonX-100 in PBS for 15 min at room temp. Cells that did not receive antibody during culture were stained with M53 or M53-PEG24-CEN09-106 after fixation and permeabilization. Cells were then washed ×2 with DPBS+1.5% FBS. Goat anti-mouse IgG Dylight® 488 conjugate (Thermo) secondary was diluted to 5 ug/mL in DPBS+1.5% FBS and added to all wells at 100 uL/well and incubated for 30 min at room temp. Cells were again washed, and then viewed with Nikon Diaphot TMD inverted trinocular fluorescence phase contrast microscope with Ph2 20×DL objective. Pictures were captured using an Olympus E-450 Digital SLR camera, and the brightness of fluorescence images were adjusted using GIMP 2.6 software.

Cells stained with M53 and M53-PEG24-CEN09-106 exhibited a fluorescence staining pattern typical of surface staining (bright staining seen along boarders and junctions of cells) after 21.5 hrs, and 3 hrs or stained post fixation. Poison et al. (supra) concluded that Ab-surface receptor complexes were poorly internalized if cells exhibited a staining pattern around the cell periphery after incubating with Ab for 20 hrs. However, internalized Ab-receptors yield a punctate staining pattern located within the cells characteristic of being confined to endosomal compartments. Because the mAb and EDC both exhibit a staining pattern characteristic of surface staining at all time points, the results support the conclusion that this EDC is not internalized within cells upon binding of cell surface antigen.

Taken together, the results of Example 7 and FIG. 7 demonstrate that internalization is not required for EDC activity.

Example 8

M53 Competition Study of M53-PEG24-CEN09-106

To illustrate that compounds of the invention require binding of the antibody used in the EDC of the invention, therapeutic agents with activity toward the Na,K-ATPase were attached to FXYD5 specific antibodies through the PEG24 non-cleavable linkers and activity abolished with excess free anti-FXYD5 antibody which competes for the FXYD5 target. For the experiment below, α-Fl-CEN10-105 (also termed α-Fl-106), CEN10-105-Cys (also termed PEG24106) and M53-PEG24-CEN09-106 were varied as indicated in FIG. 11. For the competition experiment (M53 Comp), M53-PEG24-CEN09-106 was added at 1 nM to all reactions and varying amounts of unconjugated antibody M53 were added. All were assayed in the A549 cell proliferation assay. Cells were maintained in complete media [RPMI medium 1640 supplemented with 10% (wt/vol) fetal bovine serum and Gentamycin (50 μg/ml)]. Cells were plated at a density of 1250 per well of a 384-well white tissue culture treated microtiter plate in 20 uls complete media, then were grown for 24 hour at 37° C. with 7% $CO_2$ in a humidified incubator before agent/conjugate addition. In a separate 96-well plate, agent and antibody conjugate (in PBS) stocks were serially diluted in complete media at 5× final working concentrations, and 5 uls added to the cells used in the assay. For the competition assay (M53 Comp) M53 was serially diluted from 500 to 0.11 nM in the presence of 5 nM PEG24-106, and 5 ul of these dilutions were added to cells used in this assay. Cells were incubated with the agent/conjugate for 3 days before cell viability testing. Cell viability testing used the CellTiterGlo luminescent cell viability assay (Promega, Madison, Wis.).

The data in FIG. 11 shows that when the concentration of M53 antibody is approximately 5 times above that of the M53-PEG24-CEN09-106 conjugate, it can compete and remove the activity of the M53-PEG24-CEN09-106 conjugate. The figure demonstrates that 5.5 nM is the level at which NCC-53 can half maximally competes the cytotoxic effect of 1 nM M53106. Again, the EDC M53-PEG24-CEN09-106 shows the strong ability to kill the A549 cells (IC50 1.983e-10 molar). The data also shows that the free agent when conjugated to the non-cleavable linker and capped with cysteine to mimic a possible breakdown product (PEG24-CEN09-106) has a similar IC50 to the ADCs produced using the antibody to fluorescein to produce ADC anti-Fl-CEN10-105, which is close to 1000× less active at killing the A549 cells than the M53-16 EDC.

The results of Example 8 demonstrates that, when antibody binding no longer exists, EDC activity is lost.

Example 9

IC50 of M53-PEG24-CEN09-106 (M53-106) on Various Cell Lines with Both Targets not in Close Proximity Also as stated in the antibody section, the EDCs of the invention are primarily active only when the antibody is bound to its target and that target is in close proximity to the therapeutic agent's target. This, in effect, increases selectivity, because both target sites need to be not only present, but also present in close proximity to one another.

| Cell Line | M53-106 | α-Fl-106 | PEG24-106 | CEN09-106 | M53 TARGET | Origen | Disease |
| --- | --- | --- | --- | --- | --- | --- | --- |
| A549 | 0.2 | 180 | 120 | 0.7 | YES | LUNG | carcinoma (squamous) |
| H460 | 0.5 | 320 | 240 | 1.6 | YES | LUNG | carcinoma (large cell) |
| SKOV3 | 1.1 | ND | 310 | 5.3 | YES | OVARY | adenocarcinoma |
| A431 | 2.2 | 380 | 360 | 2.0 | YES | SKIN | epidermoid carcinoma |
| A375 | 0.6 | ND | 360 | 3.2 | YES | SKIN | Malignant melanoma |
| MALME-3M | 2.8 | ND | ND | 5.4 | YES | SKIN | malignant melanoma |
| MEL2 | ND | ND | ND | 4.3 | YES | SKIN | malignant melanoma |

| Cell Line | M53-106 | α-Fl-106 | PEG24-106 | CEN09-106 | M53 TARGET | Origen | Disease |
|---|---|---|---|---|---|---|---|
| HT29 | ND | 220 | 210 | 3.1 | YES | COLON | colorectal adenocarcinoma |
| HCT15 | ND | 380 | 210 | 2.3 | YES | COLON | colorectal adenocarcinoma |
| MB-231 | ND | ND | ND | 7.0 | YES | BREAST | adenocarcinoma |
| MCF10a | ND | ND | ND | 6.6 | YES | BREAST | fibrocystic disease |
| MCF7 | ND | 900 | 380 | 2.6 | NO | BREAST | adenocarcinoma |

The table above shows the IC50 data (in nanomolar) of the EDC M53-PEG24-CEN09-106 (M53-106), ADC α-Fl-106, agent with attached linker PEG24-106 and free drug CEN09-106 when added to various human cell lines. ND indicates IC50 values that could not be determined at the concentrations tested. The presence of the antibody M53's target on the cell surface as determined by M53 cell staining is indicated as Yes/No. The origin of the cell line and disease type for each cell line is also indicated.

The table above shows various cell line sensitivities to the EDC of the invention where the antibody is M53 (specific to human FXYD5), the linker is a polyethylene glycol linker and the agent is a cardiac glycoside. The data shows that this EDC of the invention displays strong cytotoxic activity (<3 nM) on cell types where the antibody's target and the agent's target are in close proximity (A549, H460, SKOV3, A431, A375, and MALME-3M) and poor activity on cell types where the antibody's target is not present (MCF7) or where the targets are present but not in close proximity (MEL2, HT29, HCT15, MB-231 and MCF10a). Strong activity of the free agent indicates that the agent's target is present and cell staining of the M53 antibody indicates that the antibody's target is present. The table above also shows various cell line sensitivities to the ADC where the antibody is α-Fl (specific to Flourescein which is not a target on the cell surface), the linker is a polyethylene glycol linker and the agent is a cardiac glycoside. The data shows that this EDC displays weak cytotoxic activity (>100 nM IC50) on cell types tested even when the cells displayed strong sensitivity to the agent alone. Thus, the EDCs of the invention are largely inactive when the antibody or other targeting moiety is not bound to a target on the cell surface. The EDCs of the invention are also largely inactive when the antibody is bound to its target when the drug's target is not in close proximity. In this case, the linker is not long enough to allow the drug to reach its target while attached to the antibody.

Example 10

Synthesis and Cytotoxicity Testing of a Therapeutic Agent to Smoothened

This example illustrates a drug-conjugate of the invention in which the target of the targeting moiety is smoothened and the drug is a cyclopamine derivative. In this example, the target for the agent and the antibody is the same, and the antibody's epitope binding does not interfere with simultaneous binding of the agent. The agent can be synthesized as follows. Cyclopamine (1), a natural product isolated from *Veratrum californicum*, (*Phytochemistry* 1968, 7, 303-306 and Phytochemistry 1969, 8, 223-225 and Teratology 1968, 1, 5-10) inhibits hedgehog signaling by binding to surface protein smoothen (SMO) (Genes Dev. 2002, 16, 27432748). Its analog KAAD-cyclopamine (2) is more potent than 1 (Proc. Natl. Acad. Sci. USA 2002, 99, 14071-14076). Synthesis of an analog of 2 (i.e. 7) that is suitable for conjugation to and antibody is shown in scheme 1.

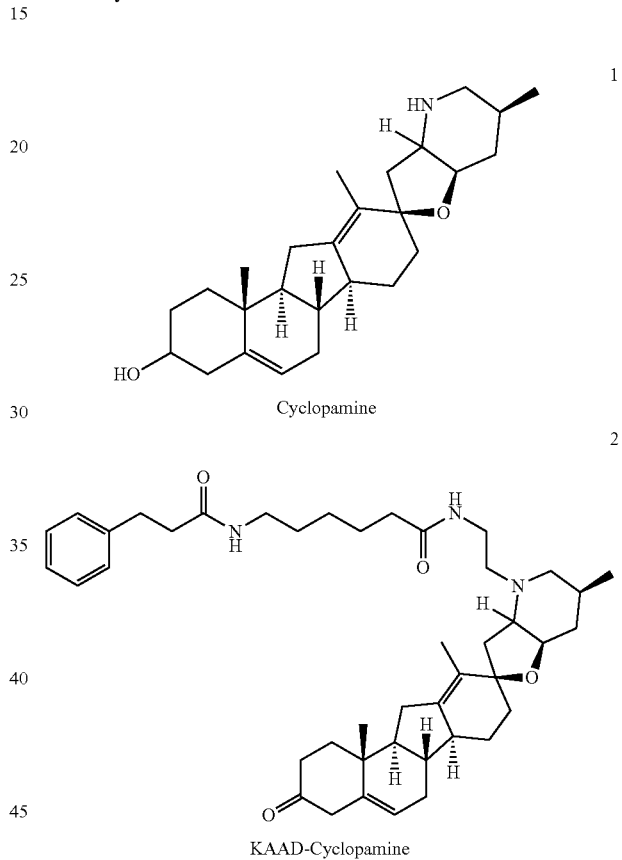

Cyclopamine

KAAD-Cyclopamine

Considering the acid sensitivity of 1, exposure of all intermediates to strong acid is avoided throughout the synthesis (see Teratology 1970, 3, 169-173). Thus aldehyde 4 is readily prepared by oxidation of the commercially available Fmoc-6-aminohexanol (3) (see J. Med. Chem. 2007, 50, 6133-6143 and J. Org. Chem. 2007, 72, 7222-7228 and J. Am. Chem. Scoc. 2002, 124, 4180-4181).

Scheme 1

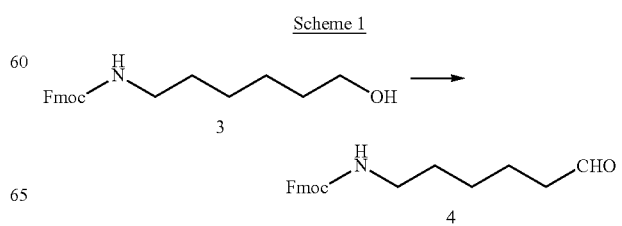

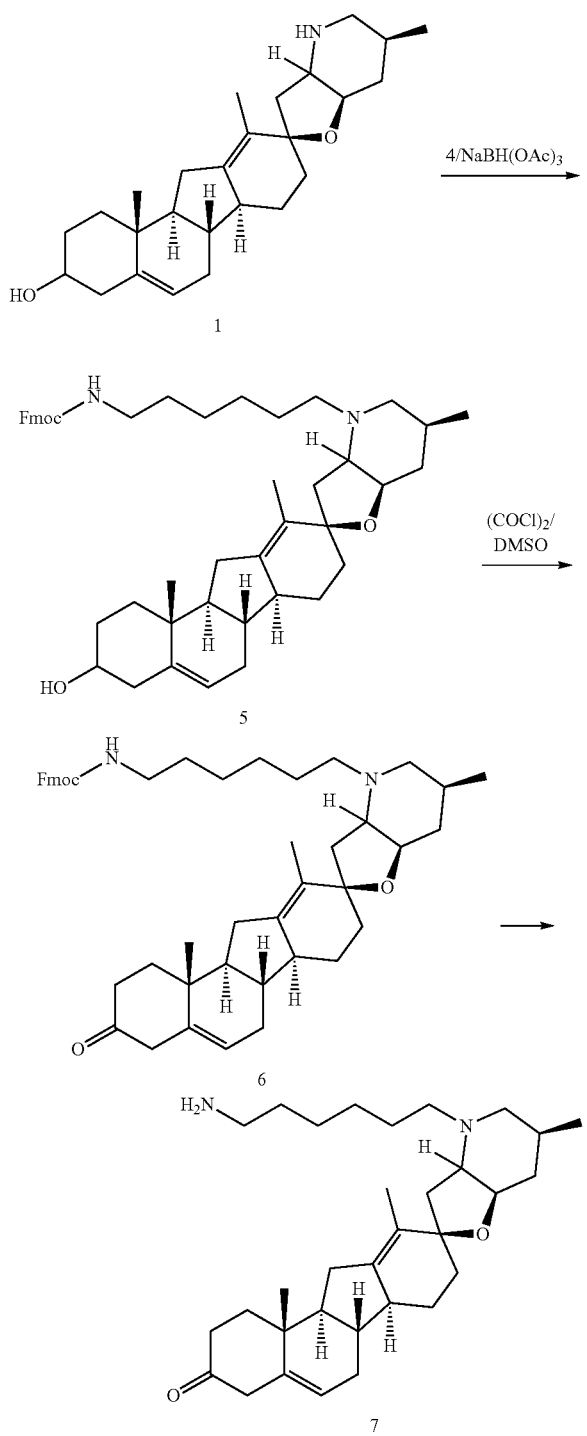

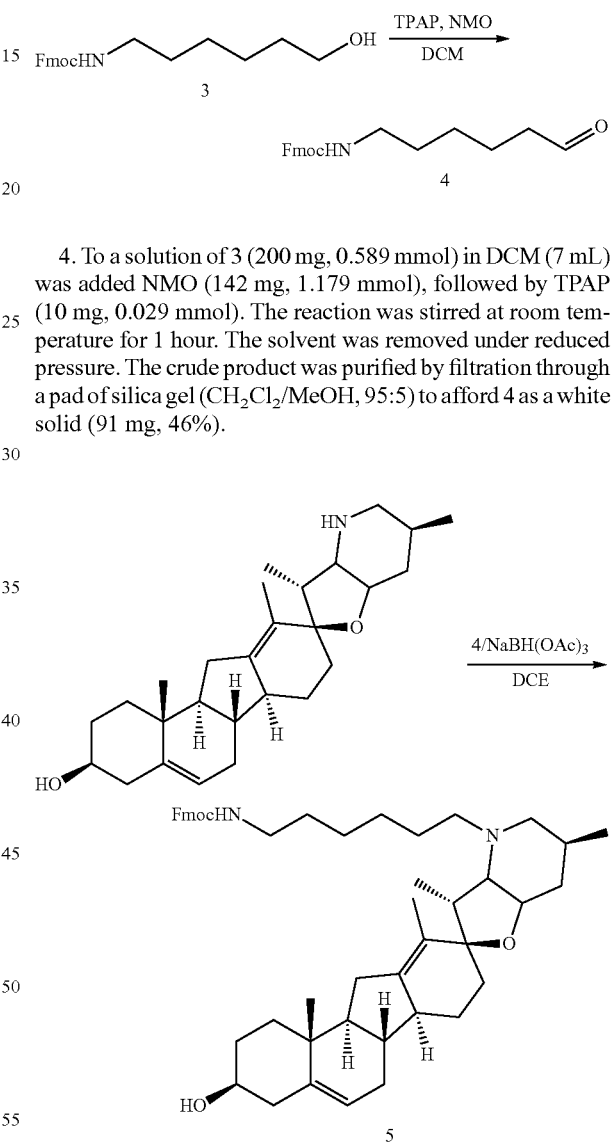

Reductive amination of the aldehyde 4 with cyclopamine 1 with will afford 5 (see Tetrahedron Lett. 1990, 31, 5595-5598 and PTC Intl. Appl. 2006, WO 2006026430). Oxidation of 5 with oxalyl chloride and DMSO will give 6. Finally, deprotection of 6 will give the desired compound 7 that can be coupled to a linker via the free primary amino group and hence to a targeting moiety that binds to the cell extracellular target smoothened.

Fmoc-6-aminohexanol (3). 6-Amino-hexan-1-ol (1.5 g, 12 mmol) was added to a vigorously stirred solution of $Na_2CO_3$ in $H_2O$ at 0° C. Dioxane (30 mL) was added, providing an opaque mixture. A solution of FmocCl, in dioxane (36 mL) was added dropwise at 0° C. The mixture was then allowed to warm to room temperature and was stirred for 1 hour. AcOEt (300 mL) was added, followed by HCl 0.1M (200 mL). The organic layer was washed with $H_2O$ (200 mL) and brine (50 mL), then dried over $Na_2SO_4$, filtered and concentrated. The crude product was purified by flash chromatography ($CH_2Cl_2$/MeOH, 97:3 to 90:10) to afford 3 as a white solid (3.95 g, 97%).

4. To a solution of 3 (200 mg, 0.589 mmol) in DCM (7 mL) was added NMO (142 mg, 1.179 mmol), followed by TPAP (10 mg, 0.029 mmol). The reaction was stirred at room temperature for 1 hour. The solvent was removed under reduced pressure. The crude product was purified by filtration through a pad of silica gel ($CH_2Cl_2$/MeOH, 95:5) to afford 4 as a white solid (91 mg, 46%).

5. Cyclopamine (73 mg, 0.178 mmol) and 4 (90 mg, 0.267) were dissolved in DCE (5 mL). $NaHB(OAc)_3$ (56 mg, 0.249 mmol) was added and the reaction was stirred at room temperature overnight. The reaction was quenched with saturated $NaHCO_3$, extracted with DCM (2×30 mL), dried over $Na_2SO_4$, filtered and concentrated. The crude product was purified by flash chromatography ($CH_2Cl_2$/MeOH, 97:3 to 90:10) to afford 5 as a white solid (120 mg, 85%). ESIMS (m/z): calcd for $C_{48}H_{64}N_2O_4$ $[M+H]^+$: 733.5. found 733.6.

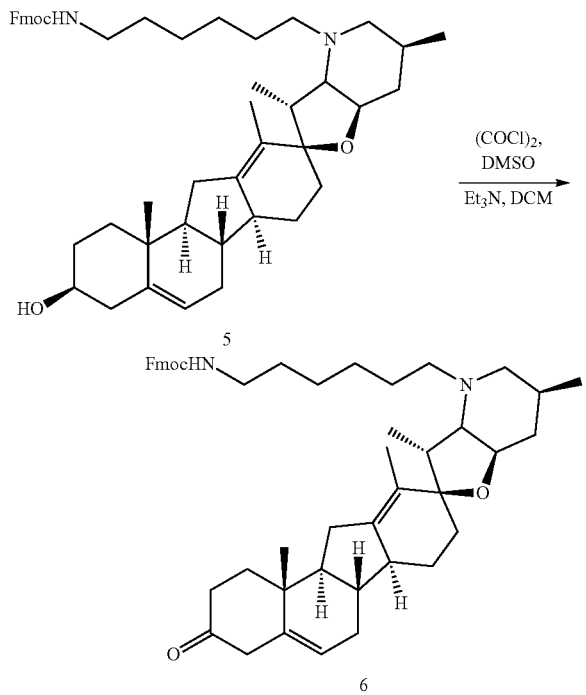

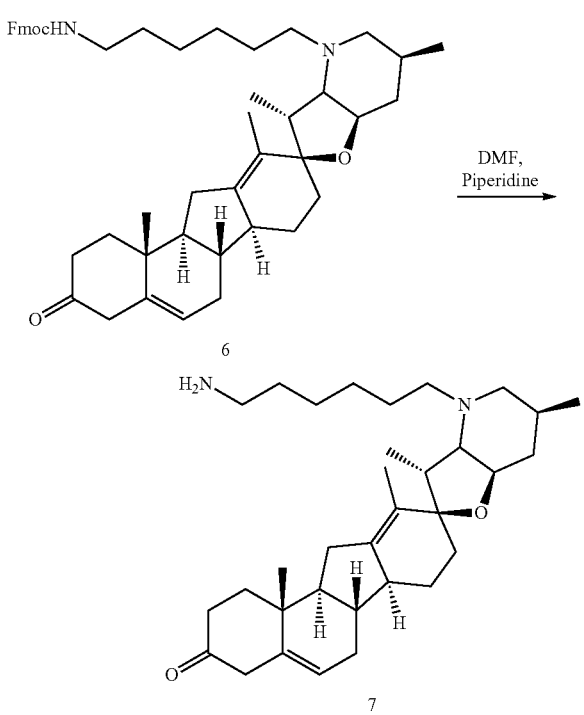

6. DMSO (0.252 mL, 3.546 mmol) was added to a solution of (0001)$_2$ (0.15 mL, 1.775 mmol) in dry DCM (5 mL) at −78° C. under argon. After the mixture was stirred at −78° C. for 10 min, a solution of 5 (120 mg, 0.164 mmol) in dry DCM (5 mL) was added and the reaction was stirred at −78° C. for 30 min. TEA (0.741 mL, 5.324 mmol) was added to the reaction mixture and the stirring was continued at −78° C. for an additional period of 10 minutes. The mixture was allowed to warm to the room temperature. The reaction was quenched with saturated NaHCO$_3$, extracted with DCM, dried over Na$_2$SO$_4$, filtered and concentrated. The crude product was purified by flash chromatography (CH$_2$Cl$_2$/MeOH, 99:1 to 97:3) to afford 6 as a white solid (25 mg, 21%). ESI (m/z): calcd for C$_{48}$H$_{62}$N$_2$O$_4$ [M+H$^+$]$^+$: 731.5. found 731.7.

7 (CEN10-125). 6 (23 mg, 0.032 mmol) was dissolved in DMF (2 mL). Piperidine (0.4 mL) was added, and the mixture was stirred at room temperature. DMF was removed under reduced pressure. The crude product was purified by flash chromatography (CHCl$_3$/MeOH/Et$_3$N, 20:40:0.1) to afford 7 as a white solid (14 mg, 85%). HPLC analysis [Luna C$_{18}$, 250×4.60 mm, 5 p.m, 50% to 90% AcN with 10% Ammonium formate, over 18 minutes, 1 ml·min$^{-1}$] indicated a relatively pure compound (>90%). ESI (m/z): calcd for C$_{48}$H$_{62}$N$_2$O$_4$ [M+H$^+$]$^+$: 509.4. found 509.5.

Synthesis of CEN10-125 to PEG24 linker to produce CEN10-130.

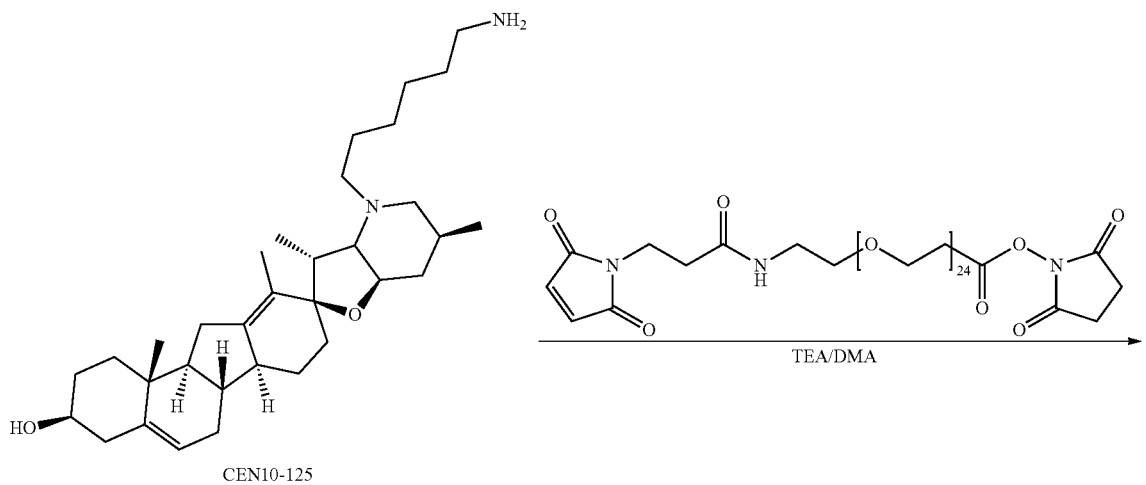

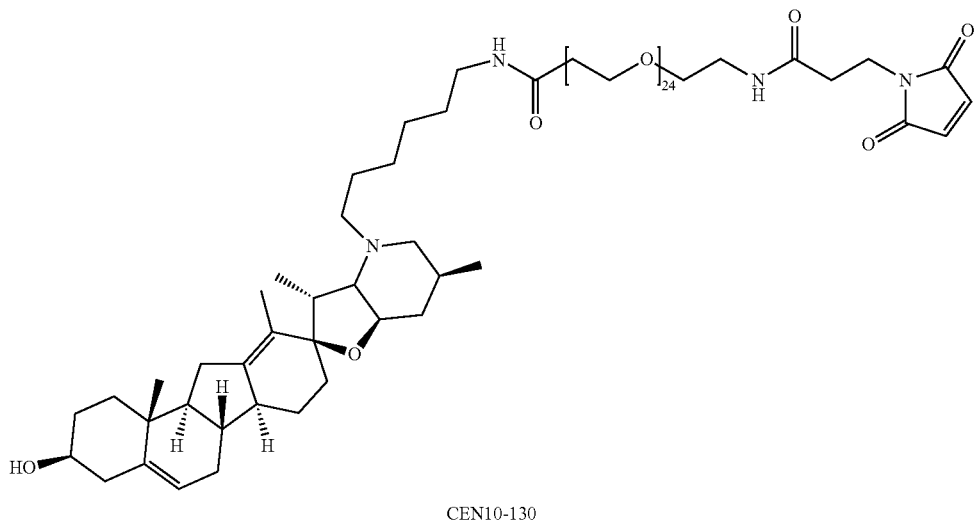

CEN10-130

CEN10-130: To a stirred solution of CEN10-125 (15 mg, 0.029 mmol) in DMA (1 mL) was added NHS-PEG$_{24}$-Maleimide (40 mg, 0.029 mmol). Triethylamine (20 µL, 0.147 mmol) was added and the mixture was stirred at room temperature for 16 hours. It was then concentrated under reduced pressure and the residue was purified by silica gel flash chromatography with 99:1 DCM:MeOH to 95:5 DCM:MeOH to afford CEN10-130 as a clear oil (35 mg, 0.019 mmol, 67%). ESI MS: m/z calculated for $C_{91}H_{160}N_2O_{30}Na$ [M+Na]$^+$ 1812.10. observed 1812.02.

Cyclopamine and derivative CEN10-130 were then tested in vitro for cytotoxic activity toward A549 lung cancer cells as described in Example 5 at working concentrations (0.9 to 1000 uM). The IC50 of cyclopamine and CEN10-130 were found to be 392 and 244 uM respectively. These results demonstrate that CEN10-130 has cytotoxic activity similar to its parent cyclopamine when tested on the A549 cell line. Therefore in accordance with the invention, CEN10-130 when coupled to a targeting moiety that recognizes a target in close proximity to cyclopamine's target, simultaneous binding should show a synergistic effect increasing the activity and specificity of the non-cleavable linker linked cyclopamine.

Example 11

Synthesis and Cytotoxicity Testing of a Therapeutic Agent to GLUT Transporter

An experiment was designed to test the cytotoxicity of 2-amino-2-deoxy-D-GlucosePEG24-MAL (GlcNH-PEG24-MAL or also called CEN10-128, and synthetic route.

Synthesis of GlcNHPEG24Mal or CEN10-128. 2-Amino-2-Deoxyglucose (10 mg, 0.046 mmol) was suspended in DMA (1 mL), at room temperature. To the mixture was added TEA (32 µL, 23 mg, 0.23 mmol) and the mixture was stirred for 5 min, followed by the addition of NHSPEG$_{24}$-Maleimide (65 mg, 0.046 mmol). The mixture was stirred for an additional period of 1 hour. The reaction was concentrated under reduced pressure and the resulting residue was purified by silica gel flash chromatography eluting with 98:2 DCM: MeOH to 9:1 DCM:MeOH to give CEN10-128 as a clear oil (24 mg, 0.032 mmol, 70%). ESI MS: m/z calculated for $C_{64}H_{119}N_3NaO_{33}$ [M+Na]$^+$1480.76. observed 1480.76. ?

CEN10-128-cys and 2-amino-2-deoxy-D-Glucose (GlcNH2) were tested for cytotoxicity as described in Example 5 at assay concentrations from 457 nM to 1 mM. CEN10-128 capping was performed by incubating the compound overnight at room temperature with a molar excess of L-cysteine (compounds indicated as CEN10-128-cys. The IC50s of the compounds were determined to be above 1.0 mM for GlcNH2 for both cell lines tested and CEN10-128-cys was found to be 0.1 and 0.04 for cell lines H460 and A549 respectively.

The CEN10-128-cys displayed increased cytotoxic activity when compared to the unlinked GlcNH2. In addition, since pegylation has been shown to improve the half-life of compounds in the blood stream, CEN10-128-cys is also expected to have a longer half-life in the serum. CEN10-128 is the compound which can be directly attached to GLUT transporter specific antibodies to produce EDCs of the invention.

Example 12

Synthesis of CEN10-126 and CEN10-127

1-Bromo-2-deoxy-2-N-phtalimido-3,4,6-tri-O-acetyl-13-D-glucopyranose.

1,3,4,6-tetra-0-acetyl-2-deoxy-2-N-phtalimido-β-D-glucopyranose (2 g, 4.47 mmol), was dissolved in dry DCM (30 mL). HBr (33% in acetic acid, 2.5 mL) was added at 0° C. and the mixture was stirred at 0° C. for 1 hour. The reaction mixture was then poured onto crushed ice. After the ice had melted the mixture was extracted with chloroform. The organic layer was washed with saturated solution of NaHCO$_3$, dried over Na$_2$SO$_4$, filtered and concentrated. The crude was carried further without purification. R$_f$ 0.40 (Hexanes/EtOAc, 50:50).

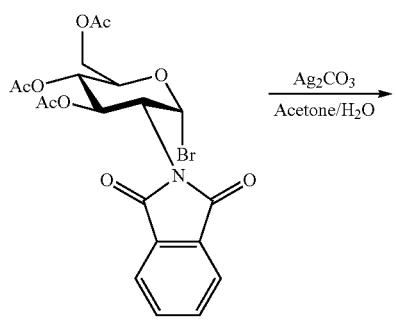

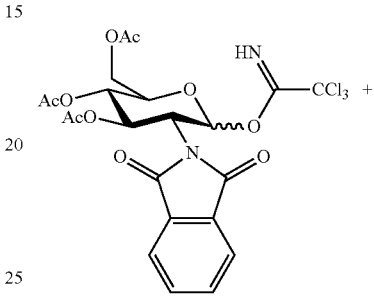

2-Deoxy-2-N-phtalimido-3,4,6-tri-O-acetyl-1̃-D-glucopyranose

Crude 1-bromo-2-deoxy-2-Nphtalimido-3,4,6-tri-O-acetyl-β-D-glucopyranose, was dissolved in acetone (30 mL). H₂O (1 mL) was added and the solution was cooled to 0° C. Ag₂CO₃ (1.23 g, 4.47 mmol) was added and the mixture was stirred at 0° C. for 30 minutes. The reaction mixture was filtered through a pad of celite, the solvent was stripped in vacuum to afford 2-deoxy-2-N-phtalimido-3,4,6-tri-O-acetyl-β-D-glucopyranose as a white foam (1.87 g, 96%) as anomeric mixture (α:β≈1:4). ¹H-NMR (β-anomer, 300 MHz, CDCl₃) δ, 1.86 (s, 3H), 2.03 (s, 3H), 2.10 (s, 3H), 3.93 (ddd, 1H, J=2.3, 4.6, 10.2 Hz, H-5), 4.17-4.30 (m, 3H, H-2, H-6), 5.17 (dd, 1H, J=9.3, 10.0 Hz, H-4), 5.63 (d, 1H, J=8.4 Hz, H-1), 5.83 (dd, 1H, J=9.1, 10.7 Hz, H-3), 7.73 (dd, 2H, J=3.0, 5.5 Hz, H—Ar), 7.85 (dd, 2H, J=3.0, 5.5 Hz, H—Ar); ¹³C-NMR (75 MHz, CDCl₃) δ 20.6, 20.8, 20.9, 56.2, 62.2, 70.7, 72.2, 92.8, 123.8, 131.5, 134.5, 168.0, 169.7, 170.3, 171.0.

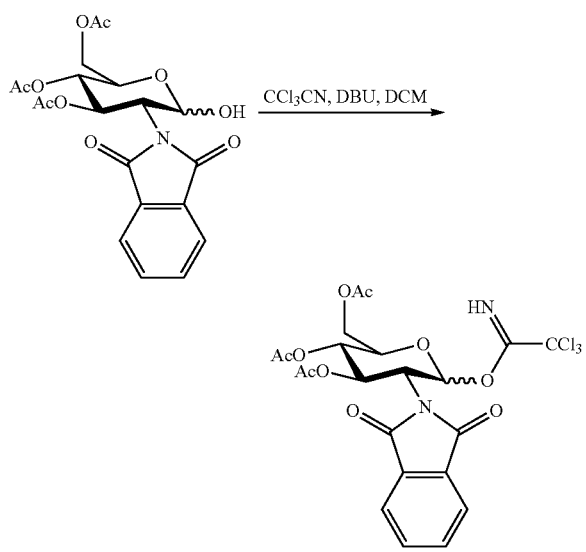

1-Trichloroacetamidyl-2-deoxy-2-N-phtalimido-3,4,6-tri-O-acetyl-β-D-glucopyranose 2-Deoxy2-N-phtalimido-3,4,6-tri-O-acetyl-β-D-glucopyranose (2.1 g, 4.82 mmol) was dissolved in dry DCM (30 mL) and the solution was cooled to 0° C. CCl₃CN (4.84 mL, 48.2 mmoL) was added slowly followed by DBU (0.36 mL, 2.41 mmol). The reaction mixture was stirred at 0° C. for 1 hour. The solvent was evaporated and the crude product was purified by flash chromatography (Hexanes/EtOAc, 50:50 with 0.5% Et₃N) to afford 1-trichloroacetamidate-2-deoxy-2-Nphtalimido-3,4,6-tri-O-acetyl-β-D-glucopyranose (1.45 g, 52%).

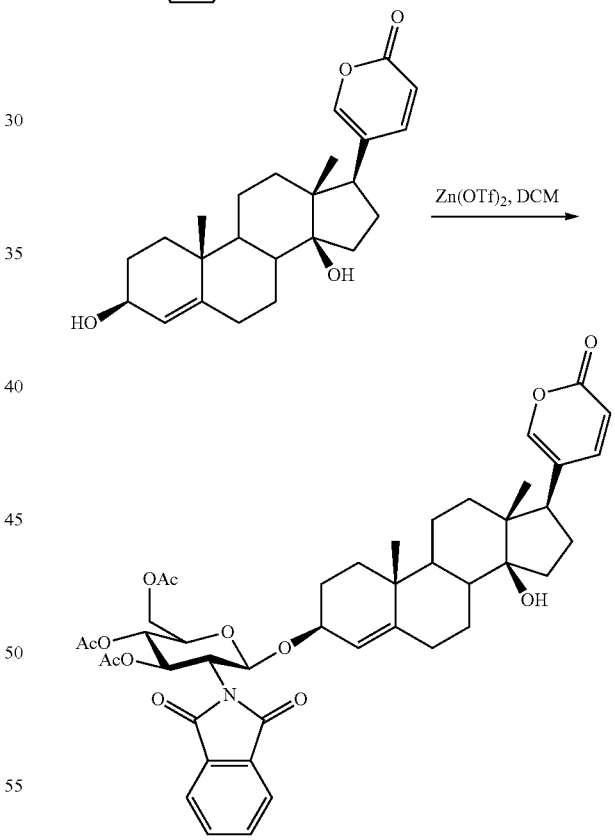

Scillarenin-2-deoxy-2-N-phtalimido-3,4,6-tri-O-acetyl-β-D-glucopyranoside.

To a suspension od activate powdered 4 Å molecular sieves in anhuydrous DCM (40 mL), under argon was added 1-trichloroacetimidate-2-deoxy-2-N-phtalimido-3,4,6-tri-O-acetyl-β-D-glucopyranose (1.45 g, 2.5 mmol) followed by scillarenin (0.961 g, 2.5 mmol). The mixture was cooled to 0° C. Then Zn(OTf)₂ (91 mg, 0.25 mmol) was added and the reaction mixture was stirred for 3.5 hours at 0° C. The reaction was quenched with few drops of Et$_3$N. The mixture was filtered and solvent was removed under reduced pressure. The crude product was purified by flash chromatography (DCM/MeOH, 98:2 to 95:5) to afford scillarenin-2-deoxy-2-N-phtalimido-3,4,6-tri-O-acetyl-β-D-glucopyranoside as a white powder (1.4 g, 71%) R$_f$ 0.27 (DCM/MeOH, 97:3). $^1$H-NMR (300 MHz, CDCl$_3$) δ, 0.68 (s, 3H), 0.86 (s, 3H), 0.90-2.13 (m, 27H), 2.40-2.46 (m, 1H), 3.83-3.89 (m, 1 h, H-5), 4.09-4.35 (m, 4H, H-2, H-6), 5.04 (s, 1H), 5.15 (dd, 1H, J=9.4 Hz, H-4), 5.49 (d, 1H, J=8.6 Hz, H1), 5.78 (dd, 1H, J=9.7, 10.1 Hz, H-3), 6.25 (d, 1H, J=9.7 Hz), 7.20 (d, 1H, J.=2.2 Hz), 7.72-7.88 (m, 4H); $^{13}$C-NMR (75 MHz, CDCl$_3$) δ 16.6, 19.1, 20.6, 20.8, 20.9, 21.4, 26.9, 28.7, 28.8, 32.1, 32.7, 34.8, 37.5, 40.7, 42.8, 48.3, 49.8, 51.2, 55.0, 62.4, 62.3, 71.0, 71.9, 76.2, 77.4, 85.2, 97.5, 115.5, 120.21, 122.7, 123.7, 131.6, 134.4, 146.8, 147.9, 148.7, 162.5, 169.6, 170.4, 170.9. HRMS-ESI (m/z): calcd for C$_{44}$H$_{51}$ NO$_{13}$ [M+NH$_4^+$]$^+$: 819.3704. found 819.3691, [M+Na$^+$]$^+$:824.3258. found 824.3244, [M+K$^+$]$^+$: 840.2997. found 840.2978.

ESI (m/z): calcd for C$_{30}$H$_{43}$NO$_8$ [M+H$^+$]$^+$: 545.3. found 545.3.

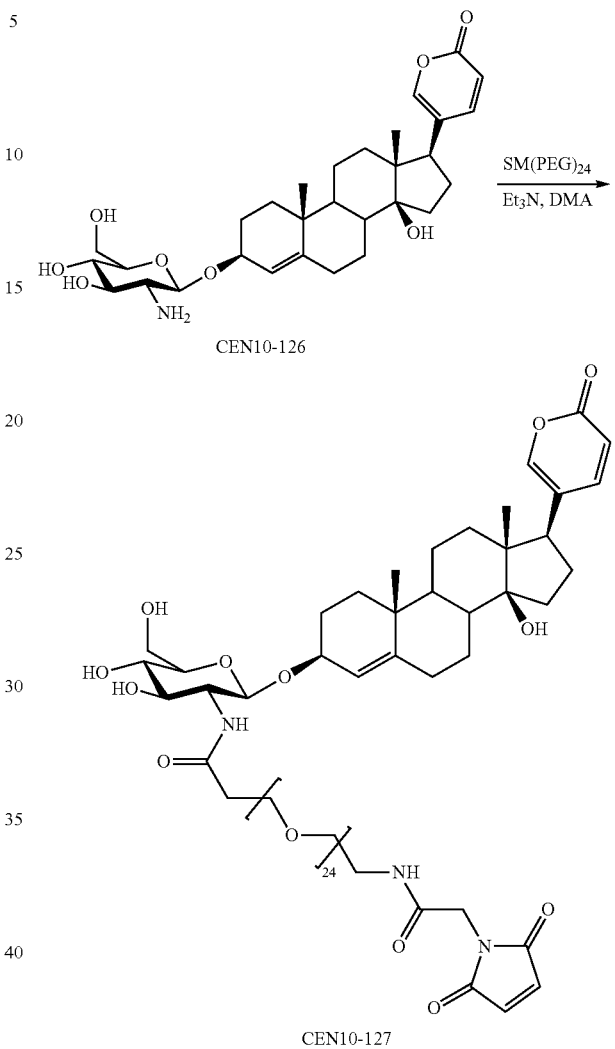

CEN10-126

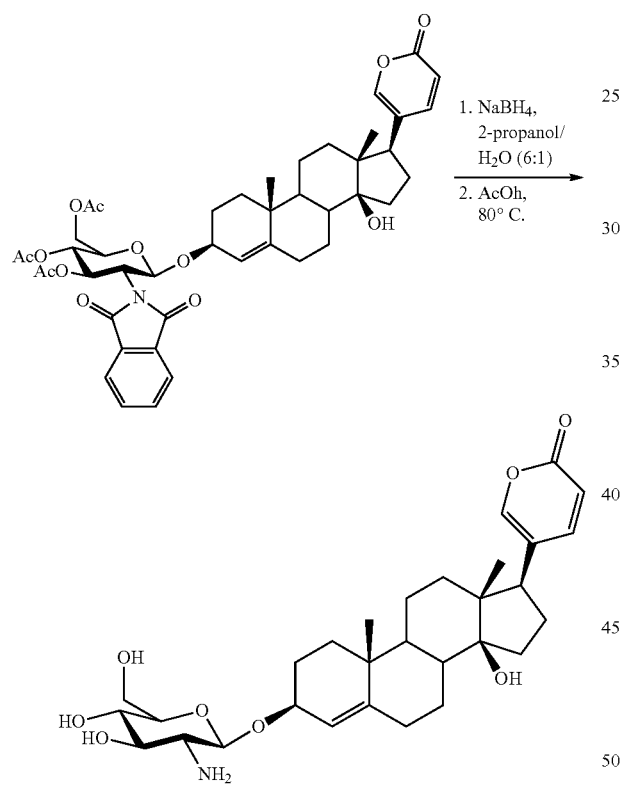

Scillarenin-2-deoxy-2-amino-13-D-glucopyranoside (CEN10-126)

Scillarenin-2-deoxy-2-N-phtalimido-3,4,6-tri-O-acetyl-β-D-glucopyranoside (100 mg, 0.125 mmol) was dissolved in a 6:1 mixture of 2-propanol and water (1.5 mL). NaBH$_4$ (33 mg, 0.873 mmol) was added and the mixture was stirred at room temperature overnight. Glacial acetc acid was added dropwise to adjust the pH to 4.5. The mixture was then heated at 80° C. overnight. Solvent was evaporated under reduced pressure and the crude product was purified by HPLC (Gemin C18, 5 vm, 4.6×250 mm 10% to 90% ACN in H20, 0.1% TFA) to afford scillarenin-2-deoxy-2-amino-β-D-glucopyranoside as an oil (25 mg, 30%).

CEN10-127.

CEN10-126 (11 mg, 0.0167 mmol) was dissolved in DMA (1 mL). SM(PEG)$_{24}$ (23 mg, 0.0167 mmol) was added followed by Et$_3$N (12 μl, 0.0835 mmol). The reaction was stirred at room temperature for 24 hours. The solvent was evaporated under reduced pressure. The crude product was purified by HPLC (Gemin C18, 5 p.m 10% to 90% ACN in H$_2$O with 0.1% TFA) to afford CEN10-127 (7.5 mg, 25%).

HRMS-ESI (m/z): calcd for C$_{88}$H$_{149}$N$_3$O$_{36}$ [M+Na$^+$]$^+$: 1846.9921. found 1846.9968.

Example 13

Effects of Linker Length on M53 EDC Activity

In this experiment, conjugates of antibody M53 with Mal-PEG2-CEN09-106 (CEN10-103), Mal-PEG12-CEN09-106 (CEN10-107), Mal-PEG24-CEN09-106 (CEN10-105) and Mal-PEG36-CEN09-106 (CEN10-131) were prepared by methods described in example 5. The loading ratios (mol Drug/mol Ab) were calculated as described in example 5 and are shown in the table below.

| ADC | Molar Ratio Agent/Antibody |
|---|---|
| M53-PEG2-CEN09-106 | 2.4 |
| M53-PEG12-CEN09-106 | 1.5 |
| M53-PEG24-CEN09-106 | 2.3 |
| M53-PEG36-CEN09-106 | 1.9 |

Cytotoxicity of the above EDCs were evaluated in vitro on the NSCLC line A549. Cells were maintained in complete media [RPMI medium 1640 supplemented with 10% (wt/vol) fetal bovine serum and Gentamycin (50 µg/ml)]. Cells were plated at a density of 1250 per well of a 384-well white tissue culture treated microtiter plate in 20 uls complete media, then were grown for 24 hour at 37° C. with 7% $CO_2$ in a humidified incubator before conjugate addition. In a separate 96-well plate, ADC (in PBS) stocks were serially diluted in complete media at 5× final working concentrations, and 5 uls added to the cells used in the assay. Cells were incubated in the presence of the compounds for 72 hrs prior to cell viability testing. Cell viability testing was performed using the CellTiter-Glo luminescent cell viability assay (Promega, Madison, Wis.).

The IC50 (nM) values determined for the ADCs and agents are shown in the table below.

| Test Compound | IC50 (nM) |
|---|---|
| M53-PEG2-CEN09-106 | 112 |
| M53-PEG12-CEN09-106 | 42.2 |
| M53-PEG24-CEN09-106 | 1.21 |
| M53-PEG36-CEN09-106 | 0.39 |

As can be seen, the PEG36 linker length construct resulted in the lowest $IC_{50}$ value (greatest potency).

Example 14

Effects of Length of Linker on Parent (CEN09-106) Activity

The parent CEN09-106 compound and its linker modified forms Mal-PEG2-CEN09-106, Mal-PEG12-CEN09-106, Mal-PEG24-CEN09-106, and Mal-PEG36-CEN09-106 (described in Example 12) were evaluated for cytotoxicity The reactive maleimide groups of mal-$PEG_n$-CEN09-106 were capped by reacting stock solutions of these compounds solution with a 1.5 molar excess of L-cysteine; these were used as the agent alone controls.

Cytotoxicity of the above compounds were evaluated in vitro on the NSCLC line A549. Cells were maintained in complete media [RPMI medium 1640 supplemented with 10% (wt/vol) fetal bovine serum and Gentamycin (50 µg/ml)]. Cells were plated at a density of 1250 per well of a 384-well white tissue culture treated microtiter plate in 20 uls complete media, then were grown for 24 hour at 37° C. with 7% $CO_2$ in a humidified incubator before agent addition. In a separate 96-well plate, agent stocks were serially diluted in complete media at 5× final working concentrations, and 5 uls added to the cells used in the assay. Cells were incubated in the presence of the compounds for 72 hrs prior to cell viability testing. Cell viability testing used the CellTiter-Glo luminescent cell viability assay (Promega, Madison, Wis.).

The $IC_{50}$ (nM) values determined for the ADCs and agents are shown in the table below.

| Compound | IC50 (nM) |
|---|---|
| CEN09-106 | 0.46 |
| Cys-PEG2-CEN09-106 | 5.38 |
| Cys-PEG12-CEN09-106 | 18.0 |
| Cys-PEG24-CEN09-106 | 59.8 |
| Cys-PEG36-CEN09-106 | 57.7 |

Example 15

Effects of Drug on EDC Activity

In this example, illustrative compounds of the invention were made in order to analyze the effect of the drug's potency and linkage site on final EDC activity. Different drugs with differing cytotoxic activities (all specific to the alpha subunit of the Na,K-ATPase) were coupled to a PEG24 linker and also coupled to M53 antibody mixtures through the same PEG24 linker, tested and compared. The data (when CEN09-106 was used as the drug) shows that this drug produces the most potent EDC of the series. The data (when CEN09-104 was used as the drug) also shows that this drug produced a less potent EDC. The data (when CEN10-126 was used as the drug) also shows that this drug produced the least potent EDC of the series. Taken together, these data suggest that more potent drugs can produce optimal EDCs yet the attachment site of the drug to the linker-antibody can greatly affect potency.

Parent CEN09-106, CEN09-104 and CEN10-126 drugs were all linked to antibody M53 via the PEG24 linker as described in Example 5. The intermediate drug-PEG24's were capped with cysteine as described in Example 5. Cytotoxicity of the EDC's and the drug-PEG24 linkers were evaluated in vitro on the NSCLC line A549 and malignant melanoma cell line A375 as described in Example 5. The $IC_{50}$ (nM) values were determined and are shown in the table below.

| | A549 | A375 |
|---|---|---|
| CEN09-106 | .50 | 1.4 |
| PEG24-CEN09-106 | 60 | 220 |
| M53-PEG24-CEN09-106 | 0.2 | 1.5 |
| CEN09-104 | 92 | 230 |
| PEG24-CEN09-104 | 450 | 2200 |
| M53-PEG24-CEN09-104 | 48 | 180 |
| CEN10-126 | 1.3 | — |
| PEG24-CEN10-126 | 304 | — |
| M53-PEG24-CEN10-126 | ND | — |

The Table above shows $IC_{50}$ values in nanomolar of the agent, linker-agent, and conjugates when tested on A549 and A375 cell lines. ND (not detected) indicates $IC_{50}$ values could not be assigned within the given concentration ranges tested. A dashed line indicates that this test was not performed.

It will be noted that when the potent agent CEN09-106 is attached to the PEG24 linker (PEG24-CEN09-106) and capped, the activity decreases significantly (>100-fold) when compared to the free uncoupled agent. Furthermore, when this potent agent is coupled to the highly specific targeting moiety (M53), the activity increases. On the other hand, when the less potent agent CEN09-104 was attached to the PEG24 linker and capped, the activity decreases yet not significantly (~5-fold) when compared to the free uncoupled agent.

The data also show that when this agent is coupled to the highly specific targeting moiety (M53), the activity increases but not to the level of the CEN09-106 derived EDC. This indicates that for optimal EDC production, it is preferred to link a potent agent to a high affinity targeting moiety through a stable or non-cleavable linker. Furthermore, when the potent agent CEN10-126 is attached to the PEG24 linker and capped, the activity decreases significantly (almost 300-fold) when compared to the free uncoupled agent. When CEN10-126 is coupled to the highly specific targeting moiety (M53), the activity decreases significantly to the point where activity cannot be determined. This indicates that for optimal EDC production, a potent agent should be linked to a high affinity targeting moiety through a stable or non-cleavable linker where the linkage to the agent does not interfere with agent binding to its target. In the case of CEN10-126, the amine which links the agent to the linker is at a position that detrimentally interferes with agent activity and thus EDC activity.

conjugate comprising a targeting moiety linked by a non-cleavable linker to a therapeutic agent, wherein the targeting moiety comprises an antibody that binds to human FXYD5, wherein the therapeutic agent acts on an extracellular target and is selected from the group consisting of CEN08-178 (3-O-digitoxigenin-L-riboside), CEN08-193 (3-O-iso-digitoxigenin-L-xyloside), CEN08-243 ((3S)-3-N-methoxyamino-scillarenin-L-neo-4-amino-4-deoxy-xyloside), CEN08-244 ((3S)-3-N-methoxyamino-scillarenin-L-neo-4-amino-4-deoxyriboside), CEN09-106 (scillarenin-4-amino-4-deoxy-L-xylopyranoside), and CEN09-107 (scillarenin-4-amino-4-deoxy-L-ribopyranoside), and wherein the non-cleavable linker comprises polyethylene glycol (PEG).

2. The method of claim 1, wherein the cancer is a metastasis.

---

---

We claim:

1. A method for treating cancer, comprising administering to a human cancer patient in need of treatment for said cancer a therapeutically effective amount of an extracellular drug 3. The method of claim 1, wherein the cancer is selected from the group consisting of: squamous cell lung carcinoma, large cell lung carcinoma, ovarian adenocarcinoma, epidermoid carcinoma, and malignant melanoma.

* * * * *